(12) United States Patent
James et al.

(10) Patent No.: US 10,825,570 B2
(45) Date of Patent: *Nov. 3, 2020

(54) CLINICAL CONTENT-DRIVEN ARCHITECTURE SYSTEMS AND METHODS OF USE

(71) Applicant: General Electric Company, Schenectady, NY (US)

(72) Inventors: Alan Ferris James, Murray, UT (US); Nitin Agrawal, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 221 days.

This patent is subject to a terminal disclaimer.

(21) Appl. No.: 15/874,390

(22) Filed: Jan. 18, 2018

(65) Prior Publication Data

US 2018/0144830 A1 May 24, 2018

Related U.S. Application Data

(63) Continuation of application No. 13/401,057, filed on Feb. 21, 2012, now Pat. No. 9,911,167.
(Continued)

(51) Int. Cl.
*G16H 70/00* (2018.01)
*G06Q 50/22* (2018.01)
(Continued)

(52) U.S. Cl.
CPC .............. *G16H 70/00* (2018.01); *G06F 19/00* (2013.01); *G06Q 50/22* (2013.01); *G06Q 50/24* (2013.01); *G16H 10/60* (2018.01); *G16H 40/20* (2018.01)

(58) Field of Classification Search
CPC ............................... G16H 10/60; G16H 40/20
See application file for complete search history.

(56) References Cited

U.S. PATENT DOCUMENTS

| 5,832,488 A | 11/1998 | Eberhardt |
| 6,269,340 B1 | 7/2001 | Ford et al. |

(Continued)

OTHER PUBLICATIONS

Chen, et al. "Stucturalized Context-aware Content and Scalable Resolution Support for Wireless VoD Services," Consumer Electronics, IEEE Transactions, vol. 55, Issue 2, pp. 713-720, May 2009.
(Continued)

*Primary Examiner* — Sheetal R Paulson
(74) *Attorney, Agent, or Firm* — Hanley, Flight and Zimmerman, LLC

(57) ABSTRACT

Certain examples provide methods, systems and apparatus of content-driven clinical information management. An example method includes facilitating authoring of content and combination of the content into a content-based application, wherein content represents a parameterization of instructions to instruct the content-based application how to operate, the content formulated according to one or more detailed clinical models. The example method includes packaging and deploying the content-based application using a processor to one or more targets for installation. The example method includes facilitating installation of the packaged content-based application at the one or more targets. The example method includes managing the content-based application remotely from the one or more targets. In the example method, content is to be created, stored, deployed, and retrieved independently of the creation and deployment of the content-based application consuming data based on the content.

20 Claims, 41 Drawing Sheets

Related U.S. Application Data

(60) Provisional application No. 61/444,961, filed on Feb. 21, 2011.

(51) Int. Cl.
*G16H 40/20* (2018.01)
*G06Q 50/24* (2012.01)
*G16H 10/60* (2018.01)
*G06F 19/00* (2018.01)

(56) References Cited

U.S. PATENT DOCUMENTS

| | | | |
|---|---|---|---|
| 7,933,780 | B2 | 4/2011 | De La Huerga |
| 2002/0010679 | A1 | 1/2002 | Felsher |
| 2004/0167804 | A1 | 8/2004 | Simpson et al. |
| 2004/0260576 | A1 | 12/2004 | Wang et al. |
| 2005/0086072 | A1 | 4/2005 | Fox, Jr. et al. |
| 2006/0106649 | A1 | 5/2006 | Eggers et al. |
| 2007/0273517 | A1 | 11/2007 | Govind |
| 2008/0010092 | A1 | 1/2008 | Smirniotopoulos et al. |
| 2012/0215562 | A1 | 8/2012 | James et al. |
| 2012/0239428 | A1 | 9/2012 | James et al. |

OTHER PUBLICATIONS

Chueh-Loo Poh, et al., "Addressing the Future of Clinical Information System_Web-Based Multilayer Visualization," Transactions on Information Technology in Biomedicine, Los Alamitos, CA, vol. 11, No. 2, Mar. 1, 2007, pp. 127-140.
Jin, et al., "Content and Semantic Context Based Image Retrieval for Medical Image Grid," GRID '07 Proceedings of the 8th IEEE/ACM International Conference on Grid Computing, pp. 105-112, IEEE Computer Society Washington, DC, USA 2007.
International Searching Authority, "Search Report and Written Opinion," issued in connection to PCT Application No. PCT/US2013/026849, dated Jun. 5, 2013 (9 pages).
Stanley M. Huff, Roberto A. Rocha, Bruce E. Bray, Homer R. Warner and Peter J. Haug, "An Event Model of Medical Information Representation," Journal of American Medical Informatics Association 2(2): pp. 116-134, Mar./Apr. 2005.
Stephane Meystre, Peter J. Haug, "Automation of a problem list using natural language processing," BMC Medical Informatics and Decision Making 2005 5:30 (16 pages).
United States Patent and Trademark Office, "Non-Final Office Action," issued in connection with U.S. Appl. No. 13/401,057, dated May 28, 2013 (8 pages).
United States Patent and Trademark Office, "Final Office Action," issued in connection with U.S. Appl. No. 13/401,057, dated Oct. 28, 2013 (12 pages).
United States Patent and Trademark Office, "Non-Final Office Action," issued in connection with U.S. Appl. No. 13/401,057, dated Jun. 19, 2014 (18 pages).
United States Patent and Trademark Office, "Final Office Action," issued in connection with U.S. Appl. No. 13/401,057, dated Nov. 24, 2014 (15 pages).
United States Patent and Trademark Office, "Non-Final Office Action," issued in connection with U.S. Appl. No. 13/401,057, dated Sep. 4, 2015 (13 pages).
United States Patent and Trademark Office, "Final Office Action," issued in connection with U.S. Appl. No. 13/401,057, dated Mar. 1, 2016 (21 pages).
United States Patent and Trademark Office, "Advisory Action," issued in connection with U.S. Appl. No. 13/401,057, dated May 19, 2016 (13 pages).
United States Patent and Trademark Office, "Non-Final Office Action," issued in connection with U.S. Appl. No. 13/401,057, dated Jun. 27, 2016 (29 pages).
United States Patent and Trademark Office, "Final Office Action," issued in connection with U.S. Appl. No. 13/401,057, dated Nov. 21, 2016 (30 pages).
United States Patent and Trademark Office, "Advisory Action," issued in connection with U.S. Appl. No. 13/401,057, dated Feb. 7, 2017 (14 pages).
United States Patent and Trademark Office, "Non-Final Office Action," issued in connection with U.S. Appl. No. 13/401,057, dated May 17, 2017 (31 pages).
United States Patent and Trademark Office, "Notice of Allowance," issued in connection with U.S. Appl. No. 13/401,057, dated Oct. 18, 2017 (11 pages).
United States Patent and Trademark Office, "Non-Final Rejection," issued in connection with U.S. Appl. No. 13/401,266, dated Nov. 6, 2014 (13 pages).
United States Patent and Trademark Office, "Non-Final Rejection," issued in connection with U.S. Appl. No. 13/401,266, dated Jul. 23, 2015 (18 pages).
United States Patent and Trademark Office, "Final Rejection," issued in connection with U.S. Appl. No. 13/401,266, dated Feb. 9, 2016 (18 pages).
United States Patent and Trademark Office, "Advisory Action," issued in connection with U.S. Appl. No. 13/401,266, dated Apr. 22, 2016 (15 pages).
United States Patent and Trademark Office, "Non-Final Rejection," issued in connection with U.S. Appl. No. 13/401,266, dated May 17, 2017 (26 pages).
United States Patent and Trademark Office, "Final Rejection," issued in connection with U.S. Appl. No. 13/401,266, dated Dec. 21, 2017 (24 pages).
International Searching Authority, "International Search Report and Written Opinion," issued in connection with PCT patent application No. PCT/US2013/026849, dated Jun. 5, 2013 (9 pages).
International Bureau, "International Preliminary Report on Patentability," issued in connection with PCT patent application No. PCT/US2013/026849, dated Aug. 26, 2014 (8 pages).

2500

2600

CLINICAL CONTENT-DRIVEN ARCHITECTURE SYSTEMS AND METHODS OF USE

CROSS-REFERENCE TO RELATED APPLICATIONS

This patent claims priority to U.S. Non-Provisional application Ser. No. 13/401,057, entitled "CLINICAL CONTENT-DRIVEN ARCHITECTURE SYSTEMS AND METHODS OF USE,", filed on Feb. 21, 2012, which claims the benefit of priority to Provisional Application Ser. No. 61/444,961, entitled "Clinical Content-Driven Architecture Systems and Methods of Use," which was filed on Feb. 21, 2011, both of which are hereby incorporated by reference in their entireties.

FIELD OF THE DISCLOSURE

The present disclosure relates generally to healthcare information systems and, more particularly, to methods and apparatus for content-driven systems and methods.

BACKGROUND

Healthcare environments, such as hospitals and clinics, typically include information systems (e.g., electronic medical record (EMR) systems, lab information systems, outpatient and inpatient systems, hospital information systems (HIS), radiology information systems (RIS), storage systems, picture archiving and communication systems (PACS), etc.) to manage clinical information such as, for example, patient medical histories, imaging data, test results, diagnosis information, management information, financial information, and/or scheduling information. These healthcare information systems are used to implement different types of workflows in which clinical information is generated, updated, augmented, and/or otherwise processed for one or more purposes.

Figure 1:
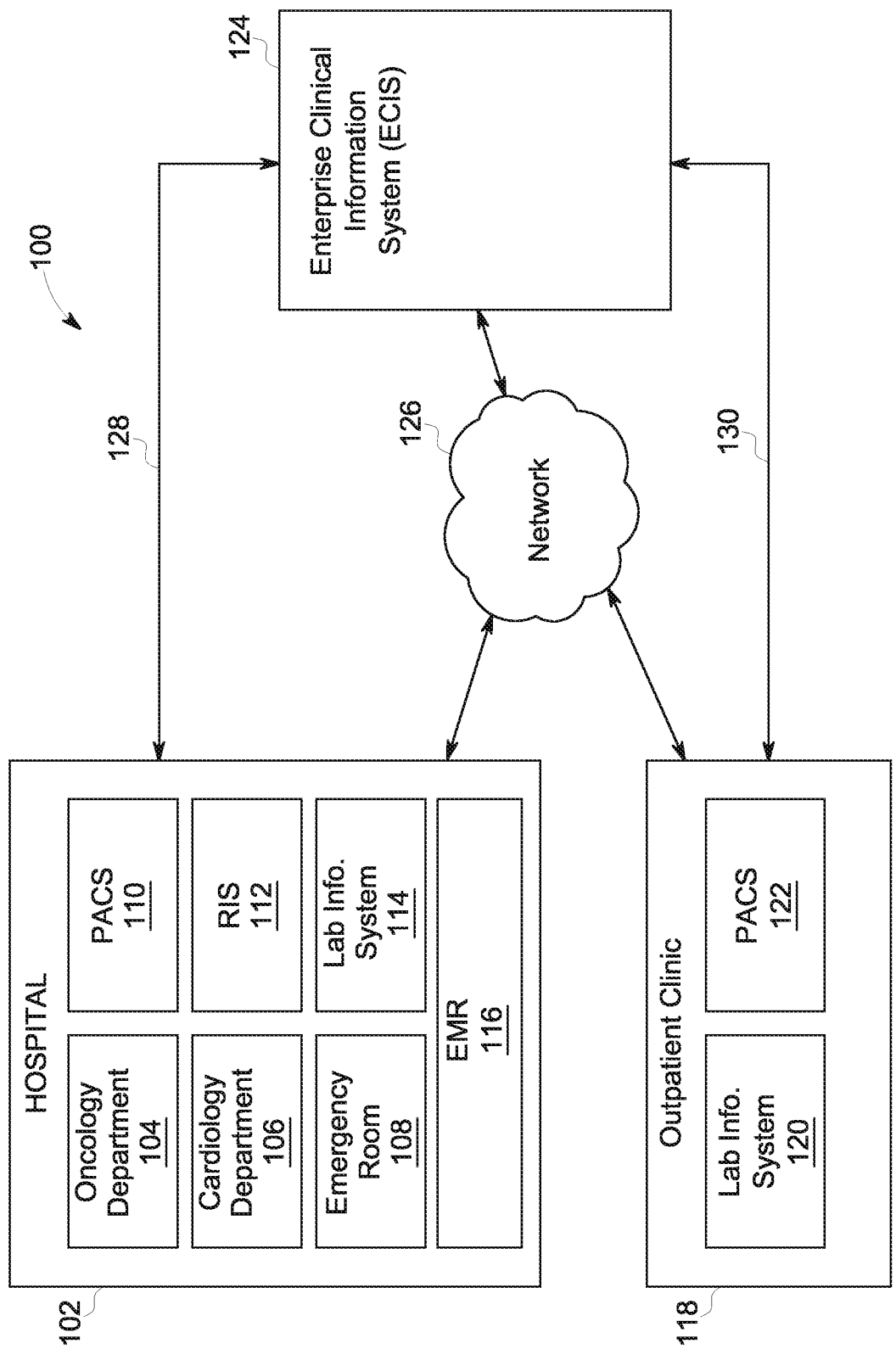
FIG. 1 is a block diagram of an example healthcare environment in which the example methods, apparatus, systems, and/or articles of manufacture disclosed herein for clinical content-based healthcare may be implemented.

The foregoing summary, as well as the following detailed description of certain implementations of the methods, apparatus, systems, and/or articles of manufacture described herein, will be better understood when read in conjunction with the appended drawings. It should be understood, however, that the methods, apparatus, systems, and/or articles of manufacture described herein are not limited to the arrangements and instrumentality shown in the attached drawings.

BRIEF DESCRIPTION

Certain examples provide a method of content-driven clinical information management. The example method includes facilitating, using a processor, authoring of content and combination of the content into a content-based application, wherein content represents a parameterization of instructions to instruct the content-based application how to operate, the content formulated according to one or more detailed clinical models. The example method includes packaging and deploying the content-based application using a processor to one or more targets for installation. The example method includes facilitating installation of the packaged content-based application at the one or more targets. The example method includes managing the content-based application remotely from the one or more targets. In the example method, content is to be created, stored, deployed, and retrieved independently of the creation and deployment of the content-based application consuming data based on the content.

Certain examples provide a tangible computer-readable storage medium including computer program code which, when executed, implements a method of content-driven clinical information management. The example method includes facilitating, using a processor, authoring of content and combination of the content into a content-based application, wherein content represents a parameterization of instructions to instruct the content-based application how to operate, the content formulated according to one or more detailed clinical models. The example method includes packaging and deploying the content-based application using a processor to one or more targets for installation. The example method includes facilitating installation of the packaged content-based application at the one or more targets. The example method includes managing the content-based application remotely from the one or more targets. In the example method, content is to be created, stored, deployed, and retrieved independently of the creation and deployment of the content-based application consuming data based on the content.

DETAILED DESCRIPTION

Although the following discloses example methods, apparatus, systems, and articles of manufacture including, among other components, firmware and/or software executed on hardware, it should be noted that such methods, apparatus, systems, and/or articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

Entities of healthcare enterprises operate according to a plurality of clinical workflows. Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, and/or any other action useful in processing healthcare information. The defined clinical workflows can include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

However, the entities of a healthcare enterprise and/or entities from separate healthcare enterprises sometimes operate within a broader, interdependent information system, which hinder the ability of entities to customize clinical workflows. For example, the information system to which a healthcare entity belongs may place restrictions on changes to workflow applications or programs. Moreover, because some healthcare entities operate using systems, programs, devices, etc. from varying manufacturers, software providers, etc., a lack of interoperability between the systems, programs, devices, etc. of each healthcare entity prohibits many customizations from realization. As a consequence of these example factors as well as additional or alternative factors, healthcare entities that desire customized clinical workflows are typically required to request such customizations from the manufacturers, software providers, etc. Furthermore, for such customizations to implemented or integrated into a healthcare information system, a wide range of system-interrupting updates or re-releases occur within the information systems.

Certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost.

Certain examples facilitate better control over data. For example, certain example systems and methods enable care providers to access real-time patient information from existing healthcare information technology (IT) systems together in one location and compare this information against evidence-based best practices.

Certain examples facilitate better control over process. For example, certain example systems and methods provide condition- and role-specific patient views enable a user to prioritize and coordinate care efforts with an institution's agreed upon practice standards and to more effectively apply resources.

Certain examples facilitate better control over outcomes. For example, certain example systems and methods provide patient dashboards that highlight variations from desired practice standards and enable care providers to identify most critical measures within the context of performance-based care.

Certain examples leverage existing IT investments to standardize and centralize data across an organization. In certain examples, this includes accessing multiple systems from a single location, while allowing greater data consistency across the systems and users.

In certain examples, an advanced Service-Oriented Architecture (SOA) with a modern technology stack helps provide robust interoperability, reliability, and performance. The example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts.

Certain examples provide real-time (or at least substantially real time assuming some system delay) patient data from one or more IT systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

Generally, the example methods, apparatus, systems, and/or articles of manufacture disclosed herein enable healthcare entities of an enterprise clinical information system (ECIS) to dynamically customize one or more clinical workflows. Among other functions and/or benefits, the ECIS supports healthcare practitioners in decision making processes by aggregating healthcare information across disparate enterprises and/or entities thereof and referencing collection(s) of data (e.g., guidelines, recommendations related treatment and/or diagnosis, studies, histories, etc.) to automatically generate supportive information to be communicated to one or more healthcare practitioners related to the aggregated healthcare information. While each entity operates in connection with the ECIS that is administered by a provider thereof, the examples disclosed herein enable each entity of operating in connection with the ECIS to originate and/or modify one or more clinical workflows without relying on the provider of the ECIS to do so on behalf of the entity. In other words, although a healthcare entity is part of the ECIS and exchanges data with and via the ECIS, that entity can independently create and/or manage its clinical workflows using the examples disclosed herein. Furthermore, the examples disclosed herein enable entities of the ECIS to deploy or initiate the customized workflows without having to reboot or significantly interrupt the ECIS and/or the other components, workflows, etc., thereof. The example methods, apparatus, systems, and/or articles of manufacture disclosed herein and the advantages and/or benefits thereof are described in greater detail below in connection with the figures.

FIG. 1 is a block diagram of an example healthcare environment 100 in which the example methods, apparatus, systems, and/or articles of manufacture disclosed herein for clinical content-based healthcare may be implemented. The example healthcare environment 100 of FIG. 1 includes a first hospital 102 having a plurality of entities operating within and/or in association with the first hospital 102. In the illustrated example, the entities of the first hospital 102 include an oncology department 104, a cardiology department 106, an emergency room system 108, a picture archiving and communication system (PACS) 110, a radiology information system (RIS) 112, and a laboratory information system (LIS) 114. The oncology department 104 includes cancer-related healthcare practitioners, staff and the devices or systems that support oncology practices and treatments. Similarly, the cardiology department 106 includes cardiology-related healthcare practitioners, staff and the devices and/or systems that support cardiology practices and treatments. Notably, the example oncology department 104 of FIG. 1 has specifically designed clinical workflows to be executed in response to certain events and/or according to a schedule. At the same time, the example cardiology department 106 of FIG. 1 has specifically designed clinical workflows to be executed in response to certain events and/or according to a schedule that differ from the clinical workflows of the example oncology department 104 of FIG. 1. For example, the oncology department 104 may execute a first set of actions in response to receiving a Healthcare Level 7 (HL7) admission-discharge-transfer (ADT) message, while the cardiology department 106 executes a second set of actions different from the first set of actions in response to receiving a HL7 ADT message. Such differences may also exist between the emergency room 108, the PACS 110, the RIS 112 and/or the accounting services 114.

Briefly, the emergency room system 108 manages information related to the emergency care of patients presenting at an emergency room of the hospital 102, such as admission information, observations from emergency examinations of patients, treatments provided in the emergency room setting, etc. The PACS 110 stores medical images (e.g., x-rays, scans, three-dimensional renderings, etc.) as, for example, digital images in a database or registry. Images are stored in the PACS 110 by healthcare practitioners (e.g., imaging technicians, physicians, radiologists) after a medical imaging of a patient and/or are automatically transmitted from medical imaging devices to the PACS 110 for storage. The RIS 112 stores data related to radiology practices such as, for example, radiology reports, messages, warnings, alerts, patient scheduling information, patient demographic data, patient tracking information, and/or physician and patient status monitors, as well as enables exam order entry (e.g., ordering an x-ray of a patient) and image and film tracking (e.g., tracking identities of one or more people that have checked out a film). The lab information system 114 stores clinical information such as lab results, test scheduling information, corresponding practitioner(s), and/or other information related to the operation(s) of one or more labs at the corresponding healthcare facility. While example types of information are described above as being stored in certain elements of the hospital 102, different types of healthcare data may be stored in one or more of the entities 104-114, as the entities 104-114 and the information listed above is included herein as non-limiting examples. Further, the information stored in entities 104-114 may overlap and/or be combined into one or more of the entities 104-114. Each of the example entities 104-114 of FIG. 1 interacts with an electronic medical record (EMR) system 116. Generally, the EMR 116 stores electronic copies of healthcare records associated with, for example, the hospital 102 and the entities 104-114 thereof.

The example healthcare environment 100 of FIG. 1 also includes an outpatient clinic 118 as an example of another healthcare enterprise. The example outpatient clinic 118 of FIG. 1 includes a lab information system 120 and a PACS 122 that operate similarly to the corresponding entities of the example hospital 102. The lab information system 120 and the PACS 122 of the example outpatient clinic 118 operate according to specifically designed clinical workflows that differ between each other and the clinical workflows of the entities 104-114 of the hospital 102. Thus, differences in clinical workflows can exist between the entities of a healthcare enterprise and between healthcare enterprises in general.

In the illustrated example of FIG. 1, the hospital 102 and the outpatient clinic 118 are in communication with an ECIS 124 via a network 126, which may be implemented by, for example, a wireless or wired Wide Area Network (WAN) such as a private network or the Internet, an intranet, a virtual private network, a wired or wireless Local Area Network, etc. More generally, any of the coupling(s) described herein may be via a network. Additionally or alternatively, the example hospital 102 and/or the example outpatient clinic 118 are in communication with the example ECIS 124 via direct or dedicated transmission mediums 128 and 130.

Generally, the ECIS 124 supports healthcare information processing implemented by systems, devices, applications, etc. of healthcare enterprises, such as the hospital 102 and the outpatient clinic 118. The ECIS 124 is capable of processing healthcare messages from different entities of healthcare enterprises (e.g., the entities 104-114 of the hospital 102) that may generate, process and/or transmit the healthcare messages differently and/or using different formats, protocols, policies, terminology, etc. when generating, processing, and/or transmitting the healthcare messages. Moreover, the example ECIS 124 of FIG. 1 supports healthcare practitioners in decision making processes by aggregating healthcare information across disparate enterprises and/or entities thereof and referencing collection(s) of data to automatically generate suggestive and/or definitive data for communication to one or more healthcare practitioners related to the aggregated healthcare information.

Certain examples provide a library of standardized clinical content and proven best practices. Over time, this "library" of content may expand as healthcare organizations add to their own content modules. Because the content is standardized it can be shared and leveraged among organizations using the library and associated clinical knowledge platform. The library and platform help enable organizations to share best practice content. Thus, certain examples provide a clinical knowledge platform that enables healthcare delivery organizations to improve performance against their quality targets.

In certain examples, a quality dashboard application enables creation of one or more dashboards based on the data/content most relevant to an organization at a given period of time. A clinical knowledge platform brings together real-time patient data from existing IT systems within an organization and allows for the comparison of this data against evidence-based best practices. The example quality dashboard application leverages the platform to enable personalized "Quality Dashboards" to be created for specific sets of patients, based on condition, role, and/or other criteria. Variations from desired practice will be highlighted on each dashboard, enabling care providers to ensure better clinical outcomes and enrich patient care.

Figure 2:
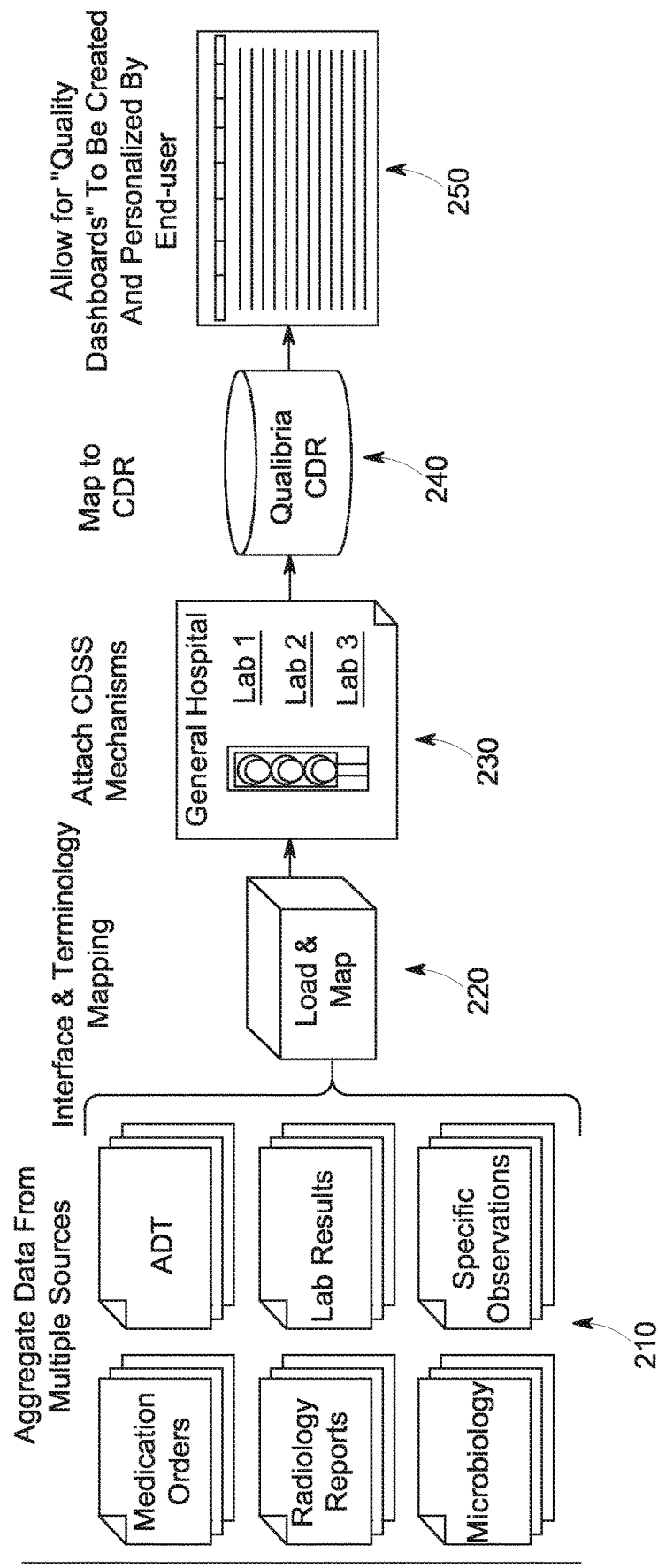
FIG. 2 illustrates an example clinical knowledge system providing an aggregation of data from multiple sources.

In this example, the clinical knowledge platform aggregates data from an organization's existing IT solutions. These can be solutions from the same and/or different manufacturer and/or provider. For example, as long as there is an HL7 or Web Services feed, the clinical knowledge platform can utilize the data from an existing solution. The existing IT solution(s) will continue to operate as they always have, and an organization can continue to use these solutions separate from the clinical knowledge platform if they so desire. However, the clinical knowledge platform and associated application(s) and/or workflow(s) can help to put organizations in greater control of their data by aggregating as much data from disparate IT solutions as possible. FIG. 2 illustrates an example clinical knowledge system 200 providing an aggregation 210 of data from multiple sources. Aggregated data may include, for example, medication orders, radiology reports, microbiology, admit/discharge/transfer (ADT) message, lab results, specific observations, electronic medical record (EMR) data, etc.

As the different data sources are pulled into a central data repository, content standardization occurs. It is this "standardization" that enables content from different IT sources to be used together. For example, as shown in FIG. 2, an interface 220 provides terminology mapping and standardization to the aggregated data.

After the content is standardized, clinical decision support mechanisms can be tied to the content (as illustrated, for example, by the clinical decision support 230 of the system 200 of FIG. 2). The data and associated clinical decision support are then stored in a clinical data repository (CDR), such as CDR 240 of the example system 200. By combining the aggregated and standardized data with clinical decision support rules and alerts, the clinical knowledge platform may provide end-users with an understanding of important elements to which they should pay attention (and take action on) within the larger set of data they are considering when caring for a patient.

Combined data and clinical decision support mechanisms create valuable content that, when arranged properly, may be used to improve the quality of care provided. Organizations can elect to use the application(s) that are provided as a part of the example clinical knowledge platform and/or may choose to build their own clinical application(s) on the platform. The open architecture nature of the platform empowers organizations to build their own vision, rather than base their vision on the static/hard coded nature of traditional IT solutions.

In certain examples, "Quality Dashboards" created via an example application display data via columns and rows in addition to individual patient "inspector" views. For example, the system 200 shown in FIG. 2 provides one or quality dashboards 250 to be created and personalized by an end user. The flexible nature of this dashboard application empowers organizations to create dashboards of the aggregated data based on their needs at a given period of time. The organization may determine what data elements they would like to include on each dashboard and, without significant IT resources, create a dashboard that reflects their vision. In addition, organizations can determine where on the dashboard they would like the information to be displayed and further adjust the view of the content via features such as "bolding" font, etc. When data is added to each dashboard, clinical decision support mechanisms attached to this data are displayed on the dashboard as well. For example, content related to treating a patient based on a particular use case may be included on a quality dashboard, along with alerts and notifications to indicate to end-users when desired outcomes are varying from defined clinical standards. Thus, organizations can create dashboards based on their own idea of "best practice" care for a given disease state.

In certain examples, since combined content and best practices have been standardized, content from one organization using the clinical knowledge platform may be easily shared with other organizations utilizing the platform. In addition, because the content within platform-related applications is standardized in the same manner, upgrades/updates to the example platform can occur efficiently across organizations. That represents a dramatic change from prior IT solutions which require unique IT upgrades because they are usually uniquely customized to each organization in which they are installed.

Generally, content is information and experience that may provide value for an audience. Any medium, such as the Internet, television, and audio CDs, may deliver content as value-adding components. To analogize to consumer media to illustrate an example relationship, content represents the deliverable, such as a DVD movie, as opposed to the delivery mechanism, a DVD player. As long as content conforms to the media standard, any compatible device can play it.

Content, as used herein, is the externalization or parameterization of "the instructions" that tell applications how to work. For example, content is a collection of externalized information that tells software, in conjunction with data, how to behave. In certain examples, a clinical knowledge platform takes in and executes content against data to render applications visually and behaviorally.

Content includes data read and interpreted by a program to define or modify presentation, behavior, and/or semantics of the program and/or of application data consumed by the program, for example. Content includes documents presented to a client by a program without modification, for example. Content may be created, stored, deployed, and/or retrieved independently of the creation and deployment of the program(s) consuming the data, for example. Content may be versionable to capture desired variation in program behavior and/or semantics, for example.

Classes of content may include configuration content, preferences content, reference content, application content, etc. Content types may combine behaviors of two or more classes, for example.

Software vendors take many different approaches to customization. At one extreme, some vendors write different software for each customer or allow customers to write software. At the other extreme, a vendor has the same software for each customer, and all customization occurs through creating or modifying content. In certain examples, the same software may be used for each customer, and customization is handled through content.

In healthcare, new laboratory tests, medications, and even diseases are constantly being discovered and introduced. Structuring this as content, where underlying software does not need to change, helps accommodate and use updated information.

In certain examples, many different content types, such as form definitions, data models, database schema, etc., are accommodated. In certain examples, each content type may be used differently and involve a distinct authoring tool. Thus, in certain examples, content may refer to "a collection of the content instances for all content types," also called a content repository, knowledge repository, or knowledge assets. For example, a content instance is a specific member of a content type, such as a heart rate data model.

In certain examples, each content type is associated with a generic, extensible structure that content instances of the content type follows. An example clinical information system can specify content in an abstract way that does not presuppose a particular software implementation, for example. That is, another system, such as GE's Centricity® Enterprise, may consume content from a knowledge repository, apply a different set of software, and achieve the same behaviors. Additionally, an abstract content definition can more easily transition to a new system. If one can extract content from a legacy system, a knowledge repository may be able to import and reuse it. Such a capability helps reduce a large barrier to change for potential customers.

Content can change with time. In an example, a current knowledge repository can handle any "old" data entered into a system under the auspices of an older knowledge repository. Occasionally, a question may arise where someone could ask, "What did Dr. Smith see at some past time?" Under these circumstances, a current definition of a particular display may not correctly reflect the situation at the time. An example CIS, unlike other systems, can bring back the old form for visualizing the data since all knowledge assets are versioned and retained.

Content may need to vary for different circumstances. For example, an MPV may differ between emergency department (ED) and labor and delivery settings. Each MPV has rows and columns of data specific to its setting. Context refers to being aware of and reacting distinctively to a location and other situational differences. For example, interpretation of a patient's low temperature can vary based on location. If it occurs in the recovery room after cardiopulmonary bypass with deliberate patient cooling, it means one thing. If the patient is in the ED after breaking through ice into a lake, it means something completely different. Context may vary based on user location, patient location, user role, and/or various other factors. In certain examples, content may be applied based on context.

Globalization is a process of adapting software so that it has no language references, before embedding capabilities to make it suitable for particular languages, regions, or countries. Having globalized it, a CIS may then translate it to other languages and cultures, called localization. Globalizing a software product involves creating content separate from the software. For example, embedded text (e.g., user messages), sort orders, radix characters, units of measure, data formats, currency, etc., may be removed and parameterized. References to languages, character sets, and fonts may also be removed, for example. In certain examples, while display representations may be local, terminology concepts are applied universally, making a rule, calculation, or other content based on one or more terminology concepts useable worldwide without modification.

Figure 3:
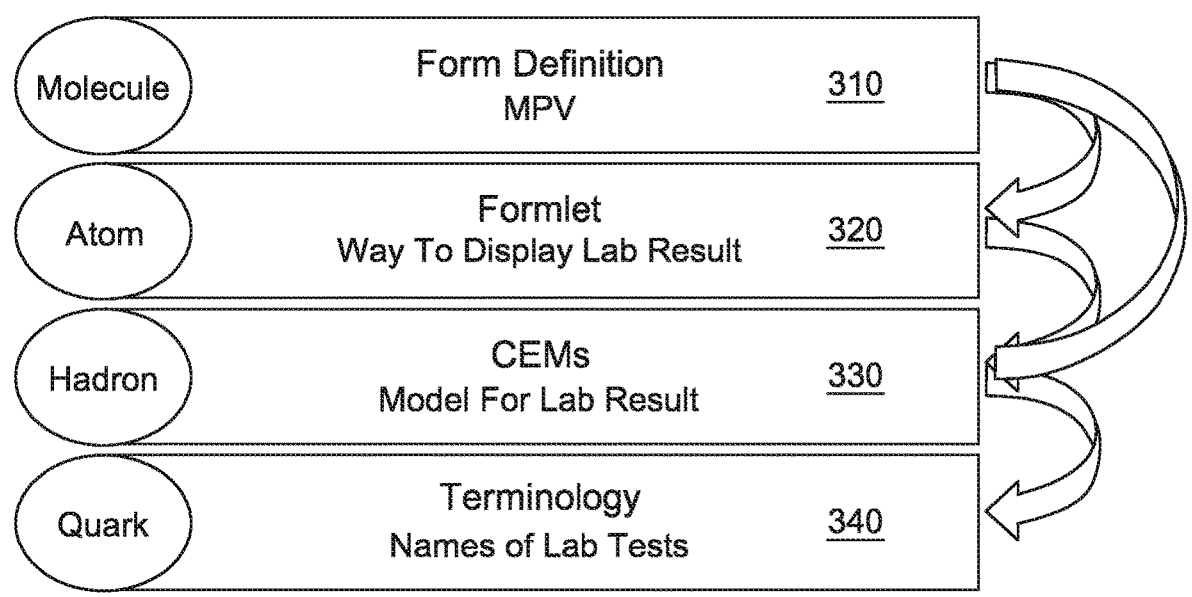
FIG. 3 illustrates an example interdependence of content types.

For example, FIG. 3 illustrates an example interdependence of content types. As shown in the example of FIG. 3, content is a set of interdependent building blocks. Content may be thought of as a hierarchy, with terminology 310 (e.g., names of lab tests) as a lowest level. Terminology 310 may be common and coded across a customer base. Clinical element models (CEMs) 320 govern structure and content of objects stored in a database and used by applications. A formlet 330 provides a way to display a particular content item (e.g., a way to display a particular lab result). A form definition 340 provides an application or view (e.g., a dashboard) of a collection of formlets (e.g., a multi-patient view (MPV) showing one or more lab results and/or other information). For example, if a particular MPV definition is moved from one customer to another, the MPV definition along with other content items on which the form definition depends are imported into the new customer's knowledge repository. Content items may include appropriate formlets, CEMs, and terminology, for example.

In certain examples, a detailed clinical model defines, at a granular level, the structure and content of a data element. For example, the detailed Clinical Model for "Heart Rate Measurement" dictates the data type of a heart rate measurement, and the valid physiologic range of a heart rate. It says that a "body location" is valid qualifying information about a heart rate measurement, but a "color" is not. It further decrees that the valid values for "body location" are terminology codes found in the "heart rate body location" value set. Moreover, it prescribes that a "resting heart rate" is an instance of "Heart Rate Measurement" where the value of "temporal context" is "resting", where "resting" is also a coded value. A detailed clinical model pulls the information together into a single, explicit, and computable form. The detailed clinical models or clinical element models (CEMs) govern the content and structure of all data objects stored in an example clinical database and used by applications, for example. In addition, CEMs are extensible, such that content authors may add new CEMs or attributes to existing CEMs without requiring major changes to database structures or software, for example.

In certain examples, shared or portable content is, in effect, "plug 'n play". System administrators can add it (e.g., plug it into) to a system without any software changes, and the content behaves in the intended way and does not cause errors. The size or scope of shared content can range from a single term to an entire knowledge repository, for example. Shared content fundamentally changes an implementation paradigm and reduces a total system cost of ownership, for example.

Customers can change shared content. Customers can improve it or make it more suitable for their institutions. When customers do this, they leave the original definition intact, but clone it and keep their changed version in their "local" space, for example.

As described above, classes of content may include configuration content, preferences content, reference content, application content, etc. Configuration content is content that is modified infrequently and is concerned primarily with system behavior, for example. Examples of configuration content may include internet protocol (IP) address and port of clinical knowledge database, identifiers of terminals in systems, security access privileges, configuration files, etc. Configuration content may affect program semantics, for example. Configuration content is generally modified by system administrators and is often stored in the file system, for example.

Preference content is modified frequently and is concerned primarily with variation between users. Examples of preference content include display colors and fonts, default search parameters, screen layout, etc. Preference content rarely affects program semantics and is most commonly modified by individual users. While modified by users, the system generally distributes initial or default preference content.

In certain examples, distributed or default preference content behaves very similar to application content before modification by a user. Preference content may be context sensitive, transformed at deployment, etc. Preference content may include vocabulary concepts and pick-lists that are resolved when loading and retrieving just like other content types.

Reference content is documents that are presented without modification as part of the application. Reference content is often stored in formats that are opaque to a program (e.g., as a PDF, a Microsoft Word™ document, etc.). Reference content is generally not specific to or customized for a specific patient (e.g., instruction sheets, information sheets, policies and procedures, etc.). Reference content may be independent of program semantics and behavior. Reference content may be authored independently of a program. While not an element of a content drive system per se, reference content is often managed as content by a clinical knowledge system. Once reference content is modified for presentation to a specific user, the content starts behaving much more like patient data/documents. Reference content with the structure to enable modification starts behaving much more like application content.

Application content may be modified frequently or infrequently depending on use. Application content may be concerned primarily with application behavior and semantics. Applicant content may be generally specific to an application domain. Examples may include a flow sheet template, clinical element models, terminology, document templates that are modified and stored as patient data (e.g., hot text), etc. Terminology is application content but has behaviors distinct from other application content types and is managed (largely) independently of other application content, for example. Application data often affects program semantics and behavior. Application content may be authored at multiple levels in an organization or external to the organization, for example.

Application content may be implemented as a custom markup language, for example. Application content may be implemented as a domain specific language (DSL), for example. For example, data queries may be implemented using a frame definition language (FDL). Clinical element models may be implemented using a constraint definition language (CDL). Application content may be directly authored or imported as data into a content store (e.g., concepts in a vocabulary server), for example.

In certain examples, while patient data is transactional and often includes discrete data elements, application content is often structured, complex objects and often has associated metadata. In certain examples, metadata is data used to manage content, such as content identifier, version, name of author, access privilege, encryption certificate, etc. Metadata is not treated as content, for example. While patient data is owned by a patient and is part of a legal record, application content is not owned by a patient and is not part of a legal record. Application content may be published (e.g., is not transactional) and managed using a lifecycle.

Certain examples provide content-driven systems and processes that rely primarily on content to determine application behavior. An example system includes a reference platform that consumes, interprets, and/or executes content while remaining application neutral. An example system uses content that remains independent of an implementation of the reference platform to allow independent evolution of the platform and the application.

Figure 4:
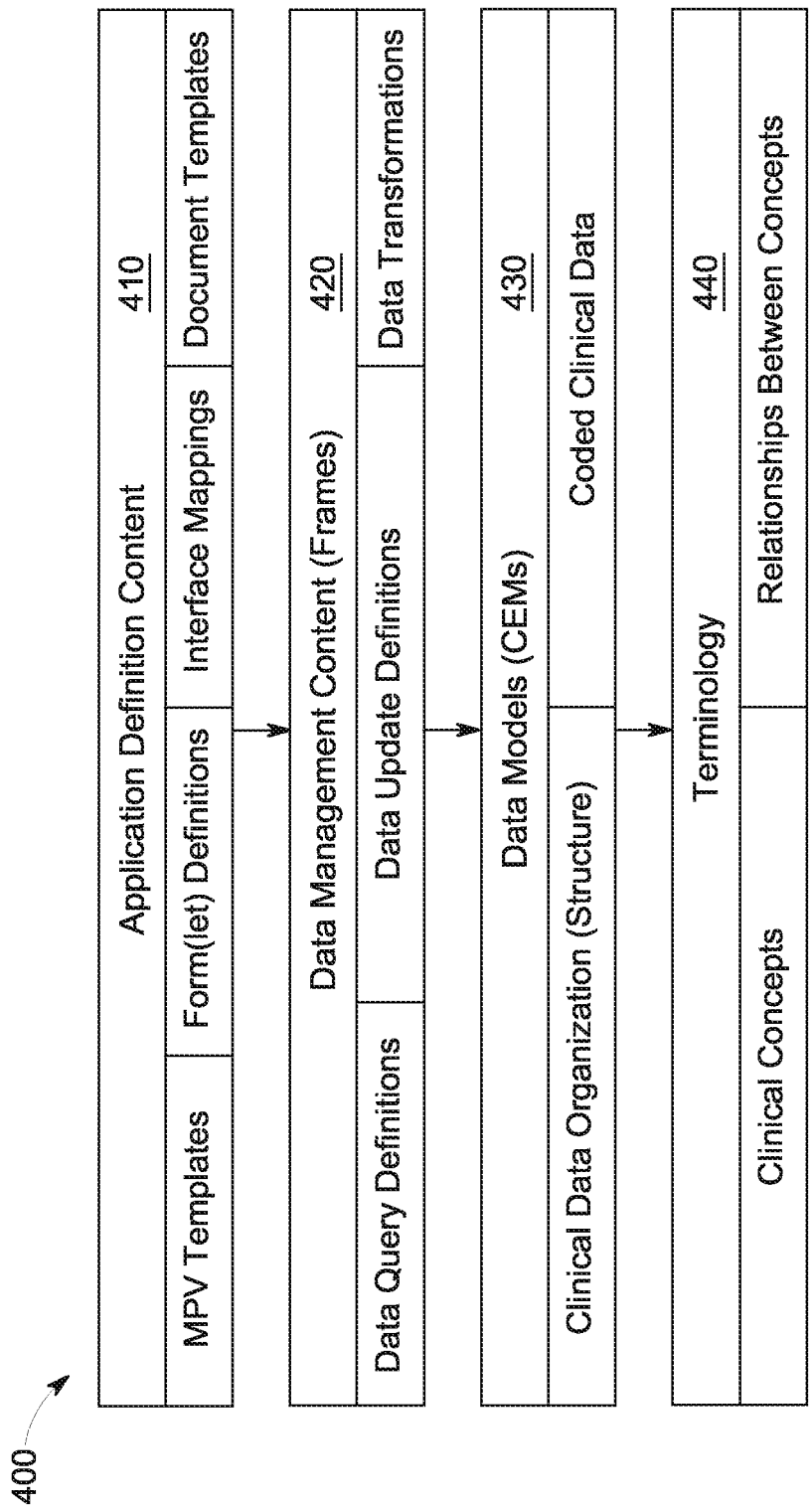
FIG. 4 illustrates an example hierarchy of content, associated data models, and terminology.

FIG. 4 illustrates an example hierarchy 400 of content, associated data models, and terminology. In certain examples, once one chooses content based data models, content-based queries and data management are also selected. Content based applications are also chosen. An integral terminology basis includes semantics of data defined in terminology content, for example. As shown in the example of FIG. 4, application definition content 410 (e.g., MPV templates, form(let) definitions, interface mappings, and/or document templates, etc.) relies on data management content (e.g., frames) 420 (e.g., data query definitions, data update definitions, and/or data transformations, etc.). The data management content 420 leverages data models (e.g., CEMs) 430, such as clinical data organization (e.g., structure) and/or coded clinical data, etc. The data models 430 are constructed based on a terminology 440 including clinical concepts and relationships between concepts, for example.

In certain examples, context refers to metadata attributes and/or labels that differentiate variations of a content item. For example, each variant of content item may be referred to as a context variant. Each variation of a content item has a specific set of context attributes (e.g., language, location, role, etc.). An algorithm or heuristic may select a desired variant when retrieving based on a current user's "context." This process may be referred to as context resolution.

Searching refers to examining the content item and/or associated metadata for matches independent of context. Searching can include context attributes to filter for specific context variants in the search. The difference is that a specific variant is not selected algorithmically or heuristically by the content system when searching. Using the "user" as a context attribute is one way to associate a content item with a specific user; similarly provider as a context variable could be used to associate an item with a group of users. Resolving context generally requires some heuristic to resolve ambiguity or conflicts among context variants (e.g., weighting or priority schemes, default rules, etc.). This leads to some ambiguity since changing/adding a context variant or changing the weights of context attribute may change the context resolution on another item in not always obvious ways (at least to a user).

In certain examples, a content item includes:

1. A root content item represented by a universally unique identifier (UUID). The root content item includes metadata only; no actual content is stored.

2. One or more context variants that represent variations of an implementation of the content item in different client contexts occur as children of the root content item.

3. Context variants may form trees of increasing context specialization (e.g., a context variant may have child variants).

4. Each context variant has a unique UUID as well as a relation to the root content item.

5. Each context variant maintains versions of that variant as changes are applied to the variant.

Figure 5:
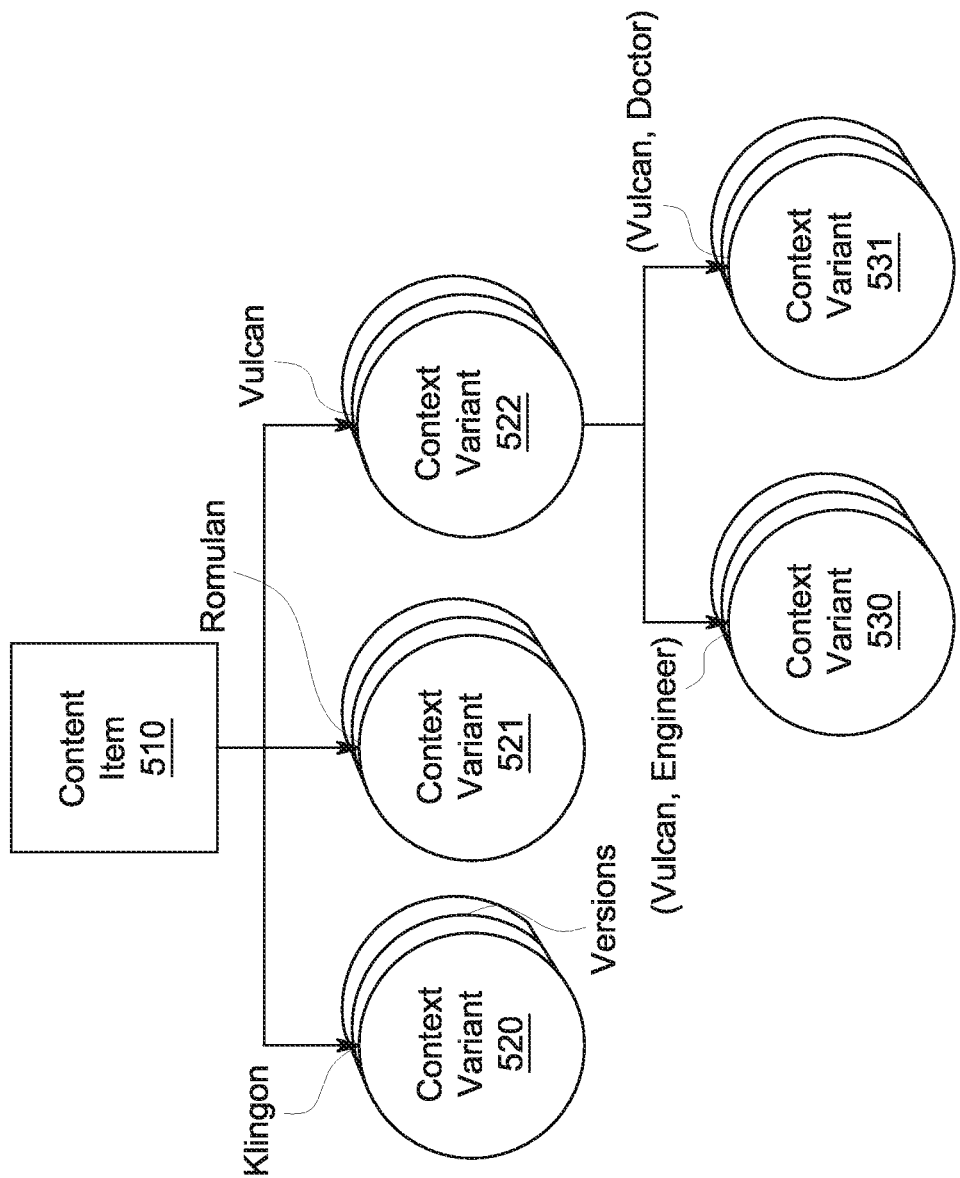
FIG. 5 shows an example root content item having one or more content variants which may be associated with one or more context variants.

As shown in the example of FIG. 5, a root content item 510 has one or more content variants 520-522. Each content variant 520-522 may be associated with one or more context variants 530-531.

Figure 6:
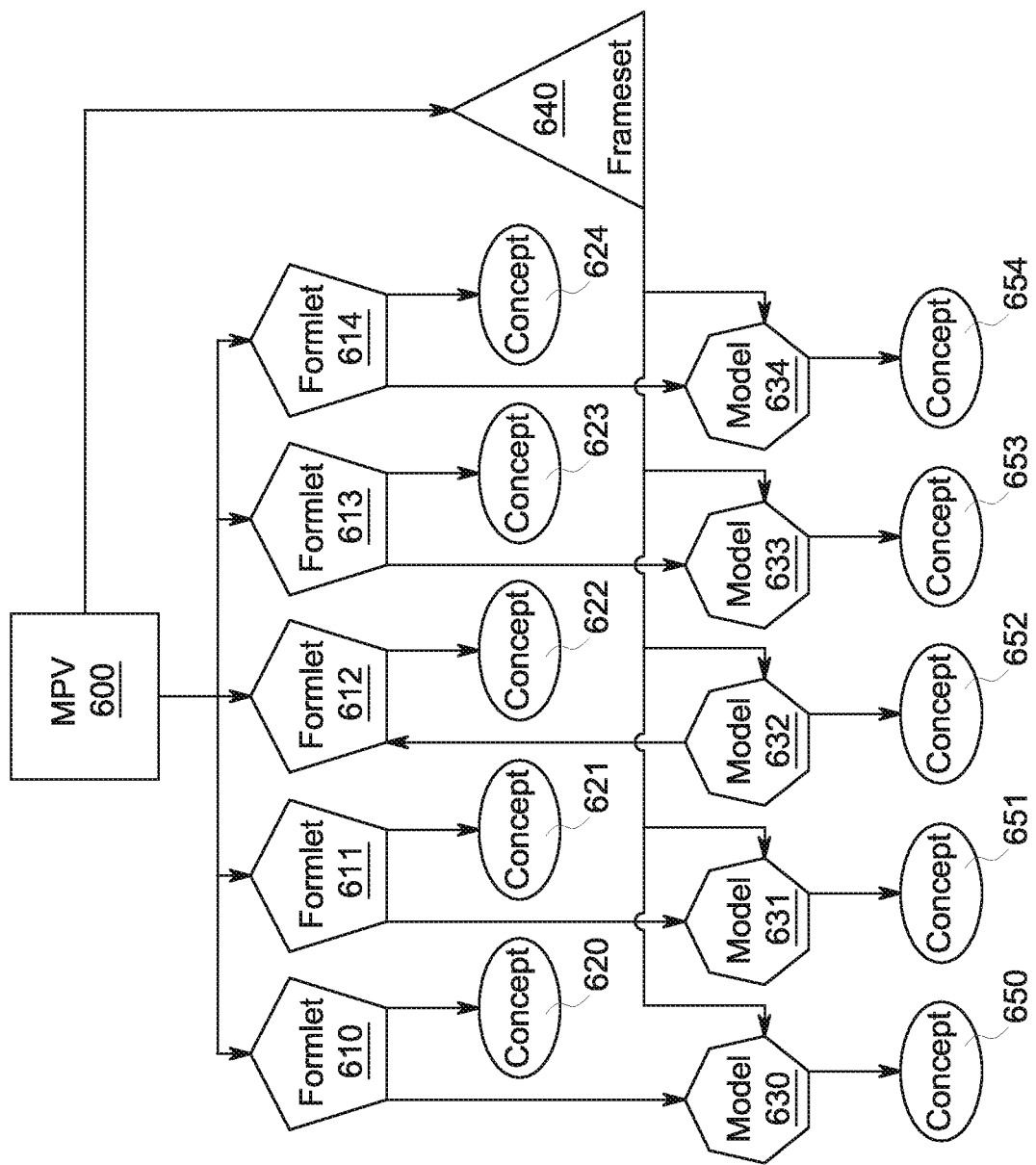
FIG. 6 provides an example multi-patient view (MPV) including a plurality of formlets and a frameset.

FIG. 6 provides an example multi-patient view (MPV) 600 made up of a plurality of formlets 610-614 and a frameset 640. Each formlet 610-614 corresponds to a concept 620-624 and a model 630-634. The frameset 640 is also associated with each model 630-634, and each model 630-634 is associated with a concept 650-654, for example.

In certain examples, content may be stored in multiple content stores. For example, content may be stored in an ECIS database, an XDS repository, a third-party system, etc. Content documents in storage may be identified by a URI that specifies the content store and the key of that item in that content store. A content directory including the content metadata may be searched to obtain the URI for retrieval of the content item. A content type manager may specialize the search, storage, and/or retrieval of items of that content type, for example.

A content item in the content directory is keyed via a UUID for the item. That UUID is not necessarily part of the uniform resource indicator (URI) that defines the storage location.

In certain examples, content items may be organized as a content type. A content type is a set of content items that are defined and managed using common definitions and methodologies (e.g., terminology, clinical element models, frameset definitions, etc.). Content types may have different behaviors, states, lifecycles, etc. Each content type may be managed by a specific content type manager, which is treated as a plug-in to a clinical knowledge platform and/or associated clinical information system, for example. Content types may be added by creating a new content type manager, for example.

Content type managers may interact with a content management framework by implementing a set of event handlers (e.g., package, deploy, retrieve, etc.). "Generic" content types (e.g., content types with no special behavior) may use a default content type manager. An owner of a content type is responsible for implementing an associated content type manager, for example.

In certain examples, during authoring (that is, before deployment), dependencies exist between content items. At runtime (that is, after deployment), dependencies exist between deployed forms of context variants. Dependents that exist during authoring may or may not continue after deployment. For example, terminology description and pick-list resolution are translations during loading and retrieving, not dependencies per se.

In certain examples, at runtime, dependencies are between deployed forms of context variants, not the context variants themselves. The deployed form of a context variant is a "content frame". At deployment time, it may be necessary to guarantee that the packages (e.g., terminology) that a package depends on are also deployed. Terminology dependencies may be inferred from terminology relationships and mappings and do not need to be explicitly tracked.

In certain examples, a content based system provides a capability to distribute content and content updates to external instances (e.g., test systems, quality assurance systems, customer installations, content patches (e.g., SPRS), etc.). An example distribution system provides a capability to distribute content items and associated dependent content items and/or insure that those content items already exist in the target system. For example, an FDL content item must have access to the clinical element types it references in order to process a frame query. The example distribution system may also facilitate an undo or reversal of installed content items that generate issues. Content may be distributed as large sets of items (e.g., during installation) and/or as individual items (e.g., bug fixes), for example.

Figure 7:
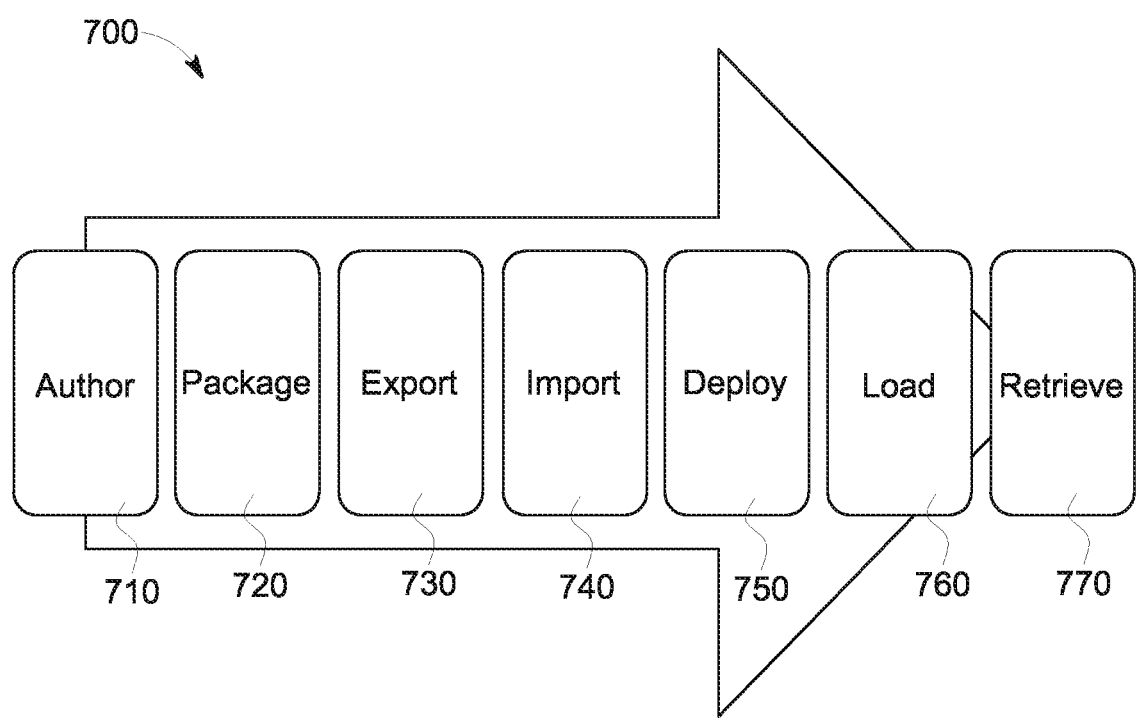
FIG. 7 illustrates an example content management process.

FIG. 7 illustrates an example content management process 700. The example process 700 includes authoring 710, packaging 720, exporting 730, importing 740, deploying 750, loading 760, and retrieving 770.

Authoring 710 includes a process of creating and/or modifying a content item. Authoring may be done by an author composing content directly using an editor (e.g., CDL, FLD, etc.), for example. Authoring may be done using tools (e.g., editor(s), etc.) that are specific to a content-type (e.g., terminology), for example. Authoring may be done by tools within the application(s) consuming a content type (e.g., MPV, forms, etc.), for example. Authoring may be done by applications generating a content item (e.g., MPV generating FDL), for example. In certain examples, there is no single authoring environment for content; rather, there is a family of authoring tools that is often content type specific.

Packaging 720 includes combining all content items and (applicable) context variants within a transitive closure of dependency graphs of one or more content items into a package, for example. Packages may include multiple independent top level content items, for example. Packages may have dependency(-ies) on other package(s). For example, a package containing a frameset content item may dependent on a separate terminology package as a prerequisite to deployment.

Packages may very frequently contain multiple independent, top level items each with its associated dependency graph. A package may not include all context variants of an item. For example, packaging may filter based on context to form a package. Packaging events may include an event to allow a content type manager to specify dependencies of an item being packaged.

Packages may have dependencies on content types other than content packages. For example, a terminology package is a different content type than a content package. Content items within a package may not have explicit dependencies on terminology concepts. Rather, the package has dependencies on the appropriate terminology packages.

In certain examples, packages are used as a distribution mechanism. Packages may be deployed before items in the package are available to a runtime system, for example. Packages themselves may be treated as content items. Thus, packages can themselves be packaged (e.g., packages of packages), and packages may be dependent on other packages. In certain examples, packages may belong a namespace or domain. For example, packages may only include items from a single namespace. Packages may have dependencies on packages in another namespace, for example.

Package(s) may be exported 730 from one system and imported 740 into another. Exported packages may be used to distribute content, for example. System management tool(s) may be provided to create, export, import, and deploy content packages, for example.

Figure 8A:
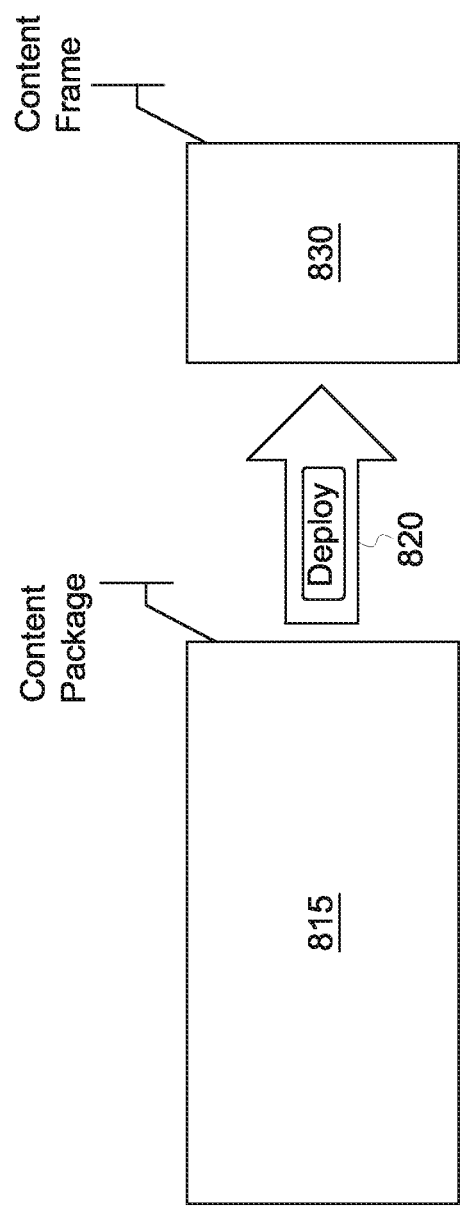
FIG. 8, consisting of FIGS. 8a-8c, shows a deployment example in which a plurality of models in a content package are deployed to create a content frame.
Figure 8B:
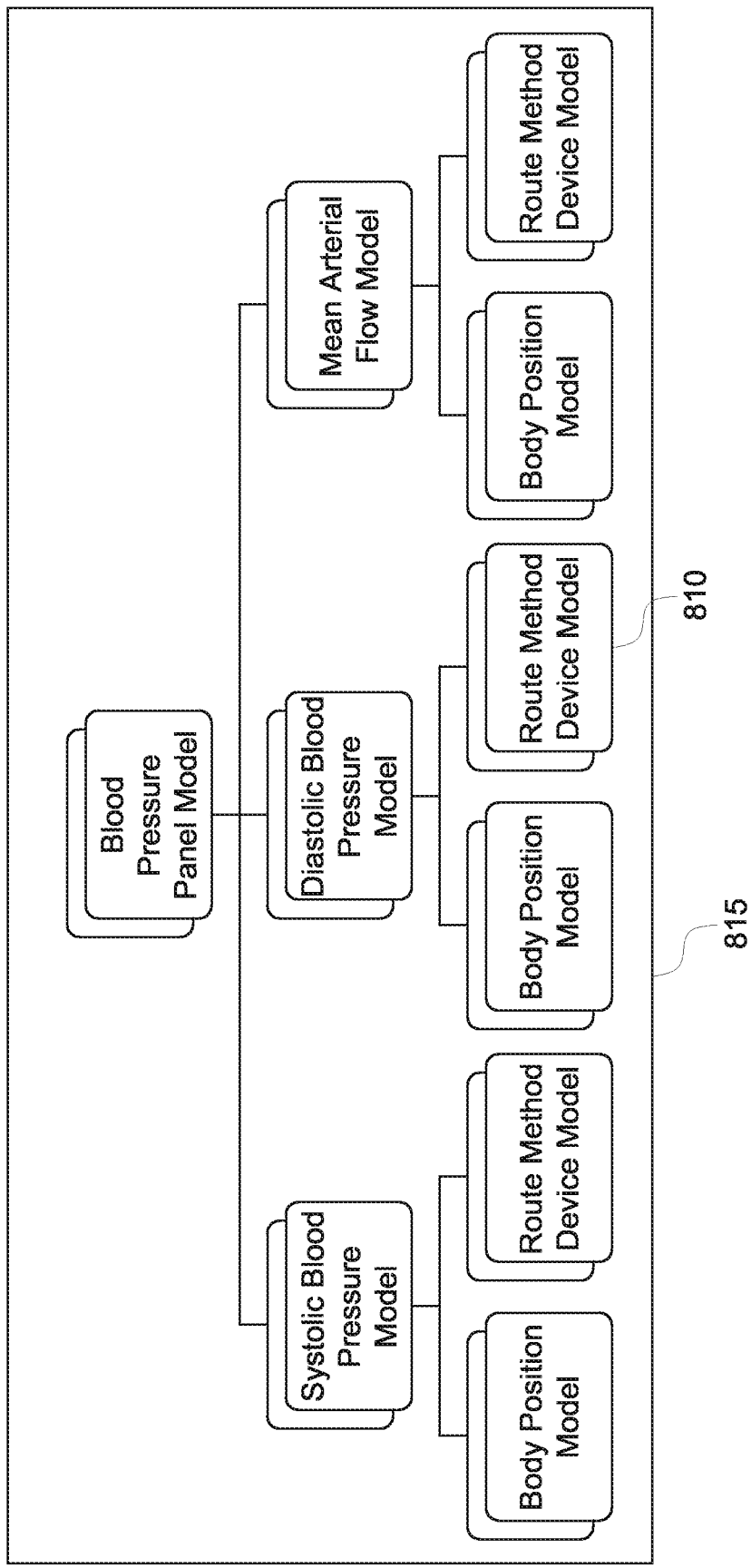
Figure 8C:
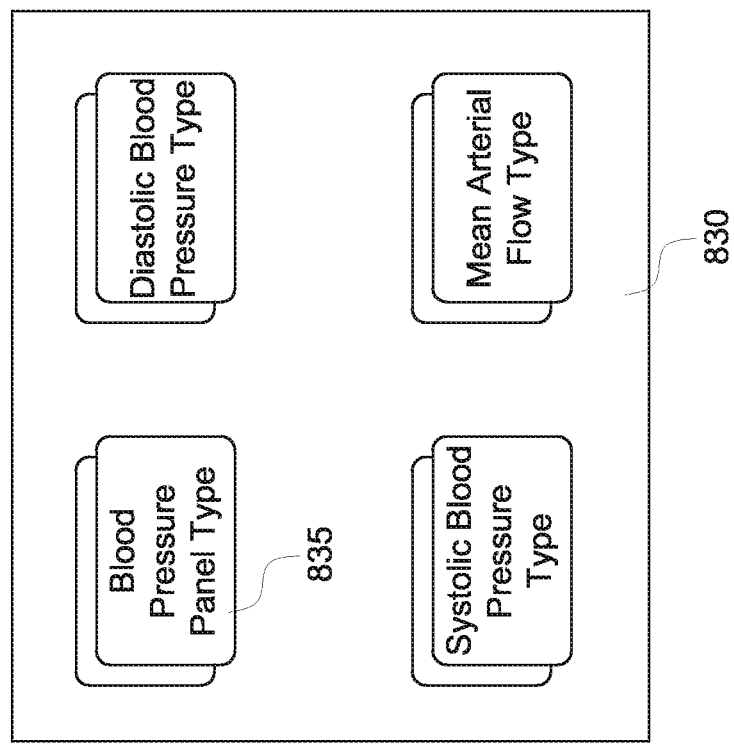

Deploying 750 includes making content items included within a package available to a running system. A content item may be transforming during deployment, for example. For example, constraint definition language (CDL) models may be compiled and may create multiple type objects each with an associated schema. As shown in the deployment example of FIG. 8, a plurality of models 810 in a content package 815 are deployed 820 to create a content frame 830 including plurality of type objects 835 with associated XML schema.

In certain examples, each top level content item in a package being deployed is deployed independently. A deployed content item is logically (and often physically) a different object than the content item being deployed. For example, a deployed content item has independent state and lifecycle. Multiple content items may be created during deployment, for example. For example, deploying a CDL model may generate a CE type object and an XML schema. In certain examples, a source content item may not exist in the runtime system. For example, the source CDL models are not employed, and the generated CE type object is deployed. Deployment of a package may be done manually and/or implicitly by an authoring tool, for example. For example, system administrators may wish to explicitly control deployment of data models but MPVs authored by a user may be implicitly and immediately deployed.

In certain examples, each deployed content item is bundled with all of the content items that are used to execute and/or consume the item. The bundle is referred to as a content frame 830. A content frame 830 is analogous to an archive file manifest. It may not (necessarily) contain the actual content items. The content frame 830 may not include all of the items generated during deployment. For example, the CDL schemas may not be part of the frame.

A content frame 830 is also analogous to a context variant. The frame has its own unique identifier but may be retrieved using the identifier of the root content item the frame is based upon in the same way that context variants are retrieved. Deployment events may include an event to allow the content type manager to specify dependencies of the deployed item(s) within the content frame, for example.

In certain examples, context resolution refers to conditioning selection, composition, and/or behavior of a content item based on a context of a user. Context resolution may occur at one or more levels. For example, context resolution may occur on selection of the content item(s) that a content item being deployed is dependent upon based on context. Such resolution occurs during deployment, and content frames are context specific with dependencies resolved. Context resolution may occur on selection of a content frame based on context when the content frame is retrieved by an application, for example. Context resolution may occur on translation of a content item based on context when loading and/or retrieving a content frame, for example. For example, context resolution may occur upon retrieval of terminology concept designations and/or retrieval and population of pick-lists.

Translation may be performed by the content type manager during loading and/or retrieval, for example. A template tool such as Apache Velocity may be used to implement the translation. The sensitivity of a content item to changes in the terminology server is a function of when the translation is applied e.g., during deployment, loading, or retrieval), for example. During deployment, context may be used algorithmically/heuristically to select dependent items and/or the deployment tool may specify the required dependent items. In general, context resolution is done heuristically (e.g., scoring and weighting schemes) because of the difficulty in determining an unambiguous algorithm to resolve conflicts. The content type manager may provide its own mechanism for context resolution, for example.

In deployment 750, a content item may be a part of multiple content frames. For example, multiple copies of a content item may be loaded by an application if it loads multiple content frames containing the item. Applications may search for and retrieve content frames. For example, content management may load and cache content frames. In certain examples, authoring tools may retrieve content items directly. Running applications may retrieve content frames during execution, for example.

Context may be resolved while constructing a content frame. That is, selection of context variants on which the deployed content item is dependent is done during deployment, for example. Content frames may thus be context specific. During load and retrieve, context may be used to select a content frame, not content items contained in the frame, for example.

A content frame may itself be considered a content item. Thus, the content frame may be versioned, have associated metadata, etc. Since a content frame is a content item, packages of frames may be constructed and distributed content frames without the associated source content items, for example. In certain examples, content frames may contain content frames, allowing courser grained deploy and undeploy operations. In certain examples, optimizations to frame loading (e.g., loading a single copy of a common content item) may be done, if desired, using techniques such as reference counting, etc.

In certain examples, content frames are related to a deployed root content item in a fashion analogous to the relationship between context variants and the content item. For example, a content frame is identified by the same UUID as the root content item in the frame and shares the same directory metadata. Each content frame may have its own unique identifier that may be used as a reference. Each content frame may be context specific and may have multiple versions. In certain examples, only deployed content items have associated content frames. Because of this relationship, content frames may be treated in a directory as properties of a content item along with context variants, for example.

In certain examples, content may be undeployed. An undeploy is a process of a making a (deployed) content frame unavailable to a running instance, for example. However, data instances stored in a CDR may be dependent on the content frames used to create the data instances (e.g., clinical element (CE) types). As a result, a content frame, once deployed, may not be physically deleted from the clinical content system without compromising referential integrity, for example. Undeploy, then, may make a content frame invisible to subsequent searches and context selection. Through undeploy, a previous version of a content frame may then be once again visible to search and context selection, for example. In certain examples, an undeployed content item may still be directly retrieved using the UUID for the content frame.

In certain examples, content item translation refers to modifying a content item during loading and/or retrieval to make the content item responsive to changes in content items on which it is dependent without redeploying the content item. For example, terminology designations and pick-lists may change independently of the deployment of the content item. Content item translation may be a responsibility of a content type manager responsible for a content item. For example, translations that make sense for one content type may not make sense for another content type. Content item translation may be context specific, for example. Content item translations may be performed by inserting custom macros in a content item (e.g., at authoring time) and applying a template tool to execute the macro and perform the translation with the item is retrieved.

Content item translations may be fine-grained. For example, they do not change the structure of the content item but replace elements (e.g., labels, lists of labels, etc.) within the item. Course grained modification of content frames (such as re-resolving content items that the content item being retrieved is dependent upon at retrieval time) may be undesirable because they can lead to unpredictable changes to application appearance or behavior. Hence, these kinds of modification are restricted to occurring at deployment time. In certain examples, common tools may be used to perform translation of content items represented in XML or HTML. Apache's Velocity is used here as an example only. Dependencies for items that depend on translations may be managed by maintaining a content frame dependency on a content frame containing the items to be translated (e.g., a terminology content frame) rather than by maintaining specific dependencies, for example.

Loading 760 is a process of retrieving a content frame containing deployed content item(s) from storage and making the frame available for use by running application(s). Content items in a content frame may be translated during loading. For example, terminology designations may be resolved and/or pick-lists retrieved. A content frame may be cached after loading. Content items contained within a content frame may be loaded as a single operation, for example.

In certain examples, the choice of doing translation at retrieval time or load time is up to the content type manager. Translating at load time means that the cost of translation is amortized over multiple uses of the item; translating at retrieve time means that the item is more sensitive to context variation and changes in resolved content. A selection of translation time may be content type specific, for example.

Retrieving 770 includes fetching a loaded content frame by a consuming application. Content items within the content package may be translated during retrieval (e.g., resolving terminology designations, retrieving pick-lists, etc.). A loaded content package may be retrieved multiple times by different clients, for example. An application may choose to reuse (e.g., cache) a retrieved content package at its discretion. Content items within a content frame may be loaded as a single operation, for example. In certain examples, since a content item may be present in different content packages, different instances of an item may be translated using different context. For example, an application may show a content item in two different languages concurrently for comparison.

A choice of doing translation at retrieval time or load time may be made by the content type manager. Translating at load time means that the cost of translation is amortized over multiple uses of the item. Translating at retrieve time means that the item is more sensitive to context variation and changes in resolved content. A selection of translation time may be content type specific, for example.

Figure 9:
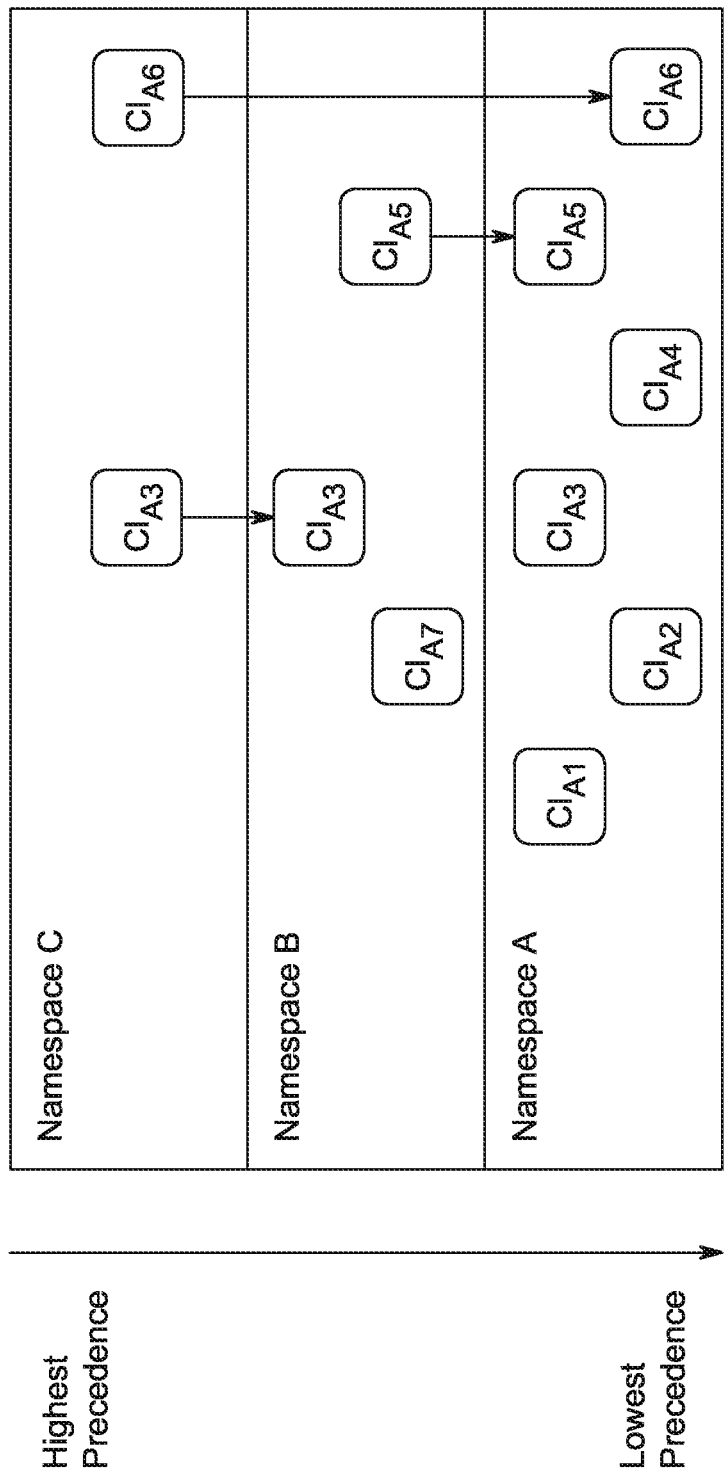
FIG. 9 provides an example of namespaces A, B, and C including various content items (CIs).

In certain examples, content may be divided based on namespace. A namespace is a partition of content items in a system where each partition is owned and managed independently of other partitions. FIG. 9 provides an example of namespaces A, B, and C including various content items (CIs).

Namespaces may be motivated by various factors. For example, content items in one namespace may be protected from modification by another party (for example, a customer modifying GE distributed and owned content). Applying maintenance (e.g., updates, bug fixes, etc.) becomes difficult, if not impossible, if a customer can modify GE distributed content (e.g., customer modified content may potentially be broken when replaced with an update). Alternatively or additionally, for example, customers may be allowed to add and extend distributed content in safe ways while enforcing governance restrictions on such modification (e.g., models may not be modified or extended, but MPVs may).

While some of these restrictions may be enforced by a security system, customers often set security policy, so another mechanism may be used to enforce such restrictions. Additionally, some rules such as inheritance restrictions may not be adequately managed via security policy.

In certain examples, a simplified namespace model provides that each content item in a system may be searched for using a single namespace precedence order. It is possible that different content types may involve different search precedence (e.g., a search path to resolve data models may not be the same as a search path to resolve forms or reference content). Extensions to the model can be made based on circumstances, for example.

In certain examples, namespaces may be "owned" by a provider, a customer institution, a department, etc. Such ownership separates provider content from customer content, for example. Multi-tenancy and digital rights management may be facilitated through the use of namespaces, for example. In certain examples, only the owner of a namespace may create or modify content items within the namespace. An owner may own multiple namespaces, for example. A clinical knowledge platform and/or associated enterprise clinical information system may serve as an owner of a "root" namespace (and possible others), for example. Each customer installation may be an owner of at least one namespace for that customer, for example.

In certain examples, an "owner property" on a content item used as a context attribute is also presented in some contexts as equivalent to a namespace. However, in context resolution, using an owner property there may be no inherent precedence. For example, given a concept with designations potentially owned by A, B, and C, an application asks for the designation owned by A but that designation does not exist. Does the system return designation B or designation C? In general, property precedence in context resolution involves a heuristic to resolve (e.g., weighting and scoring schemes).

Additionally, there may be necessary relationships between content items in namespaces. For example, specialization via inheritance, overriding content items in one namespace with the same item in another, copying an item from one namespace to another (e.g., is it legal to do the copy?), etc. These behaviors may or may not be able to be implemented using an owner property (alone) in the general case.

Additionally, "owner" may be used in at least two different senses: first, as an intellectual property/digital rights management (IP/DRM) concept where it designates actual ownership (e.g., a package by "owner" is a practical application of this concept—package everything that is owned by an owner); second, as an attribute used to select a desired/appropriate context variant when retrieving a content item. This second usage is more directly analogous to namespaces with the caveats above.

In certain examples, a difference between an owner context attribute and a namespace is that namespaces are known to and defined by a system rather than defined independently for each content item in content (e.g., owners are generally terminology content). The system can establish precedence, maintain persistent/immutable relationships between items in different namespaces without expectation that the relationships will change, for example. That is, "namespaces" may be part of a reference implementation; owners are content defined and hence may be interpreted by the reference implementation, for example.

In certain examples, namespaces have "precedence" when searching retrieving, etc. For example, as shown in FIG. 9, a highest precedence namespace C is first searched for a content item, then a second highest (e.g., namespace B), etc. Precedence may be established when configuring the system or defining the name spaces, for example. Precedence may be overridden when deploying a package.

In certain examples, relationships may exist between content items in one namespace and content items in a lower precedence namespace. In certain examples, changing namespace precedence may change the nature of a relationship.

In certain examples, a new content item may be created in a higher precedence namespace by copying an item in a lower precedence namespace. For example, an MPV may be copied from base content, modified, and saved as a user-owned MPV. A content item may be created in a higher precedence namespace that hides or replaces the same content item in a lower precedence namespace, for example. For example, a new version of a formlet that hides the same formlet in base GE Qualibria® content to customize display of that formlet. Creating a new content item that specializes (e.g., inherits from) an existing content item may hide or replace a base content item in a lower precedence namespace. For example, a new attribute may be added to a patient clinical element model provided by Qualibria by specializing the Qualibria patient model.

In certain examples, namespace relationships are managed by a content management system. If a base content item is modified, a specialized content item may need to be redeployed. In certain examples, specialization of a content item in a namespace may be allowed in another namespace but copying the content item may not be allowed. State changes in a base content item may involve state changes in a specialized content item (e.g., if the base item is deprecated, the specialized item may also require deprecation), for example. In certain examples, digital rights management may prevent a copy of a content item from being created. In certain examples, if a content item that was copied to a new namespace is modified, an owner of the target namespace may need to be notified of the change so the copy can be reviewed for changes.

In certain examples, an owner attribute on a content item may be insufficient to manage namespace relationships. Clinical element models (CEMs) are an example of a relationship restriction: copying and hiding a CEM can lead to data inconsistencies while specialization through restriction or extension can be safely done. Hiding an MPV on the other hand, is generally a safe operation, for example. In certain examples, relationship management/enforcement is a responsibility of a content type manager (CTM), or at least the CTM should be able to specialize system relationship management.

Namespaces may be used in a variety of stages of a process. For example, namespaces may be used during authoring. For example, namespaces may be used when resolving context variants, establishing relationships such as copy, copy and hide, etc. Namespaces may be used during packaging, for example. A package may include content items from a single namespace, for example. Context variants, relationships, etc., in other namespaces involve dependencies on packages in those namespaces, for example. Namespaces may be used during deployment (e.g., when resolving context variants, when establishing relationships such as inheritance relationships, etc.), for example. In certain examples, namespaces are not used during load and retrieve at runtime.

In certain examples, each context variant of a content item has a current "state". For example, a state may include deployable, deployed, loaded, deprecated, etc. Each content type has a set of allowable states and a set of allowable state transitions represented as a state machine. Content types may have different state machines in an authoring environment than in a runtime environment, for example. State machines may be owned by a content type manager since the manager defines a meaning of each state for a content type.

In certain examples, a state in a runtime system is actually the state of the content frame. However, for simplicity, a state of the content frame is assumed to be (and managed as) the state of the root content item. A state of content items included via dependency resolution may be irrelevant to the runtime system (e.g., it may be required that the root content item of the content frame be redeployed to bubble up state changes in that item).

In certain examples, lifecycle management refers to a set of workflows that manage transition of a content item from one state to another. Each state in a content type state machine is associated with a distinct workflow that manages the content item when in that state, for example. In certain examples, workflows are content items to allow variation across implementations.

Figure 10:
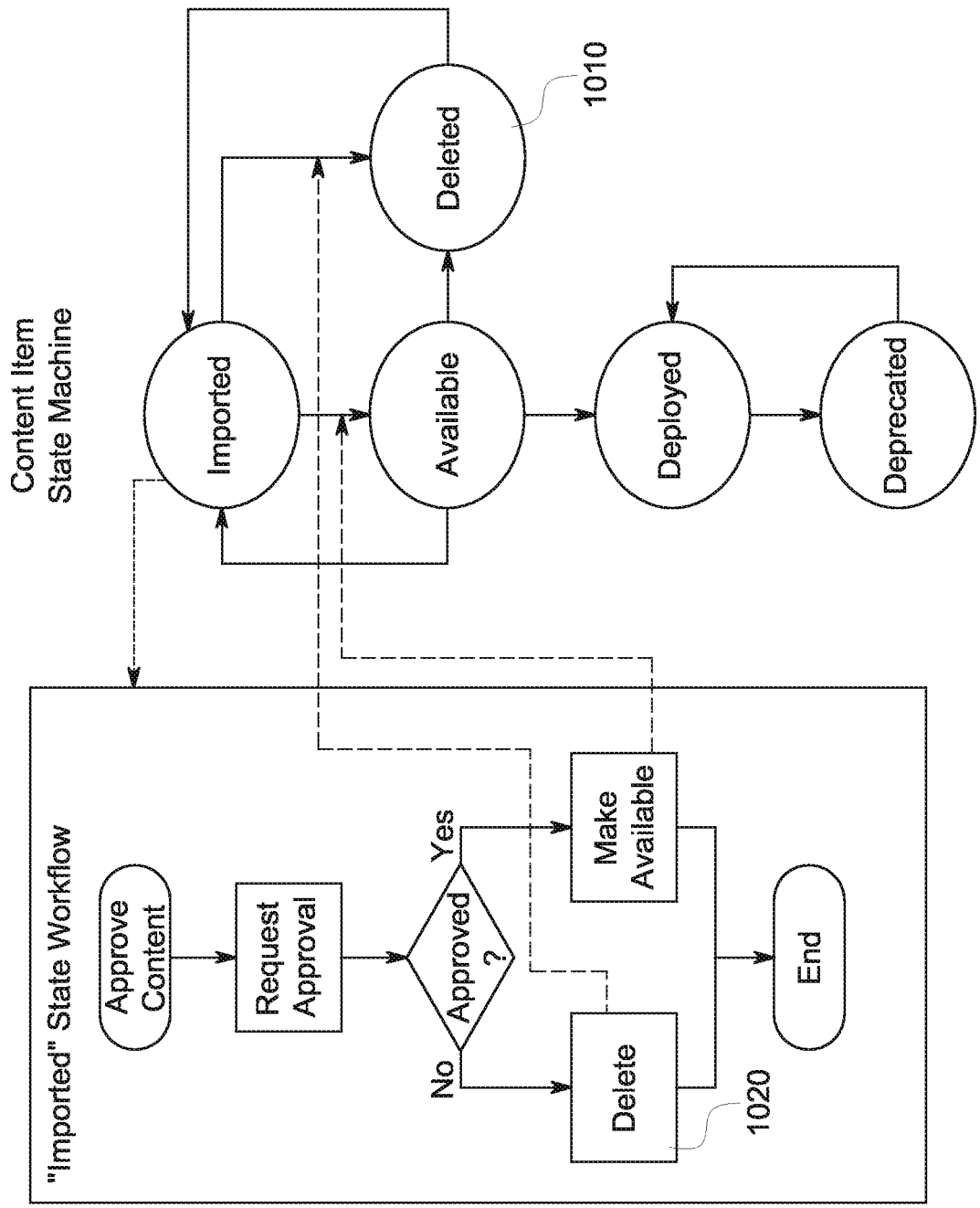
FIG. 10 depicts an example of a state versus a workflow.
Figure 11A:
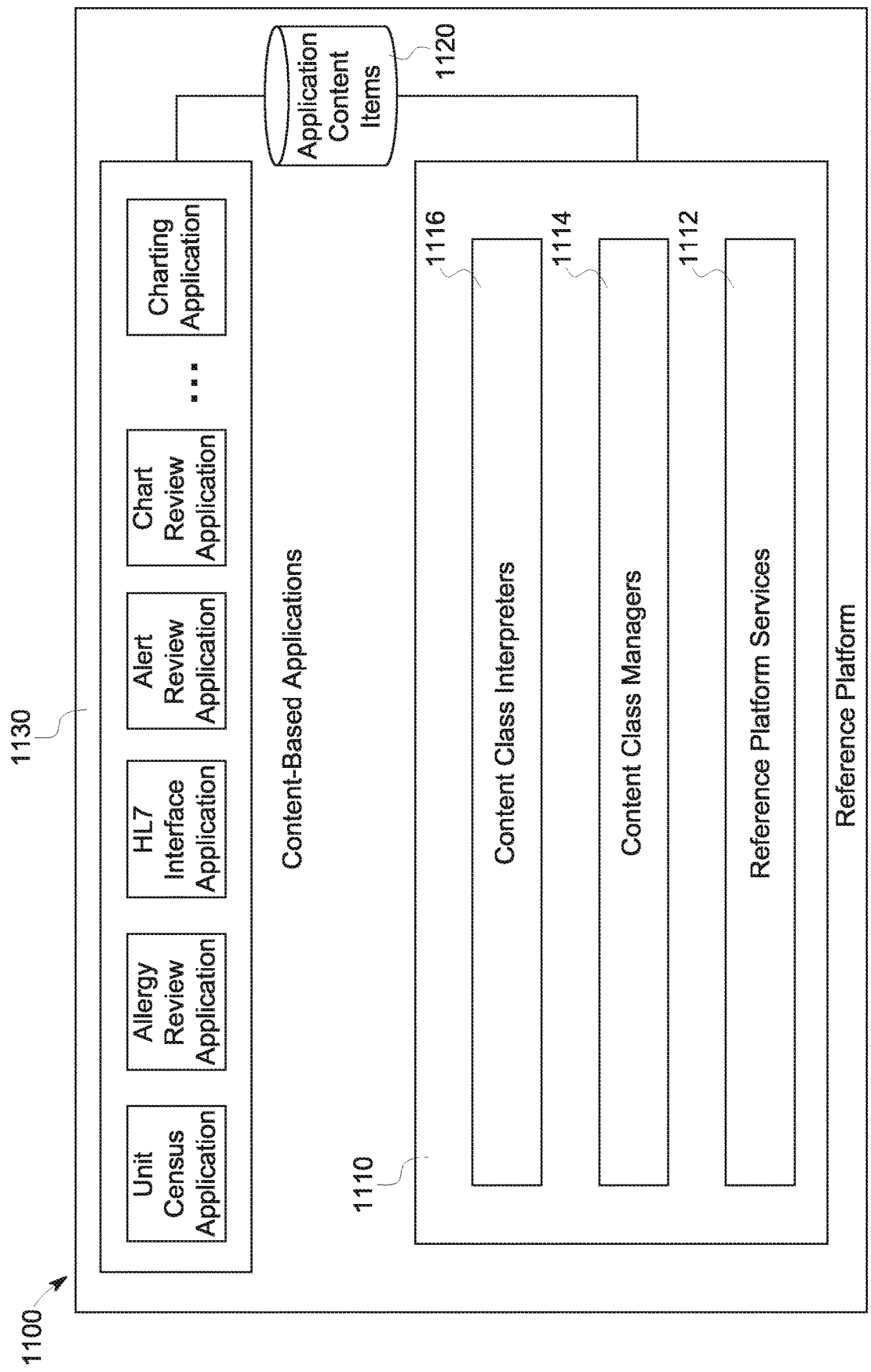
FIG. 11, consisting of FIGS. 11a-11d, illustrates an example clinical information system including a reference platform and one or more content items that define clinical functionality.
Figure 11B:
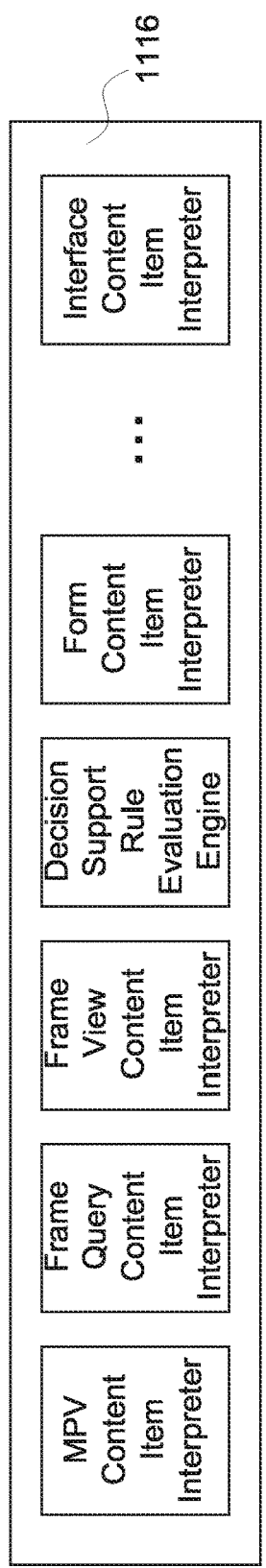
Figure 11C:
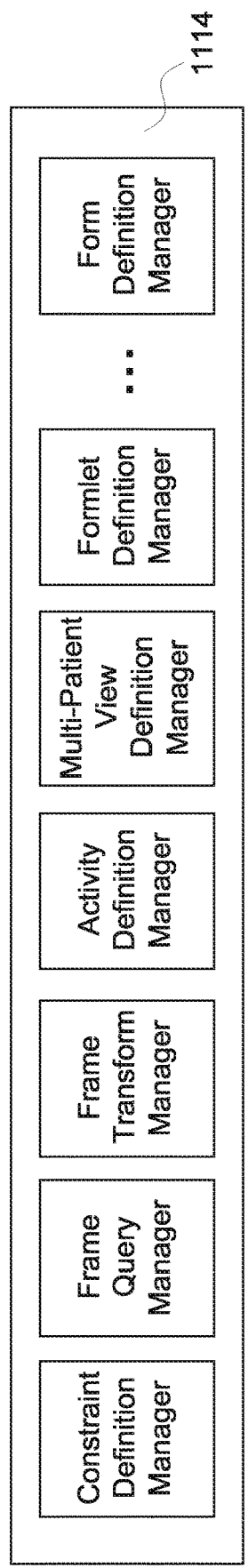
Figure 11D:
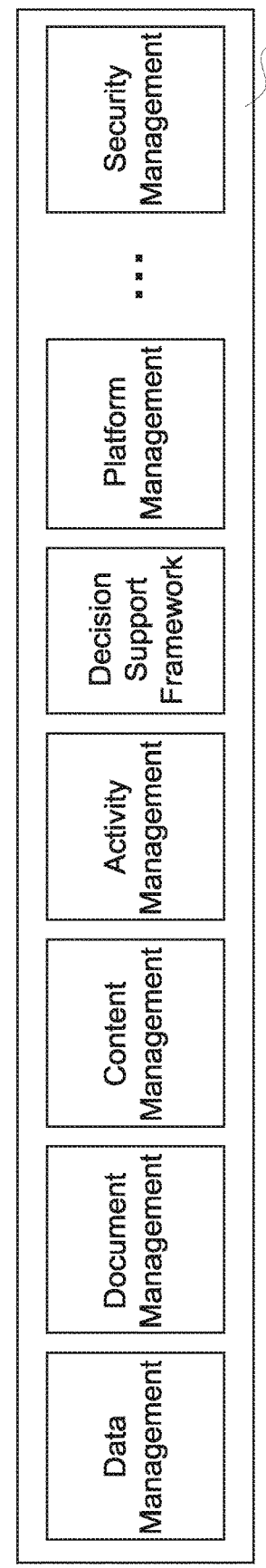

FIG. 10 depicts an example of a state versus a workflow. As shown in the example of FIG. 10, each state in a content item state machine 1010 has an associated workflow 1020 that controls transition(s) to the next state(s).

In certain examples, governance refers to a set of policies that manage lifecycles of each content type. Governance policies are implemented in state machines and associated workflows of a content type, for example. Governance may be an operational function, for example.

Certain examples provide a content-based clinical information system including a stable reference platform that defines and executes the core capabilities of the system and a set (e.g., one to many) of content classes (e.g., content based languages) that are implemented upon the reference platform and that independently define clinical information functions. The content classes are specialized to allow implementation of narrowly defined clinical functions, for example, Defined clinical functions can include data definition, data query, data transformation, data display, data entry, decision support rules, etc., for example.

In certain examples, clinical applications are created by composing one or more content items (e.g., instances of a content class) from one or more content classes. Each content item is authored or created independent from the creation of the reference platform. Content items and the reference platform can have independent life-cycles and evolve independently over time, for example. Since content classes are independent, support for additional content classes can be added as an update to the reference platform to extend core system capabilities, for example.

Certain examples provide content and data, along with executable software or code. In certain example, content includes data and expressions/instructions concerning data. However, neither data nor content is "software" as the term software is traditionally defined. In certain examples, content is stored in a content database and is independent of hard-coded libraries. Thus, clinicians do not need a new installation of software to change an application, such as a multi-patient view (MPV) dashboard. Other dashboard views can include a rapid recovery dashboard, a hospital-acquired infections dashboard, etc. Content can be configured by a clinician, technician, and/or other user at a location without the platform provider's intervention. Clinicians can author new MPVs on the fly, for example. In certain examples, content can be used to facilitate a query for data by a user and/or application.

FIG. 11 illustrates an example clinical information system 1100 including a reference platform 1110 and one or more content items 1120 that define clinical functionality (e.g., content-based applications). The example content-based clinical information system 100 of FIG. 11 includes a reference platform 1110 having three major layers 1112, 1114, 1116.

In the example system 1100 of FIG. 11, Reference Platform Services 1112 provide foundation services to implement content class managers and interpreters. The reference platform services 1112 are constructed using standard software development techniques and can be modified independent of content items implementing application functionality to enhance available system functionality without impacting the application functionality, for example.

In the example system 1100 of FIG. 11, a Content Class Managers layer 1114 implements management services for one or more content classes. A content class includes defined (e.g., a narrowly defined) domain specific language that allows clinical personnel to define custom programmatic elements (e.g., content items) that will be used when composing a clinical application (for example, clinical vocabulary concepts, clinical data models, data queries, data transformations, display forms, etc.). An example Content Class Manager provides capability(-ies) to author content items of that content class. The example content class manager provides capability(-ies) to package those content items for distribution, export and import the content items from and to installations of the clinical information system, and deploy the content items to a running clinical information system (e.g., compile, translate, etc., the content item into an executable form). The example content class manager provides capability (-ies) to load the content items into memory while performing context-based translation of the content item (e.g., resolve terminology designations, pick-lists, etc.), and to retrieve the content items for execution in an associated content class interpreter. While a running clinical application can include content items of different content classes, each content item is independently managed by the content class manager associated with the content item.

In the example system 1100 of FIG. 11, a Content Class Interpreter layer 1116 defines one or more interpreters (e.g., programs that consume a content item and execute the instructions defined in the content item) for content items of each content class. Since an application is a composition of content items, multiple content class interpreters can participate in the execution of the composed application(s). Content class interpreters consume a deployed (e.g., executable) form of the content item(s). Optimizations and/or other improvements to performance of a content item interpreter can be implemented in conjunction with a content class manager, for example.

Content Based Applications are composed of one or more content items that are managed by content class managers and executed by content class interpreters. A set of content items of which an application is composed are stored in a content repository and managed as a set of interdependent items. Content based applications are independent of the reference platform; that is content based applications can be changed without changes to the reference platform, and the reference platform may be changed without changes to the content based applications (though content based applications may be changed to take advantage of new capabilities in the reference platform), for example.

Since medical practices vary widely between different institutions (and even within institutions or between patients) and change rapidly as medical practices evolve, prior clinical information systems require extensive customization to be deployed widely. Very frequently, this degree of customization can render ongoing maintenance (e.g., new releases, error fixes, etc.) difficult or even impossible. Additionally, responsiveness to requests for customizations may be unacceptable to the institutions because of the difficulty in creating, testing, distributing, and managing the customizations.

Two common approaches to these issues may be found in existing products. First, the producer of the system tightly controls the software system and controls/restricts the changes that can be made to the system, thereby severely restricting the ability of the software to be customized to specific customer needs. Second, the producer of the system may allow extensive customization of the software wherein each implementation becomes essentially a custom system which limits the maintainability of the system.

Certain examples address these problems by separating the application, where customization generally occurs, from the system itself, where maintenance generally occurs. An example clinical information system application is implemented in content, that is, as a set of content items that are created and maintained independently of the system, often by the customers of the system themselves. The reference platform (e.g., the system) is maintained, enhanced, tested, and deployed by a vendor. Since the application (in content) is independent of the reference platform, the two can evolve largely independent of each other. Independent evolution allows a much greater degree of possible customization without reducing the maintainability of the system, for example.

Rather than basing content on a single general-purpose interpreted language, certain examples implement a content based system as a set of content languages. In certain examples, each content language is narrowly focused and specialized to allow independent evolution, optimization, etc.

In certain examples, by separating applications from a reference implementation, independent evolution of the application and the system can be supported. In certain examples, application(s) can be authored by domain specialists rather than by engineering. For example, terminology and data can be modeled by informaticists; clinical forms can be designed by clinical teams; etc. In certain examples, functionality can be added to the system incrementally by adding new content classes to the system. Since content classes are narrowly focused for specific tasks, a risk of over-generalization is reduced or avoided, for example. Content classes can be independently evolved and improved/optimized, for example.

In certain examples, clinical content includes structured knowledge components such as decision support rules, protocols, reports, user preferences (e.g., triage form layout, patient and/or department worklist format, etc.), and unstructured knowledge components such as discharge instructions, guidelines, etc. Clinical information systems (CIS) that are content-driven provide functionality that improves clinical outcomes by enhancing compliance with institutionally/nationally recognized standards of care and reduce practice variation. In certain examples, a new process has been defined to streamline clinical content management from its inception to its consumption by the CIS.

The example process allows for building of an infrastructure for managing clinical content in a more efficient and more optimal manner. Using this clinical content management process, clinical content management is scalable and expressive, for example. When a CIS is introduced into a new environment, lack of a standard process interferes with resource planning, effort planning and estimating timelines, for example. An example clinical content management infrastructure built around this process can help with the implementation effort by identifying appropriate dependencies, breakdown tasks along with their associated resources, and help align priorities.

In an example, a small client is interested in going live with a couple of clinical modules (e.g., a discharge module and a billing module). As part of these modules, using the example content-driven process, structured and unstructured clinical content can be authored, versioned, packaged, and tracked to ensure compatibility with future updates. Building on the example use case, if the client wants to add its own local content, plug-n-play packagers and deployers are provided that are applicable only to these two modules. If the client is happy with the two example modules and wants to go live with additional modules, the infrastructure built around the process can scale up to identify potential clinical content interdependencies, help eliminate redundancies, and bridge clinical application versions and clinical content versions, for example.

In certain examples, the clinical content management infrastructure can be integrated into a software lifecycle to eliminate separate iterations and planning exercises. Integration can produce significant savings in planning, effort, and execution time, for example.

In certain examples, during the content authoring and packaging processes, the infrastructure verifies and validates dependencies and helps ensure content integrity, for example. The infrastructure eases the process of versioning at the content and package level.

In certain examples, future updates can be automatically packaged as patches that can be released internally and/or externally to clients on a pre-determined schedule. Patch releases can still maintain content integrity that can be described through a conformance statement, for example.

In contrast, prior enterprise clinical information systems rely on ad-hoc processes for clinical content management, wherein processes are manually created on the fly by programmers on a case-by-case basis. Some significant impediments to the adoption of standards and coded content (e.g., structured/unstructured) in clinical information systems are high costs associated with clinical content authoring. In addition, prior techniques resulted in uncertainty in managing dependencies between content types, and uncertainty in creating predictable release cycles.

Thus, certain examples provide a clinical content management process that is scalable, expressive, and semantically interoperable. For example, the process is scalable in that it can support core content as determined by an application's needs in addition to customer/competitor specific content. For example, the process allows end users to consume content to support individual preferences at an enterprise level. For example, the process provides an infrastructure for clinical entities to create semantically interoperable systems to derive clinical, research and business benefits thereof.

From a business standpoint, the example process enables modular content packages and pluggable deployment. This flexibility allows tailorable content to support different types of clients to augment a "surround and supplement" strategy, where-in a small client with limited budget can go live with only couple of modules/content-deployers, whereas a large enterprise customer might want a whole suite of content management infrastructure.

Certain examples define processes apriori to help ensure that structured and unstructured clinical content development and management is more predictable, measurable, efficient, and integrated into application lifecycle management. Current systems and/or processes for managing clinical content in content-driven systems are fraught with uncertainties such as in version compatibility, quality control, timely packaging and delivery of content, updating knowledge bases, and smart deployment.

Building a clinical application on an infrastructure as described herein provides significant benefits to a content management process such as making it scalable, expressive, supportive of standard(s), semantically interoperable, and flexible.

In certain examples, content and infrastructure can be used to map or resolve concept identifiers into human-readable designations using a terminology.

Typically, when a computer system is designed for an industry or application, the system is designed to meet the needs for the most customers in the industry as possible. Sometimes different customers want to use the system in different ways. This can be solved by making systems that are configurable. There are cases were different individual users or departments want their own configurations or preferences. This invention improves the way a system stores and manages these preferences.

Some industries have adapted the way they do business to fit the computer system purchased. A distribution center might change the way it fills orders in order to fit the way the computer software wants it tracked. This does not work with clinical information systems. Different hospitals vary greatly in how they provide health care and how they use their information systems. Different doctors also do things differently. It may be simple to train a store clerk the new way to fill orders, but it is difficult to ask a doctor to change the way they do things. It is not reasonable for a health network to adapt to its chosen software, so the software needs to adapt to the particular health network, region, hospital, department, and care provider.

One example of how a clinical information system might be configured is a patient admission screen. The software for the clinical information system includes an admission screen for new patients. The admission screen includes a form associated with a workflow directing which information to collect and when to collect it. The admission screen may also display other information about the patient or hospital to assist the care provider during the admission process. While the system includes an admission screen that works well for many hospitals, it will not have everything needed for every situation.

Different hospital networks may want to change the admission process to be different from the one that is included by default with the software. In those cases, they will want to modify the admission process to fit the needs of their network. Within the hospital network, there may be a region that needs to modify their admission process. Within that region, there may be a hospital that needs to add a step in the admission process specific to that hospital. There may even be a care provider who wishes to modify the way the admission form is laid out to fit a user specific need.

These modifications are based on a context. The region, hospital, language, and user all help to define the context for the particular admission process. The context is based on a hierarchy where the hospital depends on what regions it is in, and the user depends on what hospital it is in. For example, a user might customize their layout of the admission form one way when they are working at one hospital. It might need to be customized another way at a different hospital.

Traditionally, preferences are stored in a separate data store or stored locally on a client workstation. The system retrieves the content and preferences separately, and then the system alters the content based on the preference. This requires the consumer of the content to be aware of the preference system and also requires the consumer to alter the content.

An example of a traditional preference application is an admissions screen for collecting new patient information. The system may want to allow users to choose if the form was displayed vertically or horizontally. The form itself could be saved as content in a content repository. The system could save the preference, vertical or horizontal, in the preference storage. The application would need to retrieve the form, and then it would need to read the preference for the user and modify the form to appear the way the preference indicated. This requires the application to be programmed in a way that it knows what all the possible preference are, and it would have to know how to modify the form to fit those preferences at runtime.

In certain examples, a clinical information system provides functionality for users to define what the preferences are based on each hierarchical context as needed or desired. The CIS should then provide a correct admission process for the context that exists at admission time. Certain examples provide an intelligent, preference-based content system capable of storing hierarchical-based preferences.

Certain examples store content for each preference separately. A consumer passes in a context when requesting content, and the content for those preference(s) is returned. There is no need for the consumer to analyze the preferences or alter the content. In the patient admission example, an admission form is stored as content to be used by default in the application. If a care provider prefers to change the admission form, the user specifies the desired change, and the system stores that form as content in the content system. The new content is stored with context information that includes the specific user. When the system retrieves the admission form, the system identifies that the context includes the specific user, and the content for that user is used. The content storage is aware of the context, but the consumer did not need to know what the preference was and did not need to alter the content.

Language provides another example of how a preference can be stored as content. A patient discharge form can be stored by default in English. In a bilingual hospital, care providers may speak two languages, but a patient may only speak one language or the other. A second discharge form can be stored as content with a context indicating that it is in a second language different from a first language (e.g., a discharge form in Spanish and a discharge form in English). The patient's language is included as part of the context when retrieving the discharge form from the intelligent, preference-based content system. The application then displays the correct discharge form.

In certain examples, by storing preferences as content, preferences do not need a separate data store. Preferences can be assigned that are user and/or patient specific. Preferences are stored as content, so a consumer of the content does not need to have a knowledge of the preference system. Preferences can follow a user across workstations and/or be centrally managed, for example.

In certain examples, the system and associated software is flexible and configurable by end users. The flexibility and configurability should improve adoption by and usefulness for clinicians, for example. Context-based preference configuration and storage can be provided as part of an enterprise clinical information system, such as GE's Qualibria® system, for example.

Certain examples resolve multiple variants of a content item based on who, what, and/or where the content consumer is. This allows consumers to create, specialize, and/or customize their own content on top of vendor-released content (e.g., shareable and interoperable content). This allows for a single content type to vary by properties associated with the content consumer without the need to customize every application that consumes that content to be aware of the rules necessary to vary the display of the content.

In clinical applications, there are often times that information and data are to be displayed in different ways based on a context of application use. A role of a clinician may impact what clinical information he or she wants and/or needs to see and how he/she wants or needs to see it. A location of a user may also impact a type of information that is desired to be displayed based on clinical need, preference, etc. Clinical information may also be displayed in one or more languages, especially for patients.

Resolution of context by an application allows appropriate information to be displayed based on who, what, and/or where the user of the application is. This ability enables streamlined workflows and targeted documentation for clinical use. This also gives flexibility to customize content for specific use(s).

Previous attempts have included multiple modules in an application that are developed for a specific role or location, thus allowing customers to configure and/or copy parts of an application in order to meet specific context needs. This requires that all applications that use this content also use this code, thus forcing re-deployment of the application.

Also, externally developed applications would not be able to take advantage of the rules applied to the context resolution. Thus, a single content item could be created that hides or shows parts based on parameters passed in. This would require complex algorithms during display to parse the content and modify it based on parameters. It would also have to be duplicated everywhere the content was used. Another option is to provide different content items without context resolution and have the consuming application select the correct content item based on algorithms developed per application. Alternatively, a heuristic rules engine could be implemented that would preclude the need for a context resolution algorithm as you could have several separate content items and have the rules engine determine which item would be appropriate to return.

Figure 12:
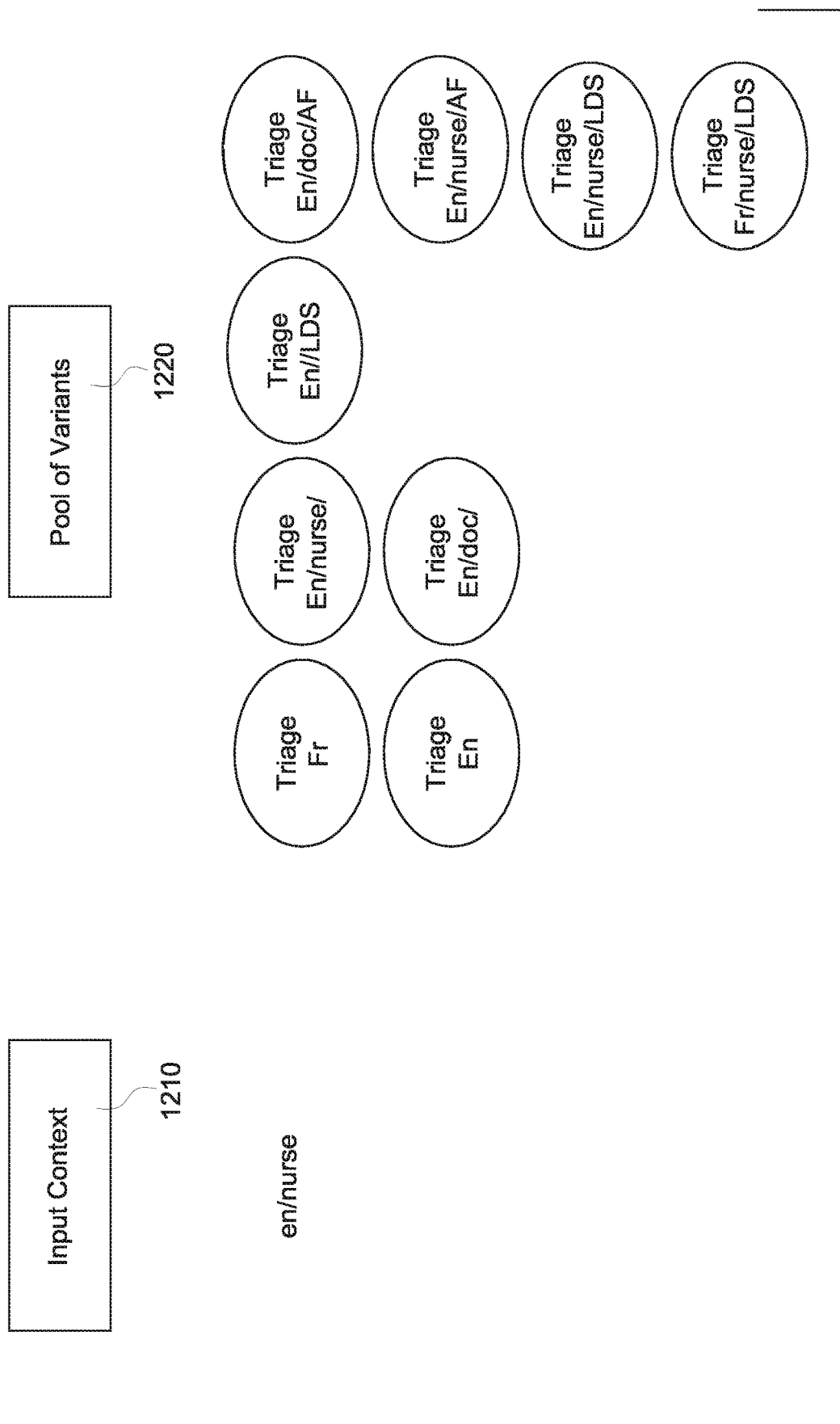
FIG. 12 illustrates an example of runtime context resolution using an input context and a pool of variants.
Figure 13:
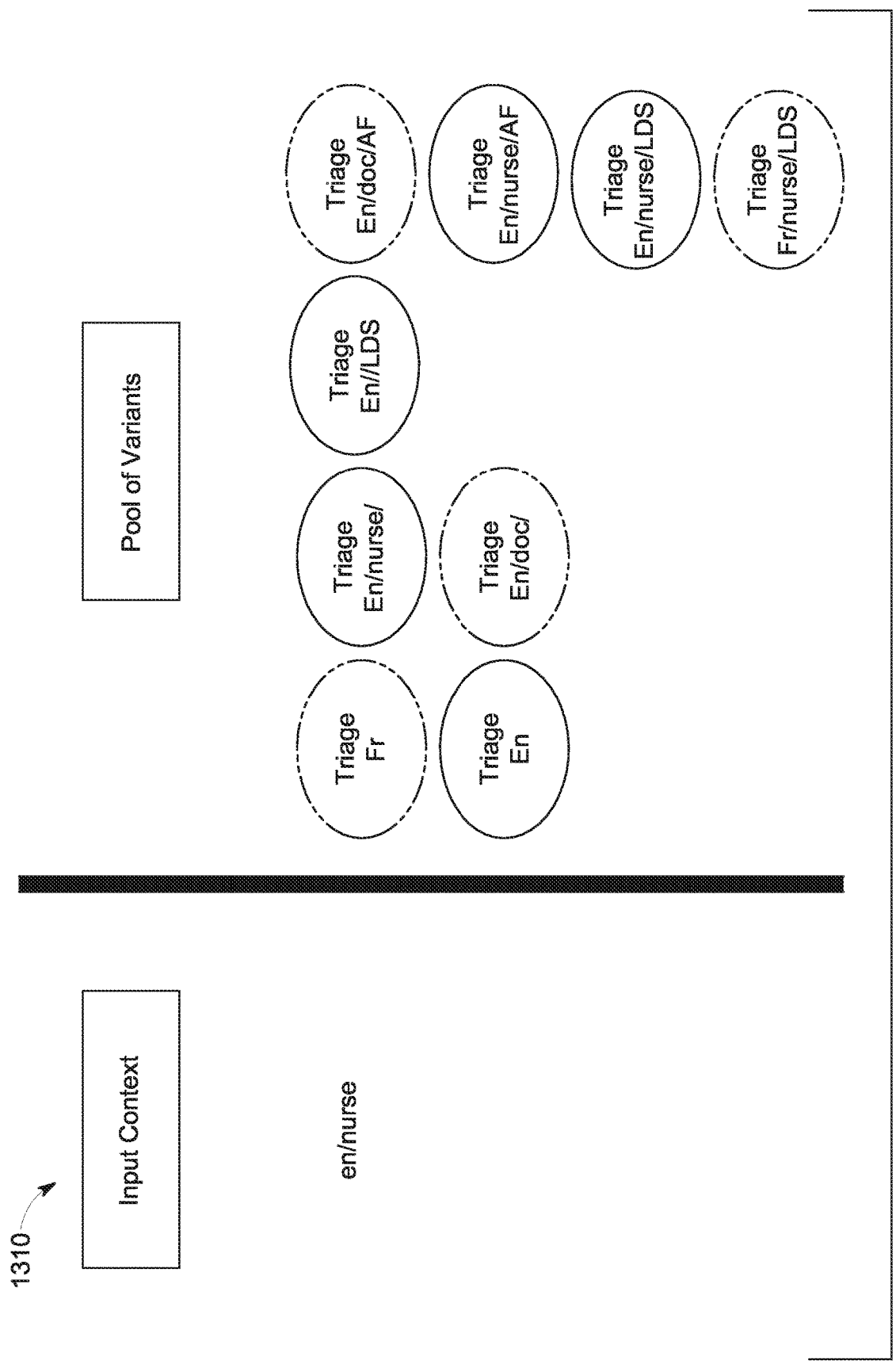
FIG. 13 shows an example in which conflicting variants are rejected.
Figure 14:
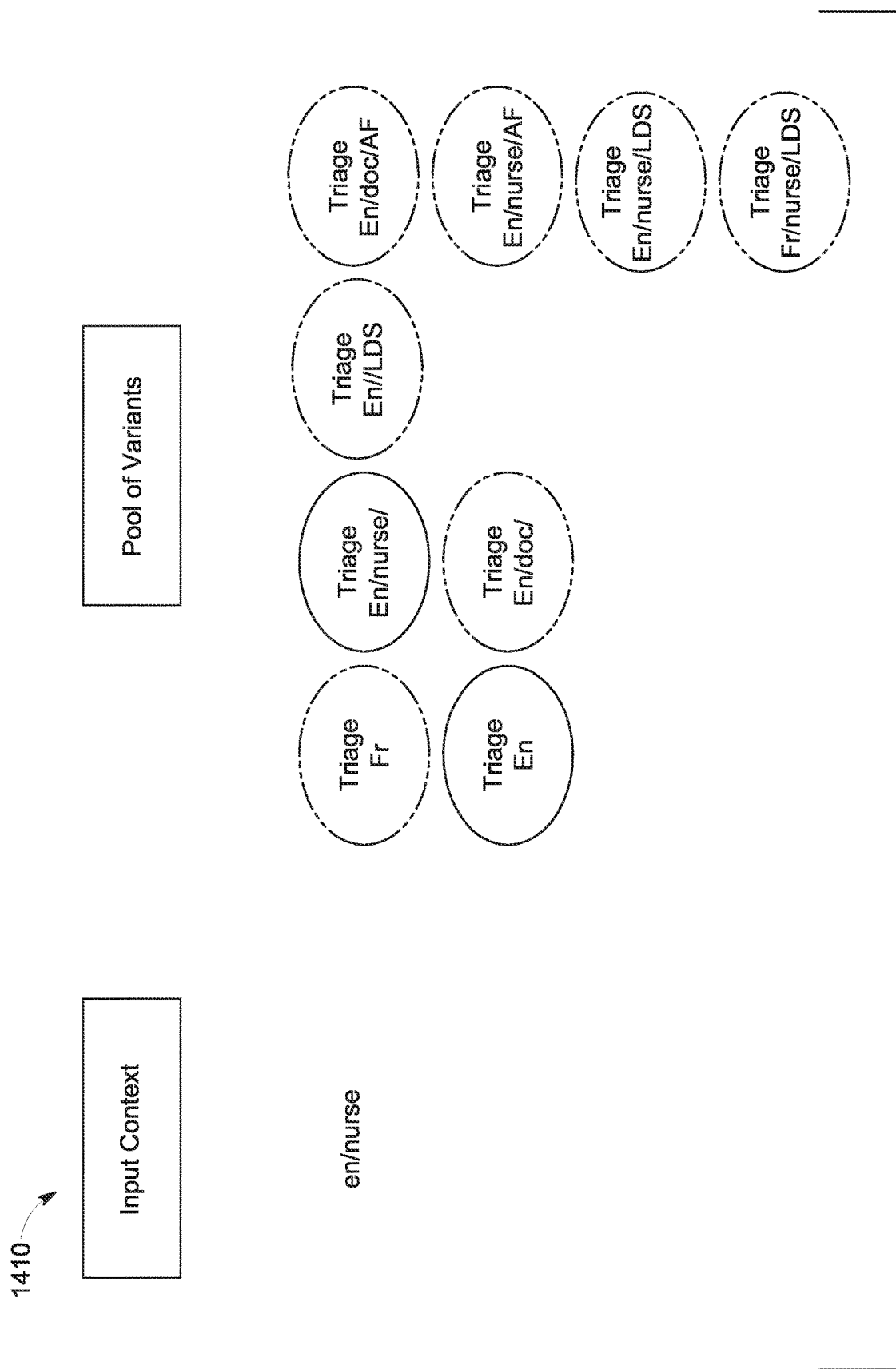
FIG. 14 shows an example in which more specific context variants are rejected.
Figure 15:
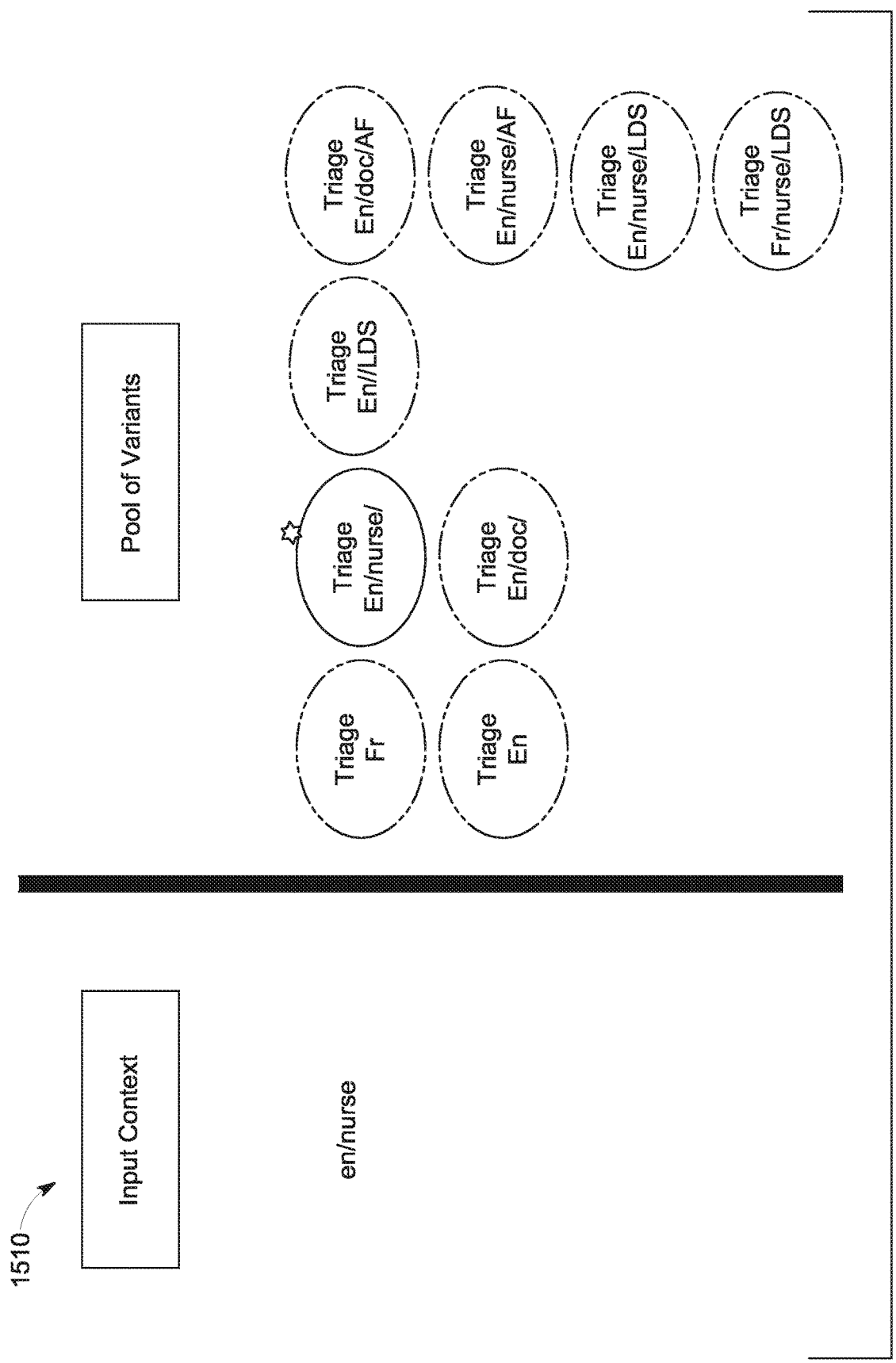
FIG. 15 shows an example in which, of remaining variants, a most specific variant to an input context is accepted to resolve the input context into a context variant.
Figure 16:
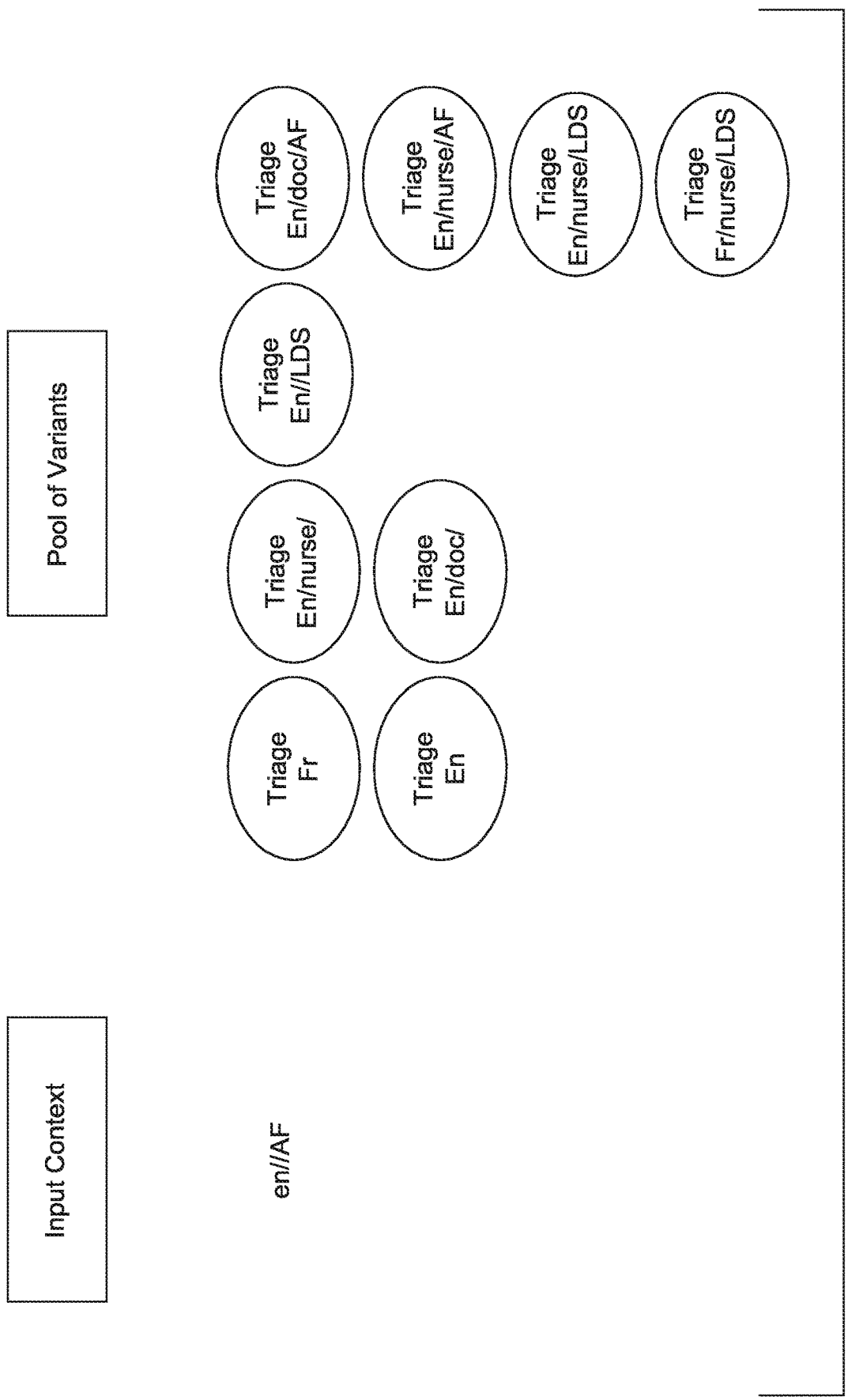
FIGS. 16-18 provide examples of runtime context resolution.
Figure 17:
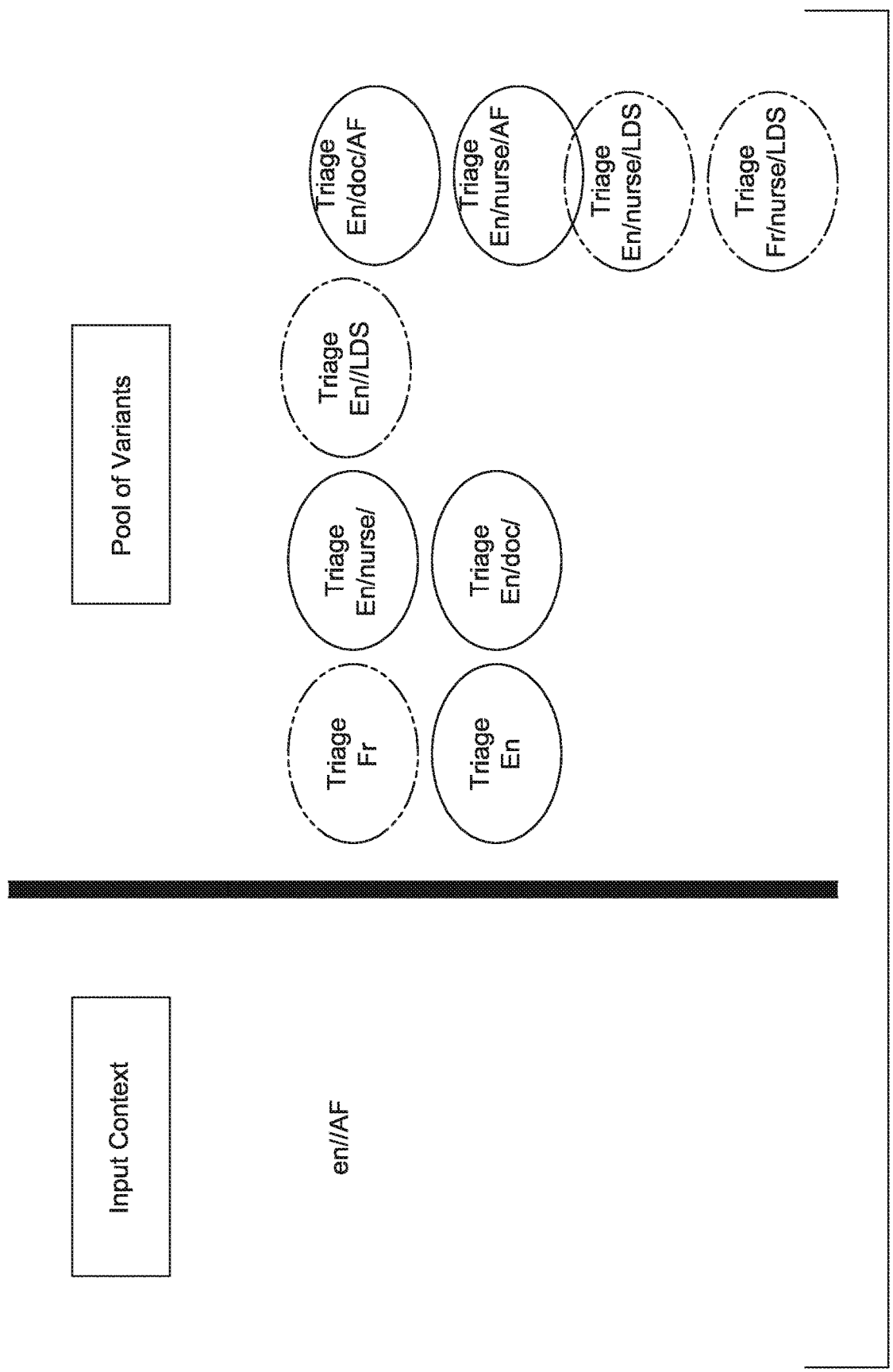
Figure 18:
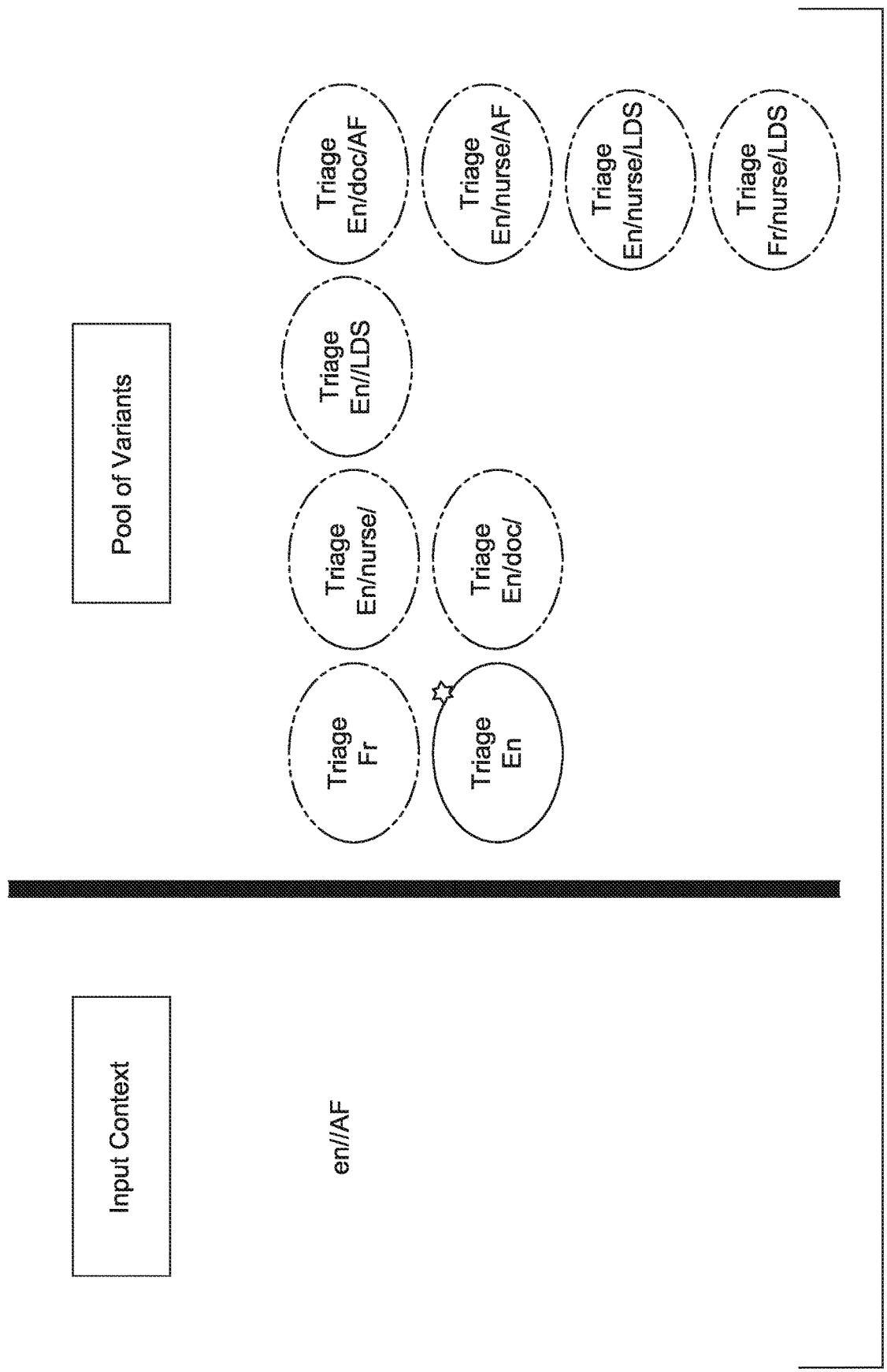

FIG. 12 illustrates an example of runtime context resolution using an input context 1210 and a pool of variants 1220. As shown in the example of FIG. 13, at 1310, conflicting variants are rejected. As shown in the example of FIG. 14, at 1410, more specific context variants are rejected. As shown in the example of FIG. 15, at 1510, of the remaining variants, a most specific variant to the input context is accepted to resolve the input context into a context variant. FIGS. 16-18 provide another example of runtime context resolution by, first, rejecting conflicting variants; next, rejecting more specific context variants; and then, accepting a most specific of the remaining variants for the input context.

Figure 19:
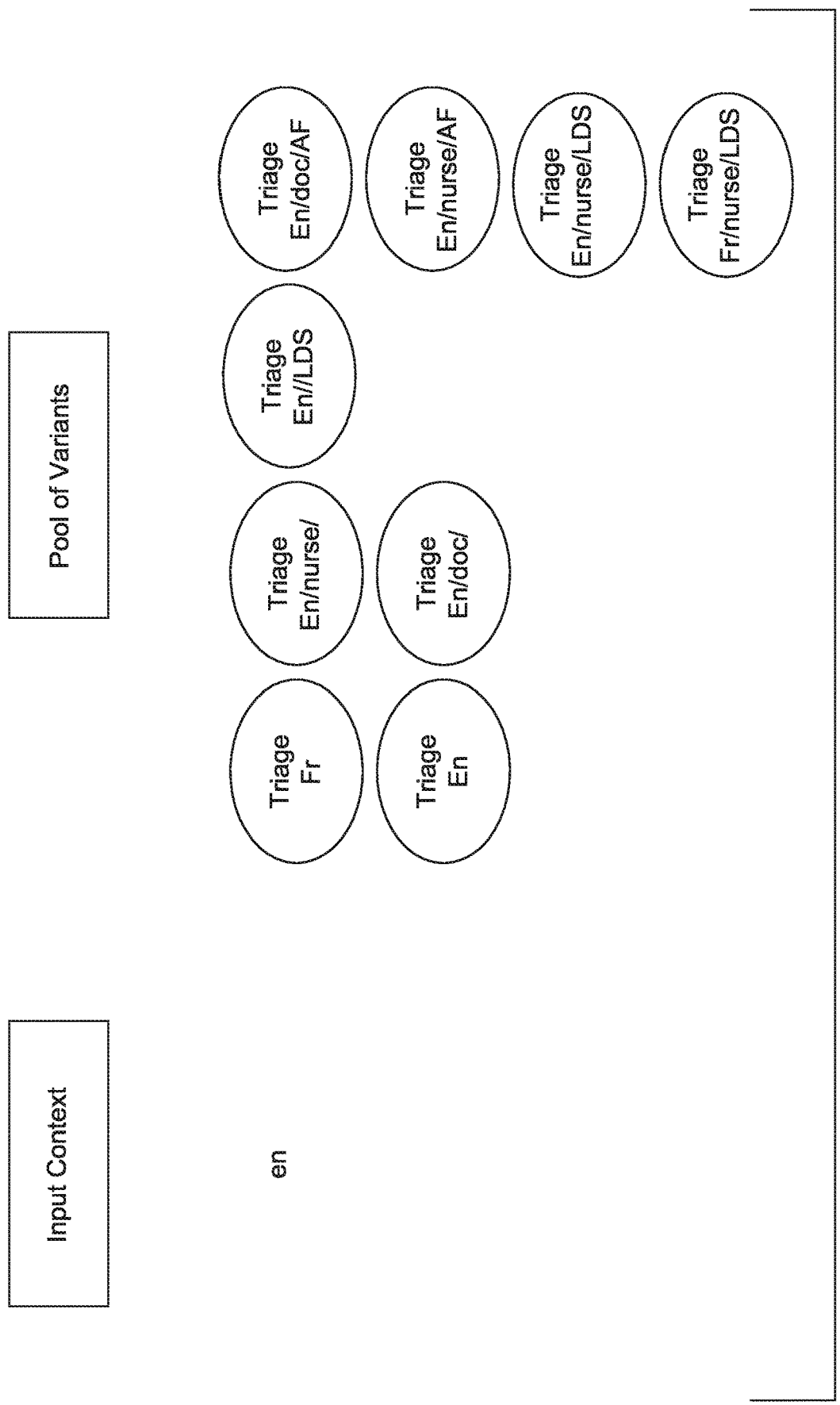
FIG. 19 illustrates an example in which context resolution may occur at packaging time.
Figure 20:
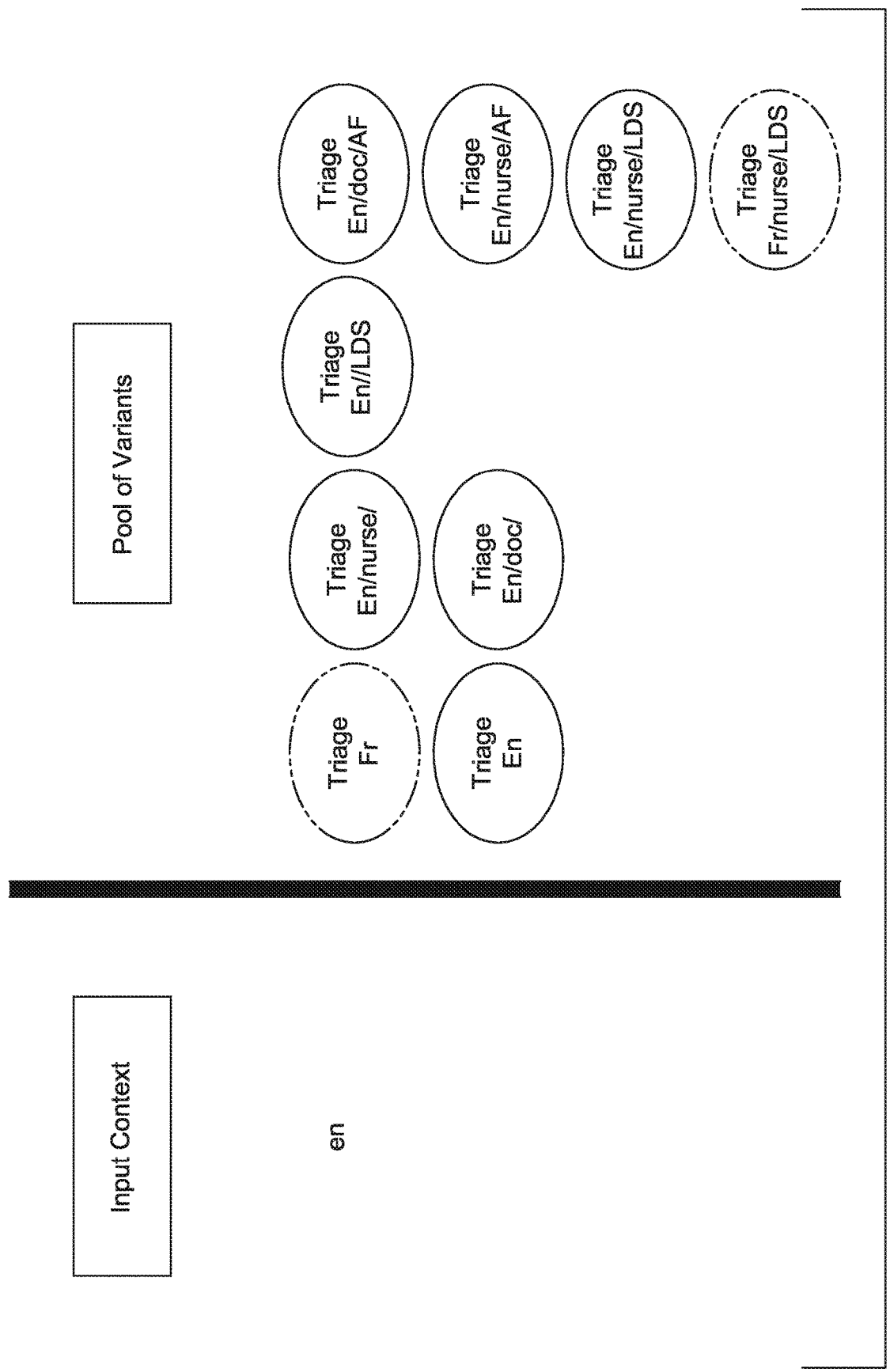
FIG. 20 illustrates an example in which conflicting context variants are rejected.
Figure 21:
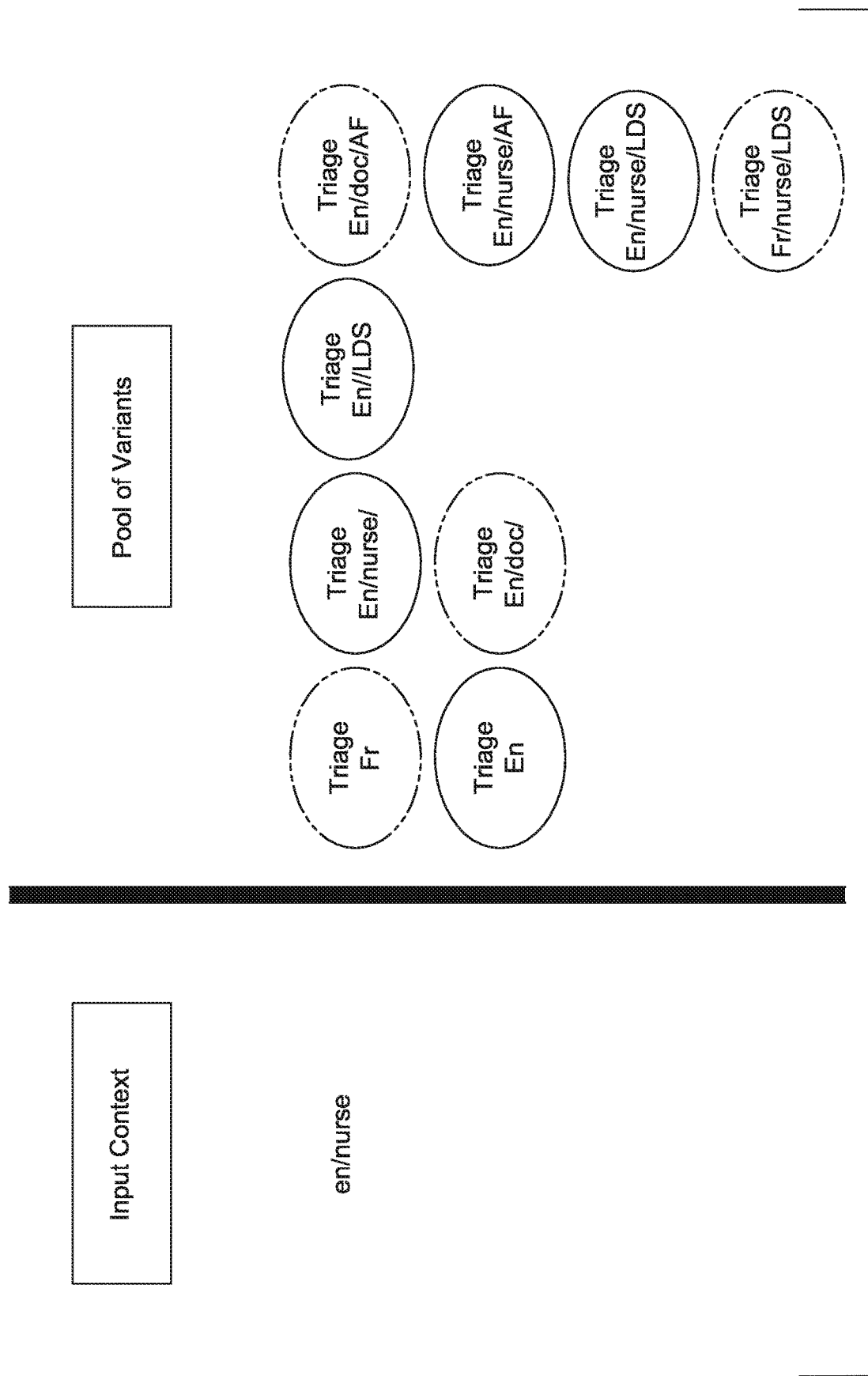
FIG. 21 shows conflicting context variants that may be further eliminated based on an input context at packaging time.
Figure 22A:
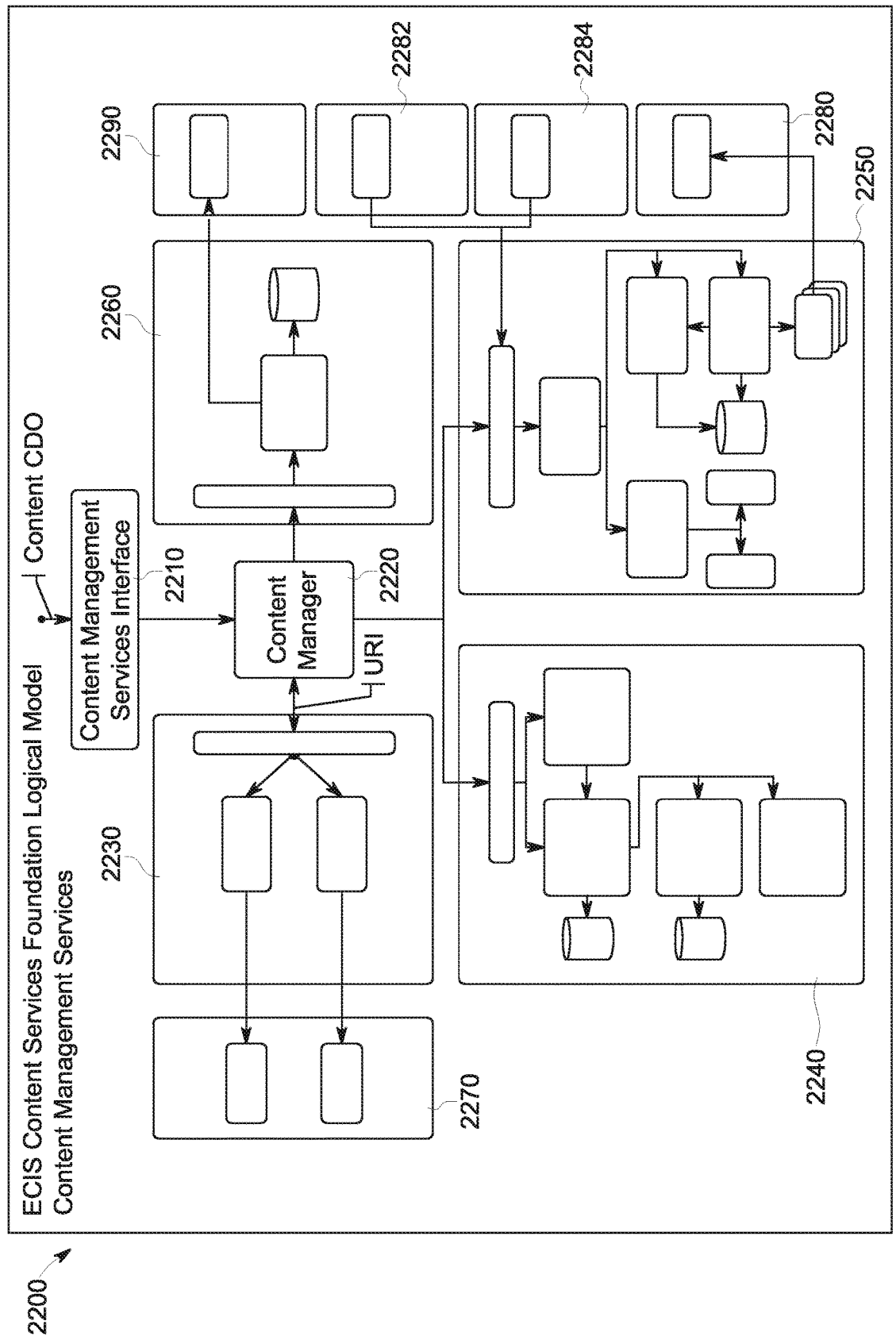
FIGS. 22-23, consisting of FIGS. 22a-22g and FIGS. 23a-23i, respectively, illustrate example content management services systems.
Figure 22B:
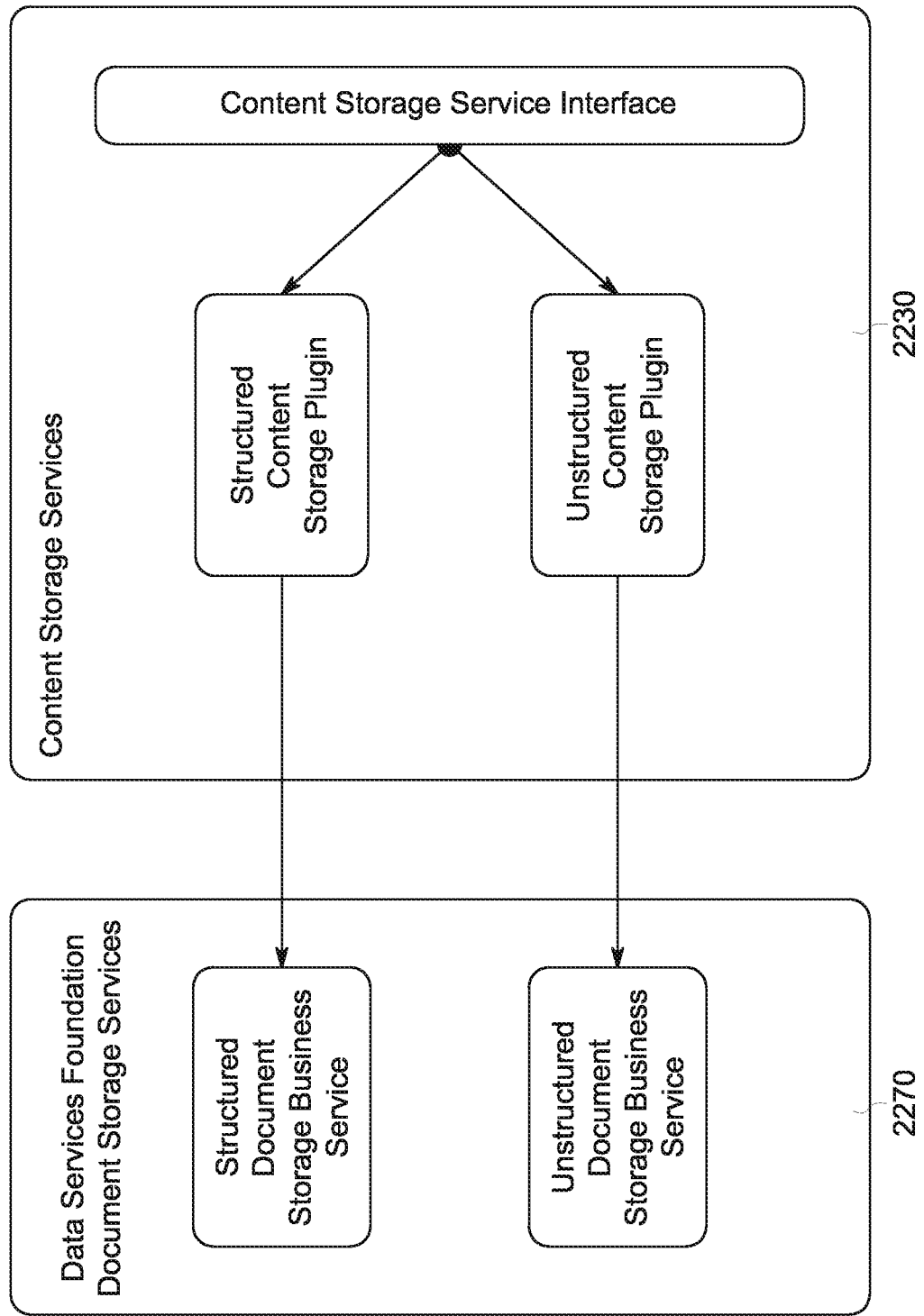
Figure 22C:
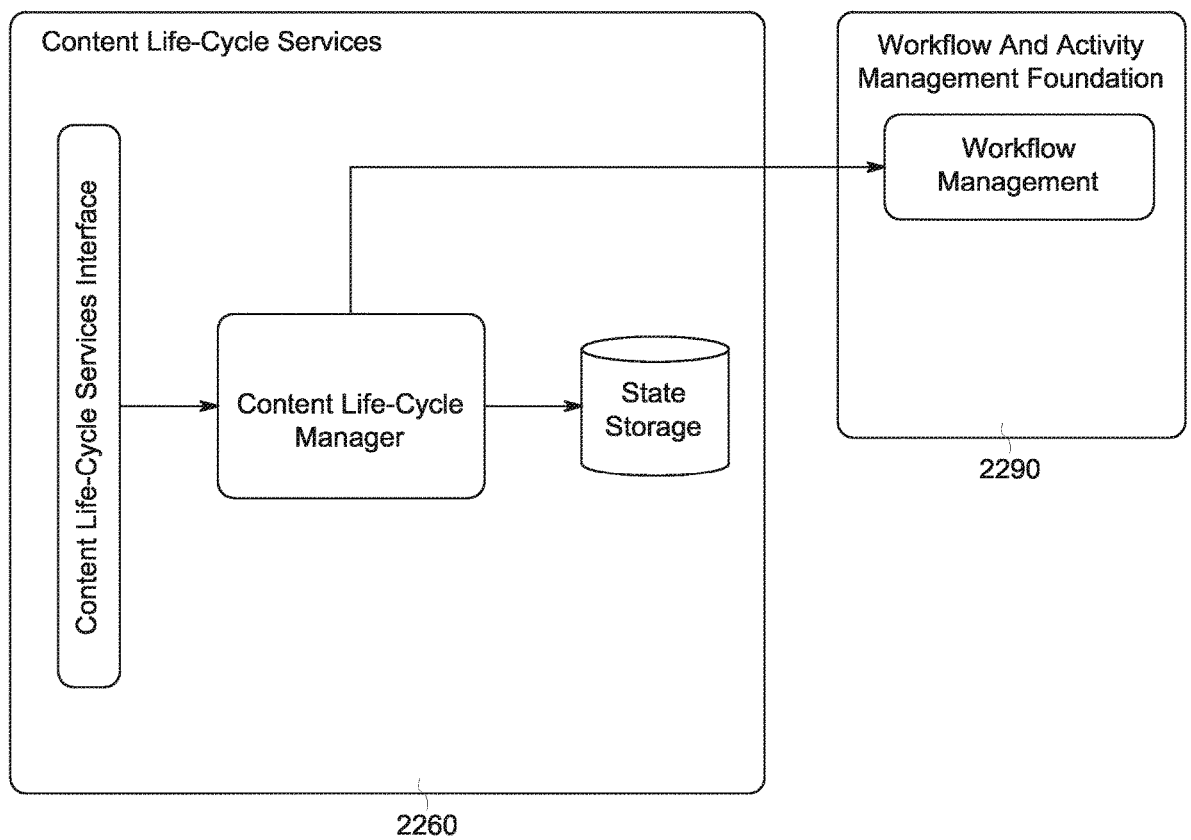
Figure 22D:
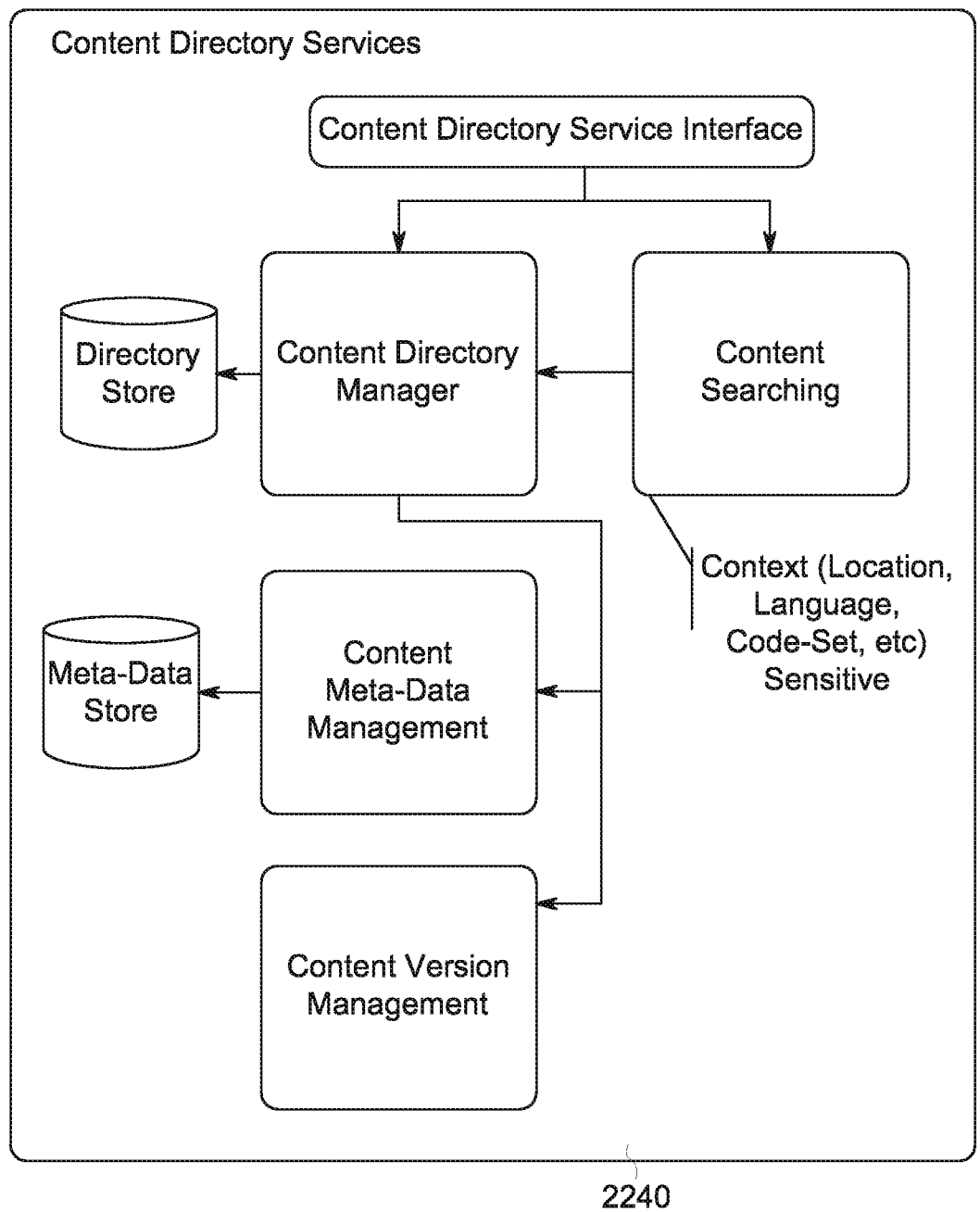
Figure 22E:
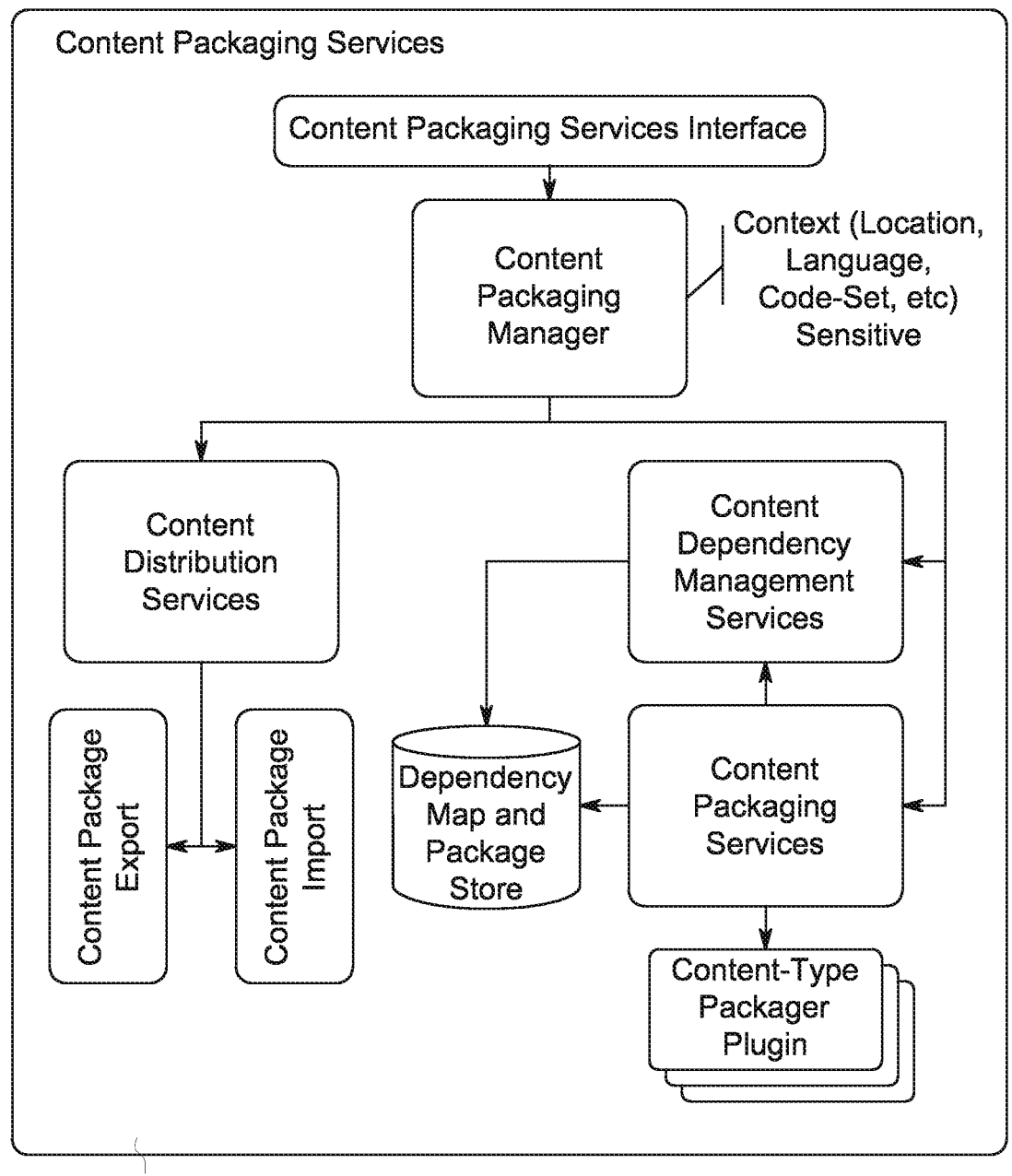
Figure 22F:
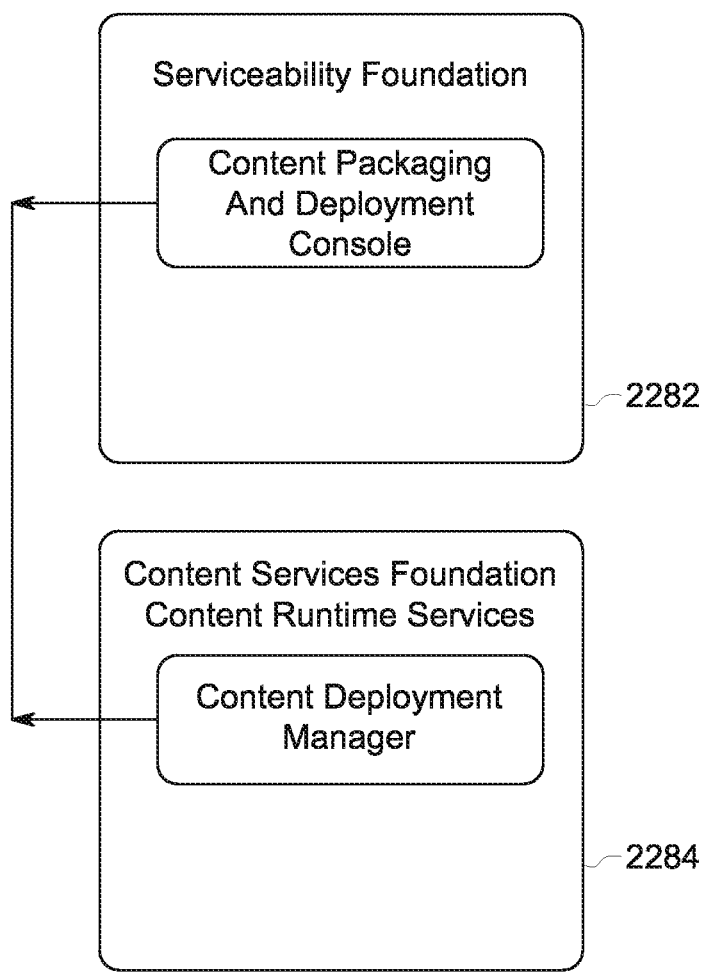
Figure 22G:
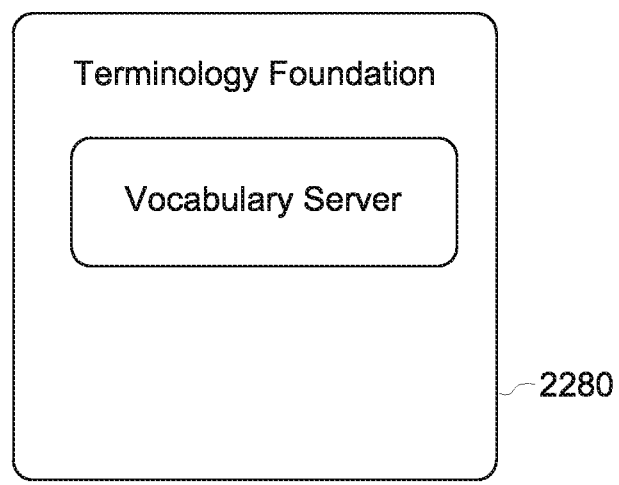
Figure 23A:
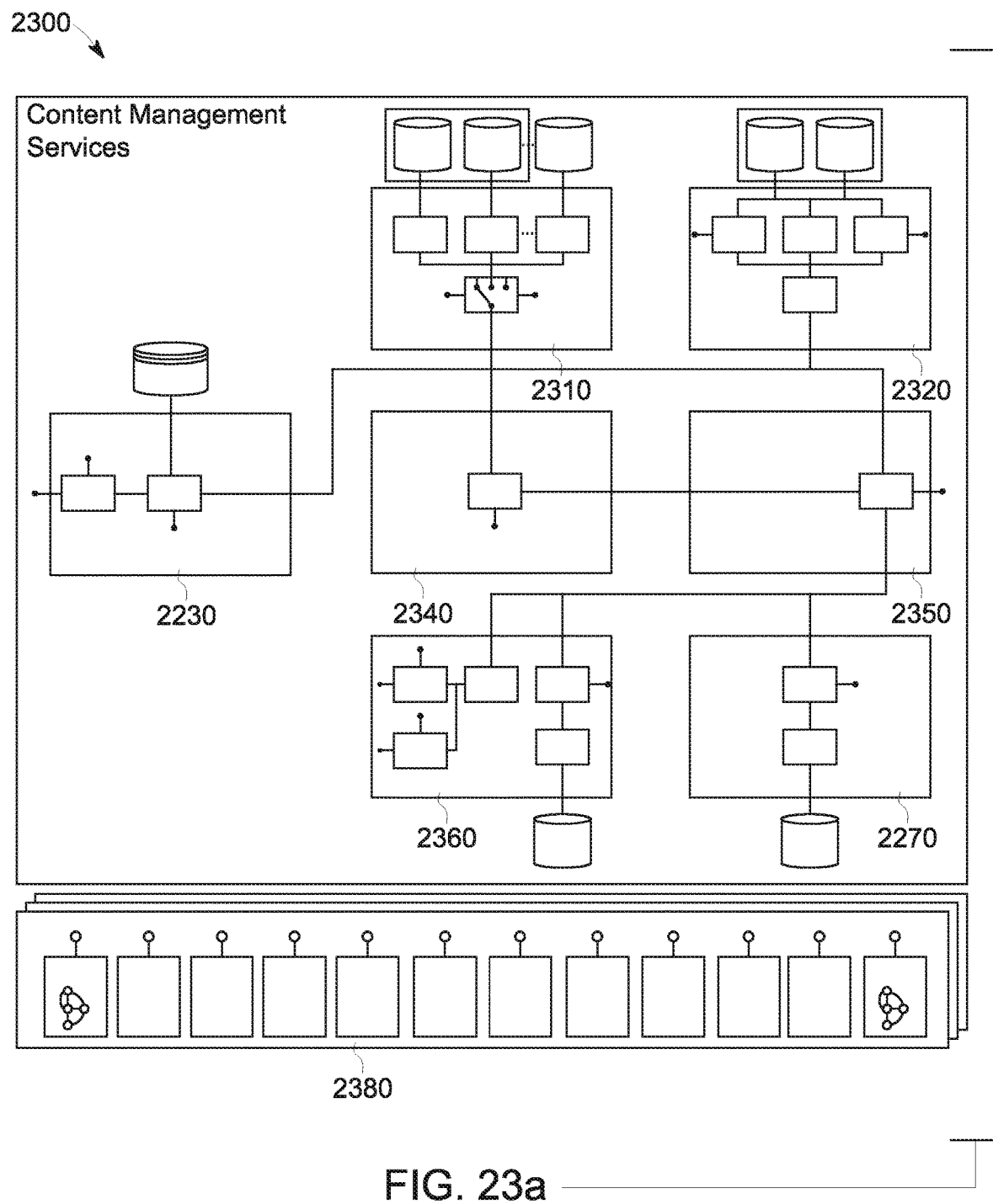
Figure 23B:
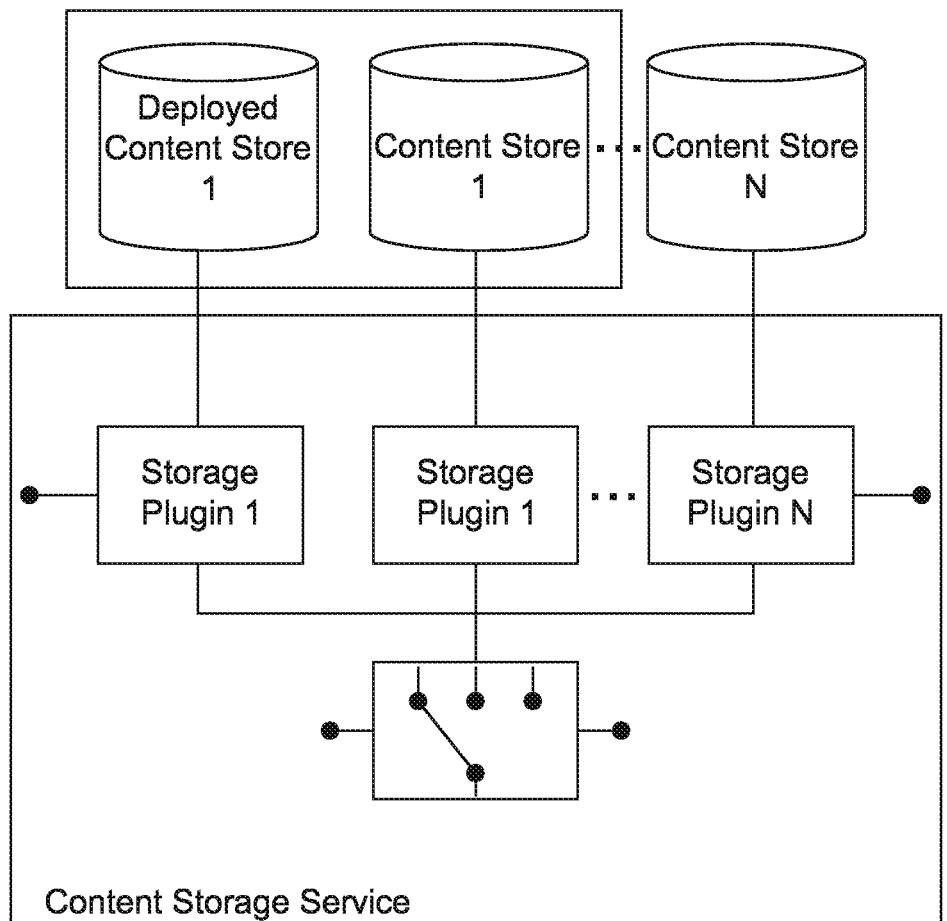
Figure 23C:
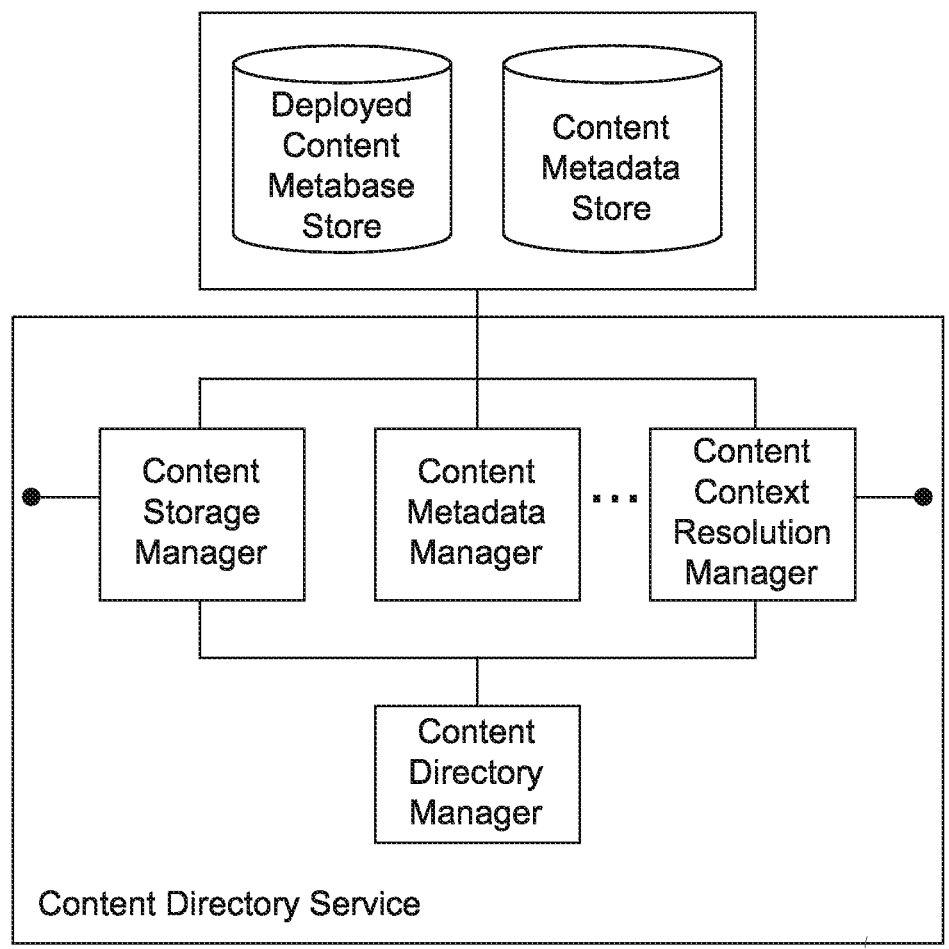
Figure 23D:
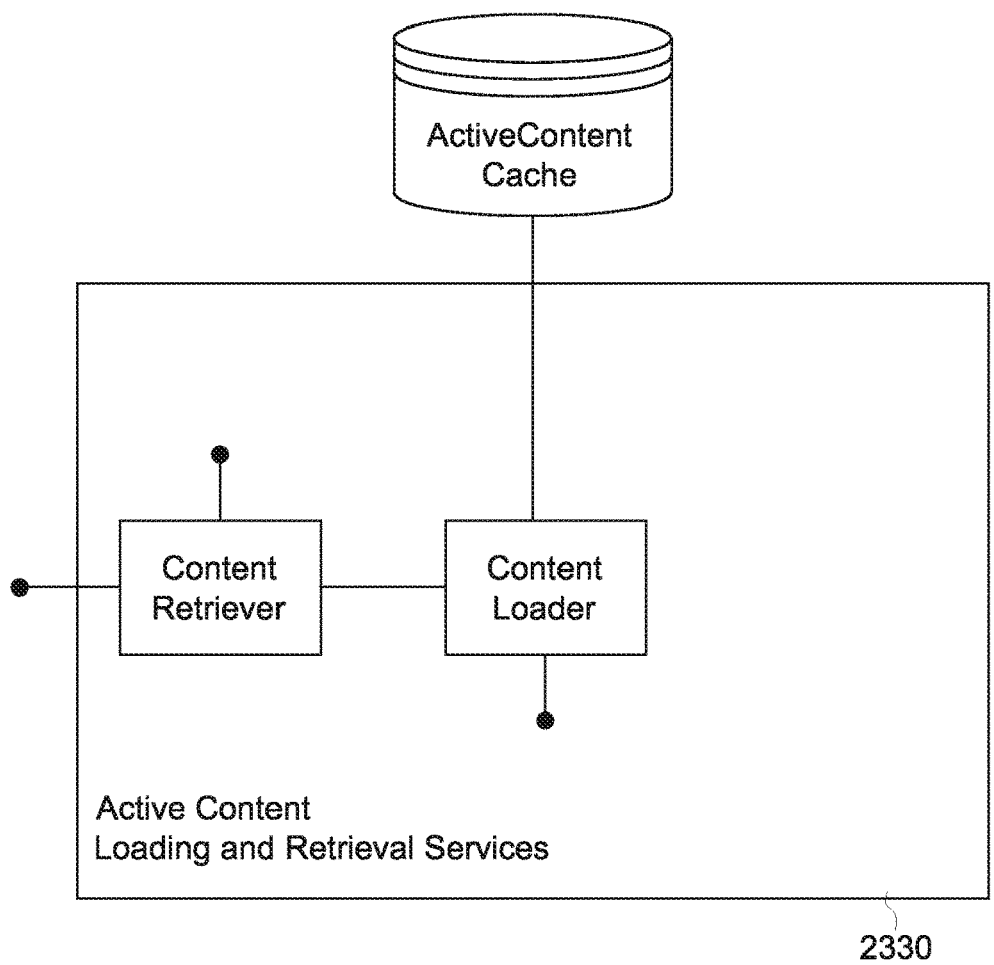
Figure 23E:
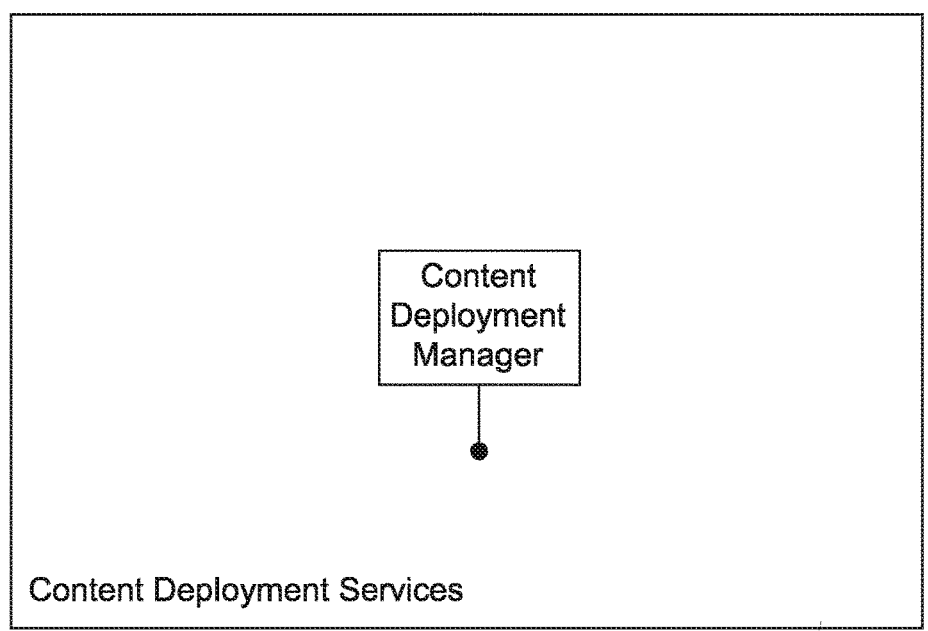
Figure 23F:
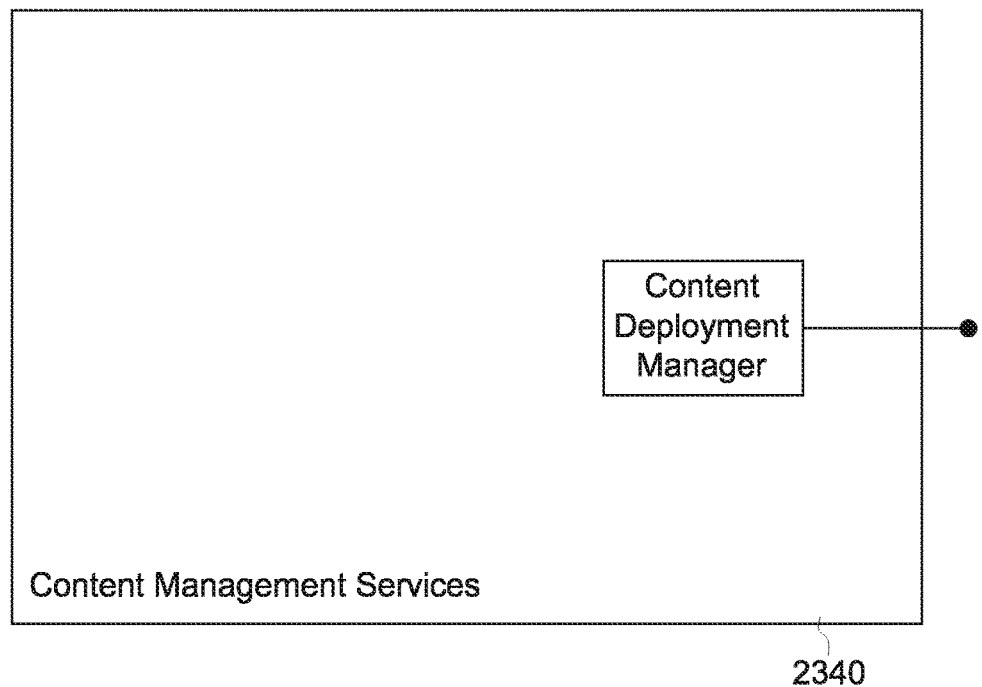
Figure 23G:
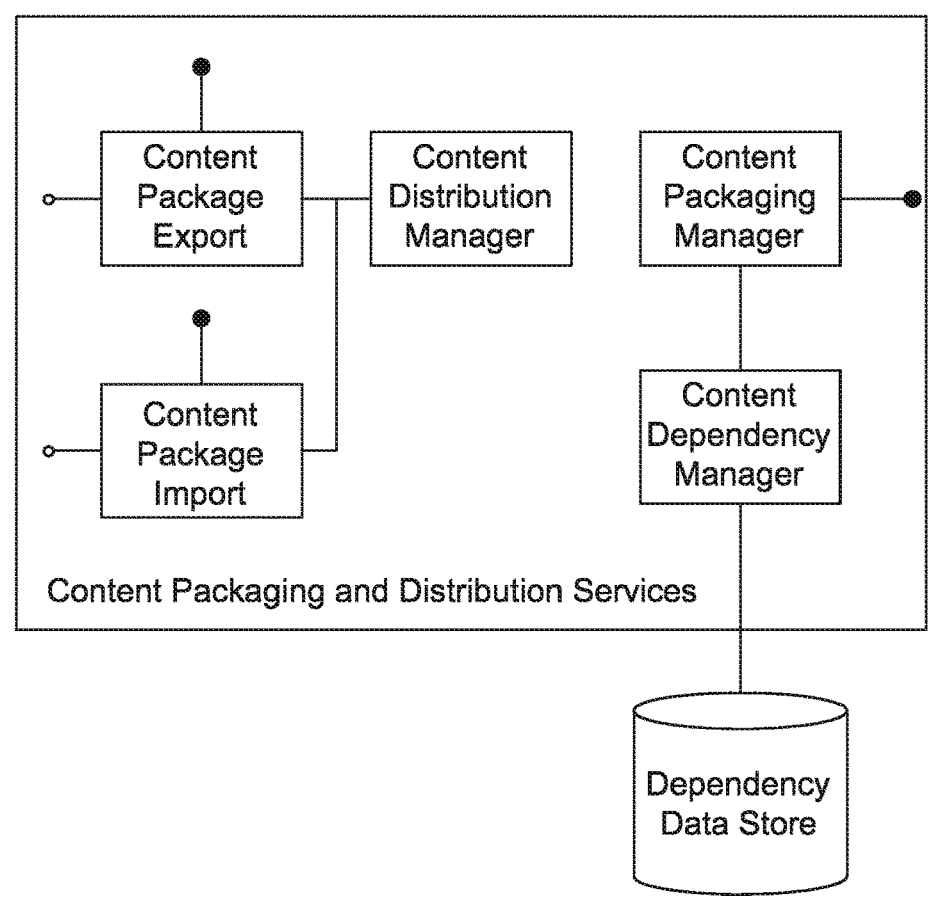
Figure 23H:
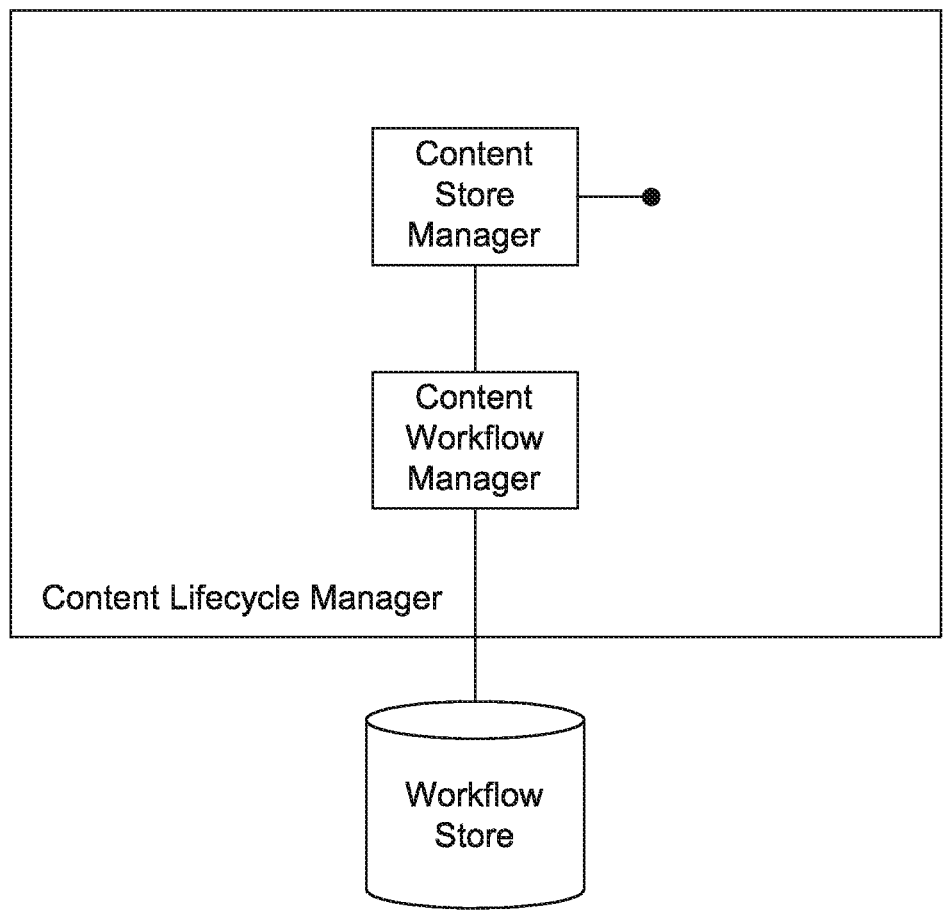
Figure 23I:
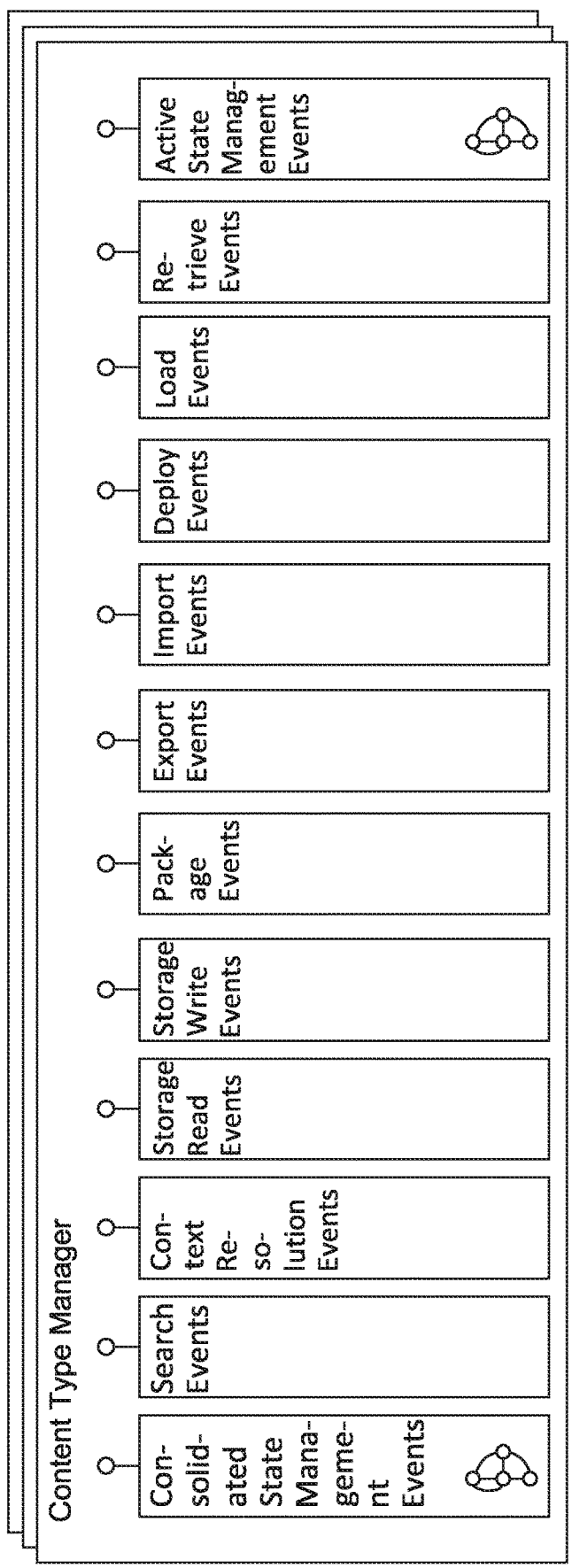

As illustrated in the example of FIG. 19, context resolution may occur at packaging time. First, as illustrated in the example of FIG. 20, conflicting context variants are rejected. As shown in the example of FIG. 21, conflicting context variants may be further eliminated based on an input context at packaging time.

FIG. 22 illustrates an example content management services system 2200. Content management services 2200 includes interrelationships of content storage, directory, lifecycle management, and packaging services. Packaging includes distribution and dependent management services, for example. The example content management services system 2200 manages content lifecycle.

The example system 2200 includes an interface 2210, which connects to a content manager 2220. The content manager 2220 connects with content storage services 2230, content directory services 2240, content packaging services 2250, and content lifecycle services 2260.

Content storage services 2230 includes an interface 2231 providing access to structured and unstructured content storage 2232-2233 and interacts with a data services foundation for document storage services 2270 for structured and/or unstructured document services 2270-2271.

Content directory services 2240 provides, via an interface 2241, content searching 2242 along with a content directory manager 2243. The manager 2243 accesses content metadata management 2244 and content version management 2245, for example. Content directory services 2240 include a directory store 2246 and a metadata store 2247, for example.

Content packaging services 2250 include an interface 2251 providing access to a content packaging manager 2252. The manager 2252 interacts with content distribution services 2253, content dependency management services 2254, and content packaging services 2255. Content distribution services 2253 connect to a content package export 2256 and content package export 2257. Content dependency management services 2254 and content packaging services 2255 communicate with a dependency map and package store 2258. Content packaging services 2255 also communicates with a content-type package plug-in 2259, which communicates with a terminology foundation 2280, in the example of FIG. 22. As shown in FIG. 22, the interface 2251 communicates with a serviceability foundation 2282 and a content services foundation 2284.

Content lifecycle services 2260 includes an interface 2261 for a content lifecycle manager 2262 which connects to storage 2263. The content lifecycle manager 2262 interacts with a workflow and activity management foundation 2290.

FIG. 23 illustrates another example content management services system 2300. In the example of FIG. 23, the system 2300 includes a content storage service 2310, a content directory service 2320, an active content loading and retrieval service 2330, a content deployment service 2340, a content management service 2350, a content packaging and distribution service 2360, a content lifecycle manager 2370, and a content type manager 2380. Components of the example system 2300 operate as described above with respect to managing, storing, loading, deploying, etc., content in a content-driven system and/or process.

Figure 24:
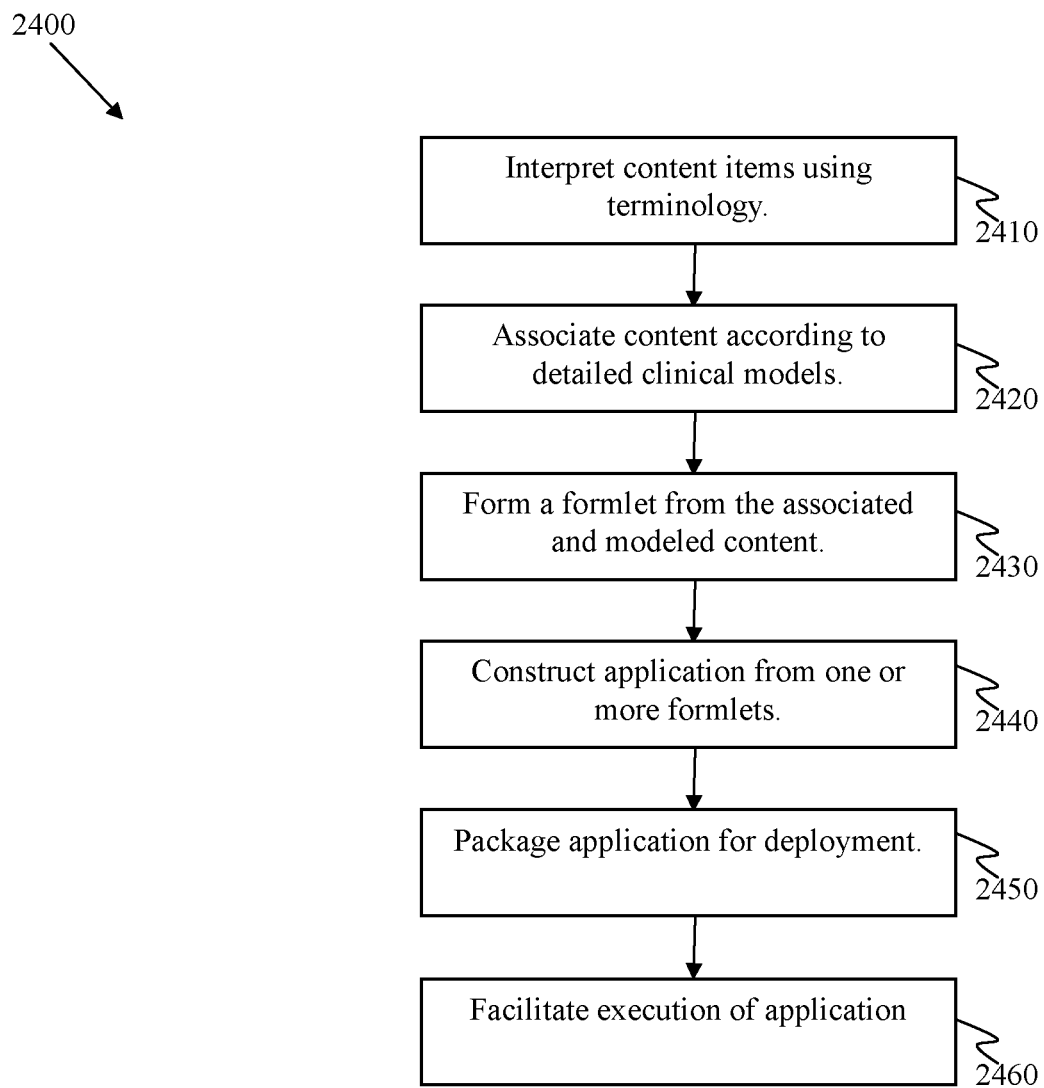
FIG. 24 illustrates a flow diagram for an example method of creating and managing a clinical application in a content-based system.

FIG. 24 illustrates a flow diagram for an example method 2400 of creating and managing a clinical application in a content-based system. At block 2410, terminology is used to interpret one or more content items including associated data. For example, content including lab tests can be evaluated to determine the lab test name(s) using the available terminology. Terminology may be common and coded across a customer base and/or particularly designed for a customer, for example.

Clinical content includes structured knowledge components such as decision support rules, protocols, reports, user preferences (e.g. triage form layout) and unstructured knowledge components such as discharge instructions, and guidelines. Content can include and/or be associated with clinical decision support.

At block 2420, the one or more content items (e.g., instances of a content class) from one or more content classes are associated according to one or more detailed clinical models (e.g., CEMs). For example, data for lab test results identified using the terminology can be modeled using CEMs.

In certain examples, a detailed clinical model defines, at a granular level, the structure and content of a data element. A detailed clinical model pulls the information together into a single, explicit, and computable form. The detailed clinical models or clinical element models (CEMs) govern the content and structure of data objects stored in an example clinical repository and used by one or more clinical applications, for example. In addition, CEMs are extensible, such that content authors may add new CEMs or attributes to existing CEMs without requiring major changes to database structures or software, for example.

At block 2430, a formlet is formed from the one or more associated and modeled content items. A formlet provides a way to display a particular content item (e.g., a way to display a particular lab result). The formlet is formed according to a detailed clinical model, for example, organizing the associated content items, which are also organized according to one or more detailed clinical models, for example.

At block 2440, a clinical application form is constructed from one or more formlets. For example, a detailed clinical model can be used to organize one or more formlets into a clinical application, such as a dashboard or other clinical information view.

A clinical form definition provides an application or view (e.g., a dashboard) of a collection of formlets (e.g., a multi-patient view (MPV) showing one or more lab results and/or other information). For example, if a particular MPV definition is moved from one customer to another, the MPV definition along with other content items on which the form definition depends are imported into the new customer's knowledge repository. Content items may include appropriate formlets, CEMs, and terminology, for example.

At block 2450, the application is packaged for deployment. For example, the application may be packaged in an executable, a container, a series of files to be compiled by a customer and/or at run time, etc. The content and data organized to form the clinical application can be transmitted together or separately to a customer site for installation and/or execution, for example.

At block 2460, execution of the clinical application is facilitated. For example, packaged content (e.g., as a form including formlets including models organizing content according to a terminology) is provided for execution based on a reference platform. The reference platform facilitates content interpretation and management and also provides reference services to facilitate installation and execution of the clinical application by a customer.

Figure 25:
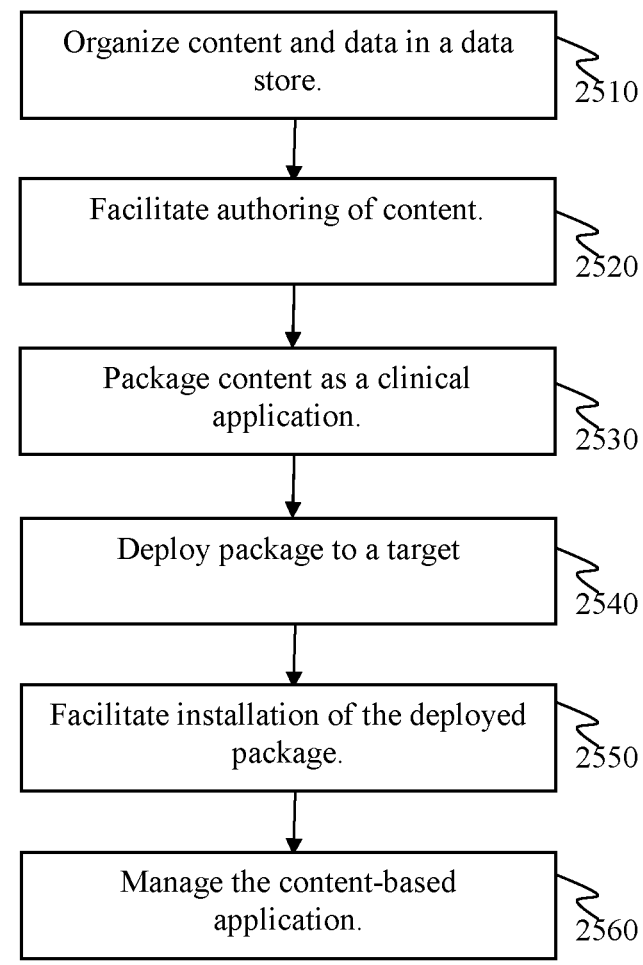
FIG. 25 illustrates a flow diagram for an example method of content-driven clinical information management.

FIG. 25 illustrates a flow diagram for an example method 2500 of content-driven clinical information management. At block 2510, content and data are organized in a repository and/or other electronic data store. For example, data (e.g., clinical and/or non-clinical data) relating to a patient, a condition, a diagnosis, a treatment, a best practice or other reference information can be stored in a repository, such as a clinical data repository. Content is an externalization or parameterization of "the instructions" that tell applications how to work. For example, content is a collection of externalized information that tells an application, in conjunction with data, how to behave. In certain examples, a clinical knowledge platform takes in and executes content against data to render applications visually and behaviorally.

In certain examples, content can include data read and interpreted by a program to define or modify presentation, behavior, and/or semantics of the program and/or of application data consumed by the program, for example. Content includes documents presented to a client by a program without modification, for example. Content can be created, stored, deployed, and/or retrieved independently of the creation and deployment of the program(s) consuming the data, for example.

Classes of content can include configuration content, preferences content, reference content, application content, etc. Content types can combine behaviors of two or more classes, for example. In certain examples, each content type is associated with a generic, extensible structure that particular content instances of the content type follow. A content item can be associated with a plurality of variants for one or more contexts (e.g., role, language, location, customer, department, clinical type, user context, patient context, etc.). A manual and/or automated selection of a variant can be made for a general content type.

At block 2520, content can be authored as all (e.g., a form) or part (e.g., a formlet) of an application or view (e.g., a dashboard, such as a hospital-acquired conditions dashboard, rapid recovery dashboard, MPV, etc.). A clinical application can be generated using a terminology foundation for content and data, modeled according to one or more detailed clinical models, along with a dependency map illustrating relationships and dependencies between content/data according to the one or more clinical models.

In certain examples, content can be scalable. For example, the process 2500 is scalable in that the process 2500 can support core content as determined by and/or for a particular application in addition to customer/competitor specific content. Content can be versionable to capture desired variation in program behavior and/or semantics, for example. The process 2500 is also expressive to allow end-users to consume the content to support individual preferences at an enterprise level, for example.

At block 2530, content and data are packaged as one or more clinical applications. For example, application(s) can be packaged according to one or more detailed clinical data models (e.g., CEMs) organizing content and leveraging data according to the content and model(s). In certain examples, one or more clinical applications can be packaged differently according to customer, namespace, location, etc.

At block 2540, the package can then be distributed or deployed to one or more targets for installation. The package can be distributed according to namespace, for example. Content can be distributed as a large set of items (e.g., a new installation), as one or more individual items (e.g., a bug fix), etc. A deployed content item is logically (and possibly physically) a different object than the content item being deployed. For example, a deployed content item has an independent state and lifecycle. Multiple content items can be created during deployment (e.g., deploying a CDL model can generate a CE Type object and an XML Schema). In certain examples, a source content item may not exist in the runtime system (e.g., the source CDL model is not deployed, the generated CE Type object is deployed). In certain examples, each deployed content item is bundled with content items used to execute or consume the item. For example, a bundle or content frame of items can be formed in a content package for deployment.

At block 2550, the distributed content-based application is installed. The package can be a new installation, an update, an upgrade, a patch, etc. In certain examples, content dependencies are resolved upon installation. Content dependencies can also be resolved at packaging, on deployment, at runtime, etc.

At block 2560, the content-based application is managed. For example, one or more content type managers interact with a content management frame to implement event handlers. Event handlers can handle dependencies between content items (e.g., between resolved context variants of content items). In certain examples, system management tools are provided to further create, export, import, and/or deploy content packages. In certain examples, a content frame including deployed content items is loaded from storage and made available for use by one or more running applications. Content items in the content frame can be translated during loading, for example, to resolve terminology designations, retrieve pick-lists, etc. In certain examples, a content type manager determines whether to translate at retrieval time, load time, etc.

In certain examples, lifecycle management involves a set of workflows that manage transition of a content item from one state to another (e.g., via a set of states and state transitions represented as a state machine for a content type). Each state in the content type state machine is associated with a workflow that manages the content item when in that state. Workflows can be represented as content items to allow variation across system implementations.

Certain examples also provide semantic interoperability. The process 2500 provides an infrastructure for clinical entities to create semantically interoperable systems to derive clinical, research and business benefits thereof.

In certain examples, the process 2500 enables modular content packaging and pluggable deployment. This flexibility allows tailorable content to support different types of clients to augment a "surround and supplement strategy", wherein a small client with limited budget can go live with only couple of modules/content-deployers while a large enterprise customer might want a whole suite of content management infrastructure.

Certain examples define processes apriori to help ensure that structured and unstructured clinical content development and management is predictable, measurable, efficient and integrated into application lifecycle management. Building a clinical application using the content management process 2500 provides significant benefits by making it scalable, expressive, standards supportive, semantically interoperable, and flexible.

Certain examples provide a customizable application separate from a maintainable system. The clinical information system application is implemented in content, that is, as a set of content items that are created and maintained independently of the system, often by the customers of the system themselves. The reference platform (e.g., the system) is maintained, enhanced, tested, and deployed using traditional development techniques by the vendor. Since the application (e.g., in content) is independent of the reference platform, the two can evolve largely independently of each other. This allows a much greater degree of possible customization without reducing the maintainability of the system.

Clinical information systems (CIS) that are content-driven provide functionality that improves clinical outcomes by enhancing compliance with institutionally/nationally recognized standards of care and reduce practice variation. A new process has been defined to streamline the clinical content management from its inception to its consumption by the CIS.

Figure 26:
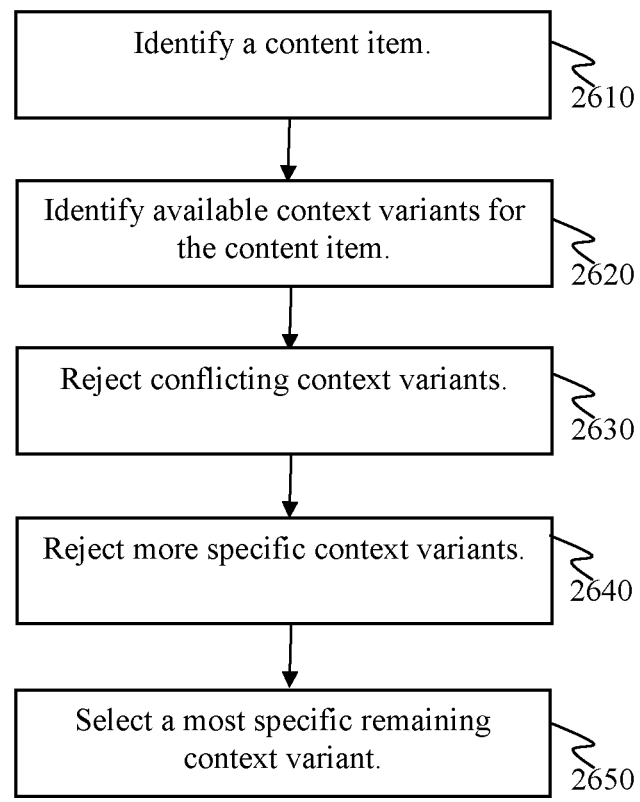
FIG. 26 illustrates a flow diagram for an example method of heuristic content resolution in an extensible content management system.

FIG. 26 illustrates a flow diagram for an example method 2600 of heuristic content resolution in an extensible content management system. For example, a particular content item, such as content item 510 shown in FIG. 5, may have a plurality of context variants which may in turn have a plurality of context variants. A heuristic and/or other algorithm can be applied to identify an appropriate (e.g., a most appropriate) context variant for a particular content item based on one or more criterion (e.g., a user's current context). This can be referred to as context resolution. Context resolution involves conditioning a selection, composition, and/or behavior of a content item based on a specified value, such as a context of the user. FIGS. 12-21 illustrate examples of heuristic variant determination as described further in connection with the method 2600 of FIG. 26.

Context resolution can occur at three levels, for example: selection of a content item, selection of a content frame, and translation of a content item. Selection of one or more content items on which a content item being deployed is dependent can occur based on context, for example. Selection of a content frame based on context can occur when the content frame is retrieved by an application. Translation of a content item based on context can occur when loading or retrieving a content frame.

Multiple variants of a content item can be resolved based on who, what, or where the content consumer is, for example. This allows users to create, specialize, and/or customize their own content on top of default or vendor-released content (e.g., shareable and interopeable content). This allows for a single content type to vary by properties associated with the content consumer without having to customize every application that consumes a particular content item to be aware of the appropriate rules to vary the display of the content.

In clinical applications, content can be displayed in different ways based on a context of application use. For example, a role of a clinician may impact what clinical information the user wants to see and how the user wants to see it. A location of a user can also impact the type of information that is desired to be displayed based on clinical need and preference, for example. There is also a need to display clinical information in multiple languages, especially for patients.

At block 2610, a content item is identified. The content item can be identified in conjunction with a formlet combining a plurality of content items according to one or more clinical element models, for example. The formlet may be part of a form to provide information and functionality to a user according to one or more clinical element models, for example. Identification and context resolution can occur at runtime, at packaging, etc.

At block 2620, available context variants for the content item are identified. For example, a content item can be stored in a clinical repository along with a plurality of context variants and an indication of the available context variants for that content item. Context variants can be identified based on an input context value or values (e.g., metadata associated with the content indicating user, role, location, namespace, department, etc.) provided at runtime, packaging time, etc., for example.

At block 2630, conflicting context variants are rejected. For example, if an input context indicates a language of "English" and a role of "nurse", then conflicting variants from the pool of variants including "French", "doctor", etc., are rejected or eliminated from consideration.

At block 2640, more specific context variants are rejected. For example, for an input context of English nurse (e.g., "en/nurse"), context variants that provide additional detail/variation, such as Labor and Delivery (e.g., LDS), Labor and Delivery Nurse, etc., are eliminated or removed from consideration.

At block 2650, a most specific variant of the remaining context variants for that content item, is selected. For example, continuing the English nurse context input example, remaining variants English (e.g., "en") and English nurse (e.g., "en/nurse") are reviewed to select a most specific remaining variant (e.g., as shown in FIGS. 14-15). In this example, that context variant is Triage English nurse. That context variant is selected for use as the particular content item for the clinical application (e.g., a formlet forming part of a form).

Resolution of context by an application allows appropriate information to be displayed based on who, what, and/or where the user of the application is. This ability enables streamlined workflows and targeted documentation for clinical use. This also gives flexibility to customize content for specific use(s). Thus, context selection or resolution utilizes a heuristic to resolve ambiguity or conflict among available context variants (e.g., weighting or priority schemes, default rules, etc.). Changing/adding a context variant, changing weight of a context attribute, etc., can change context resolution on another content item, for example.

While an example manner of implementing systems and methods have been illustrated in the figures, one or more of the elements, processes and/or devices illustrated in the figures may be combined, divided, re-arranged, omitted, eliminated and/or implemented in any other way. Further, one or more components and/or systems may be implemented by hardware, software, firmware and/or any combination of hardware, software and/or firmware. Thus, for example, any of the example components and/or systems may be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the example components and/or systems are hereby expressly defined to include a tangible medium such as a memory, DVD, Blu-ray, CD, etc., storing the software and/or firmware. Further still, any of the example systems may include one or more elements, processes and/or devices in addition to, or instead of, those illustrated in the figures, and/or may include more than one of any or all of the illustrated elements, processes and devices.

The flow diagrams depicted in the figures are representative of machine readable instructions that can be executed to implement example processes and/or systems described herein. The example processes may be performed using a processor, a controller and/or any other suitable processing device. For example, the example processes may be implemented in coded instructions stored on a tangible medium such as a flash memory, a read-only memory (ROM) and/or random-access memory (RAM) associated with a processor (e.g., the example processor 2712 discussed below in connection with FIG. 27). Alternatively, some or all of the example processes may be implemented using any combination(s) of application specific integrated circuit(s) (ASIC (s)), programmable logic device(s) (PLD(s)), field programmable logic device(s) (FPLD(s)), discrete logic, hardware, firmware, etc. Also, some or all of the example processes may be implemented manually or as any combination(s) of any of the foregoing techniques, for example, any combination of firmware, software, discrete logic and/or hardware. Further, although the example processes are described with reference to the figures, other methods of implementing the processes of may be employed. For example, the order of execution of the blocks may be changed, and/or some of the blocks described may be changed, eliminated, sub-divided, or combined. Additionally, any or all of the example processes of may be performed sequentially and/or in parallel by, for example, separate processing threads, processors, devices, discrete logic, circuits, etc.

Figure 27:
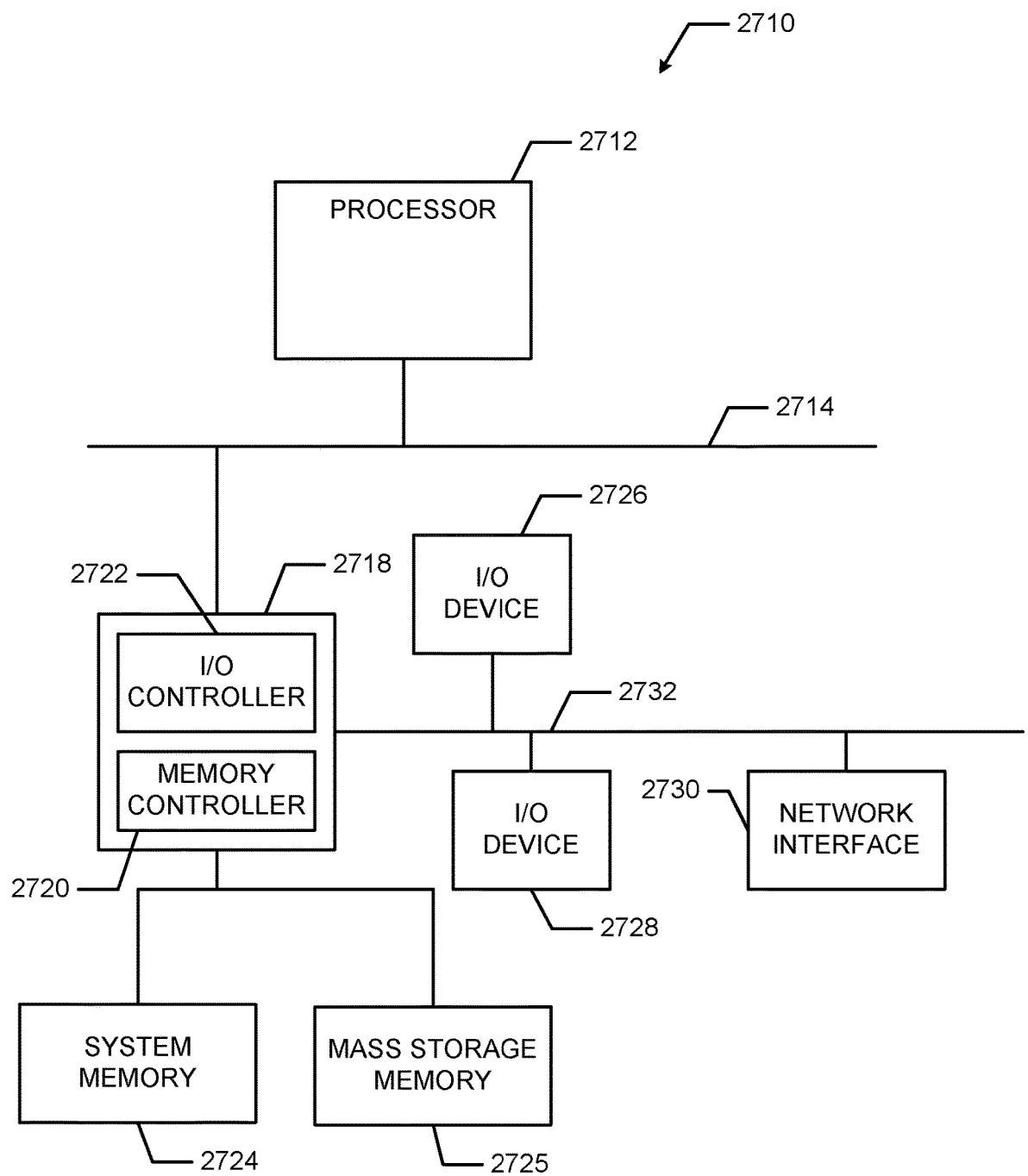
FIG. 27 is a block diagram of an example processor system that may be used to implement the apparatus and methods described herein.

FIG. 27 is a block diagram of an example processor system 2710 that may be used to implement the apparatus and methods described herein. As shown in FIG. 27, the processor system 2710 includes a processor 2712 that is coupled to an interconnection bus 2714. The processor 2712 may be any suitable processor, processing unit or microprocessor. Although not shown in FIG. 27, the system 2710 may be a multi-processor system and, thus, may include one or more additional processors that are identical or similar to the processor 2712 and that are communicatively coupled to the interconnection bus 2714.

The processor 2712 of FIG. 27 is coupled to a chipset 2718, which includes a memory controller 2720 and an input/output (I/O) controller 2722. As is well known, a chipset typically provides I/O and memory management functions as well as a plurality of general purpose and/or special purpose registers, timers, etc. that are accessible or used by one or more processors coupled to the chipset 2718. The memory controller 2720 performs functions that enable the processor 2712 (or processors if there are multiple processors) to access a system memory 2724 and a mass storage memory 2725.

The system memory 2724 may include any desired type of volatile and/or non-volatile memory such as, for example, static random access memory (SRAM), dynamic random access memory (DRAM), flash memory, read-only memory (ROM), etc. The mass storage memory 2725 may include any desired type of mass storage device including hard disk drives, optical drives, tape storage devices, etc.

The I/O controller 2722 performs functions that enable the processor 2712 to communicate with peripheral input/output (I/O) devices 2726 and 2728 and a network interface 2730 via an I/O bus 2732. The I/O devices 2726 and 2728 may be any desired type of I/O device such as, for example, a keyboard, a video display or monitor, a mouse, etc. The network interface 2730 may be, for example, an Ethernet device, an asynchronous transfer mode (ATM) device, an 802.11 device, a DSL modem, a cable modem, a cellular modem, etc. that enables the processor system 2710 to communicate with another processor system.

While the memory controller 2720 and the I/O controller 2722 are depicted in FIG. 27 as separate blocks within the chipset 2718, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

The invention claimed is:

1. A method of forming a content-based application for execution, the method comprising:
   receiving, by a processor, an identifier for a root content item and an association between the root content item, a first context variant, and a second context variant;
   dynamically generating, by the processor, a content-based application by:
      generating a first content frame from the first context variant, the first context variant retrieved using the identifier for the root content item associated with the first content frame and the association between the root content item and the first context variant corresponding to the first content frame;
      generating a second content frame from the second context variant, the second context variant retrieved using the identifier for the root content item associated with the second content frame and the association between the root content item and the second context variant corresponding to the second content frame; and
      combining the first content frame and a second content frame according to one or more element models to form the content-based application; and
   deploying, by the processor, the content-based application for execution with respect to data via a reference platform.

2. The method of claim 1, wherein the first context variant corresponding to the first content frame provides content including a parameterization of instructions governing execution of the content-based application.

3. The method of claim 2, wherein the content includes at least one of configuration content, preference content, reference content, or application content.

4. The method of claim 1, wherein the reference platform includes a content class interpreter, a content class manager, and a reference platform service, the content-based application to execute with respect to the reference platform at runtime.

5. The method of claim 4, wherein the reference platform and the content-based application are independently scalable and modifiable.

6. The method of claim 1, wherein the first context variant is associated with a state and wherein the state is associated with a workflow to control a transition to a next state.

7. The method of claim 1, wherein dynamically generating the content-based application further includes organizing the first content frame and the second content frame into a first formlet, the first formlet and a second formlet to form the content-based application.

8. A computer-readable storage medium including instructions which, when executed by a processor, cause the processor to at least implement a method of forming a content-based application for execution, the method comprising:
   receiving an identifier for a root content item and an association between the root content item, a first context variant, and a second context variant;
   dynamically generating a content-based application by:
      generating a first content frame from the first context variant, the first context variant retrieved using the identifier for the root content item associated with the first content frame and the association between the root content item and the first context variant corresponding to the first content frame;
      generating a second content frame from the second context variant, the second context variant retrieved using the identifier for the root content item associated with the second content frame and the association between the root content item and the second context variant corresponding to the second content frame; and
      combining the first content frame and a second content frame according to one or more element models to form the content-based application; and
   deploying the content-based application for execution with respect to data via a reference platform.

9. The computer-readable storage medium of claim 8, wherein the first context variant corresponding to the first content frame provides content including a parameterization of instructions governing execution of the content-based application.

10. The computer-readable storage medium of claim 9, wherein the content includes at least one of configuration content, preference content, reference content, or application content.

11. The computer-readable storage medium of claim 8, wherein the reference platform includes a content class interpreter, a content class manager, and a reference platform service, the content-based application to execute with respect to the reference platform at runtime.

12. The computer-readable storage medium of claim 11, wherein the reference platform and the content-based application are independently scalable and modifiable.

13. The computer-readable storage medium of claim 8, wherein the first context variant is associated with a state and wherein the state is associated with a workflow to control a transition to a next state.

14. The computer-readable storage medium of claim 8, wherein dynamically generating the content-based application further includes organizing the first content frame and the second content frame into a first formlet, the first formlet and a second formlet to form the content-based application.

15. An apparatus comprising:
   a memory to store instructions, content, and data; and
   a processor, wherein the instructions, when executed by the processor, configure the processor to facilitate formation of a content-based clinical application by at least:
dynamically generating, using an identifier for a root content item and an association between the root content item, a first context variant, and a second context variant, a content-based application by:
generating a first content frame from the first context variant, the first context variant retrieved using the identifier for the root content item associated with the first content frame and the association between the root content item and the first context variant corresponding to the first content frame;
generating a second content frame from the second context variant, the second context variant retrieved using the identifier for the root content item associated with the second content frame and the association between the root content item and the second context variant corresponding to the second content frame; and
combining the first content frame and a second content frame according to one or more element models to form the content-based application; and
deploying the content-based application for execution with respect to data via a reference platform.

16. The apparatus of claim 15, wherein the first context variant corresponding to the first content frame provides content including a parameterization of instructions governing execution of the content-based application.

17. The apparatus of claim 15, wherein the reference platform includes a content class interpreter, a content class manager, and a reference platform service, the content-based application to execute with respect to the reference platform at runtime.

18. The apparatus of claim 17, wherein the reference platform and the content-based application are independently scalable and modifiable.

19. The apparatus of claim 15, wherein the first context variant is associated with a state and wherein the state is associated with a workflow to control a transition to a next state.

20. The apparatus of claim 15, wherein the first content frame and the second content frame are to be organized into a first formlet, the first formlet and a second formlet to form the content-based application.

* * * * *